US011946095B2

(12) United States Patent
Lam et al.

(10) Patent No.: US 11,946,095 B2
(45) Date of Patent: Apr. 2, 2024

(54) PARTICLES ASSOCIATED WITH OLIGONUCLEOTIDES

(71) Applicant: Becton, Dickinson and Company, Franklin Lakes, NJ (US)

(72) Inventors: Gretchen Yinbon Lam, Menlo Park, CA (US); Eleen Shum, Menlo Park, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 582 days.

(21) Appl. No.: 16/955,657

(22) PCT Filed: Dec. 18, 2018

(86) PCT No.: PCT/US2018/066291
§ 371 (c)(1),
(2) Date: Jun. 18, 2020

(87) PCT Pub. No.: WO2019/126209
PCT Pub. Date: Jun. 27, 2019

(65) Prior Publication Data
US 2021/0054436 A1    Feb. 25, 2021

Related U.S. Application Data

(60) Provisional application No. 62/607,812, filed on Dec. 19, 2017.

(51) Int. Cl.
C12Q 1/6806    (2018.01)
(52) U.S. Cl.
CPC .................. *C12Q 1/6806* (2013.01)
(58) Field of Classification Search
CPC ...... C12Q 1/68; C12Q 1/6806; C12Q 1/6869; C12Q 1/6808; C07H 21/00
See application file for complete search history.

(56) References Cited

U.S. PATENT DOCUMENTS

| | | |
|---|---|---|
| 4,510,244 A | 4/1985 | Parks et al. |
| 4,725,536 A | 2/1988 | Fritsch et al. |
| 5,124,246 A | 6/1992 | Urdea et al. |
| 5,149,625 A | 9/1992 | Church et al. |
| 5,200,314 A | 4/1993 | Urdea |
| 5,424,186 A | 6/1995 | Fodor et al. |
| 5,424,413 A | 6/1995 | Hogan et al. |
| 5,445,934 A | 6/1995 | Fodor et al. |
| 5,604,097 A | 2/1997 | Brenner |
| 5,635,352 A | 6/1997 | Urdea et al. |
| 5,635,400 A | 6/1997 | Brenner |
| 5,648,245 A | 7/1997 | Fire et al. |
| 5,654,413 A | 8/1997 | Brenner |
| 5,656,731 A | 8/1997 | Urdea |
| 5,658,737 A | 8/1997 | Nelson et al. |
| 5,714,330 A | 2/1998 | Brenner et al. |
| 5,744,305 A | 4/1998 | Fodor et al. |
| 5,759,778 A | 6/1998 | Li et al. |
| 5,763,175 A | 6/1998 | Brenner |
| 5,800,992 A | 9/1998 | Fodor et al. |
| 5,846,719 A | 12/1998 | Brenner et al. |
| 5,854,033 A | 12/1998 | Lizardi |
| 5,871,928 A | 2/1999 | Fodor et al. |
| 5,925,525 A | 7/1999 | Fodor et al. |
| 5,935,793 A | 8/1999 | Wong |
| 5,962,271 A | 10/1999 | Chenchick et al. |
| 5,962,272 A | 10/1999 | Chenchick et al. |
| 5,968,740 A | 10/1999 | Fodor et al. |
| 5,981,176 A | 11/1999 | Wallace |
| 5,981,179 A | 11/1999 | Lorinez et al. |
| 6,013,445 A | 1/2000 | Albrecht et al. |
| 6,040,138 A | 3/2000 | Lockhart et al. |
| 6,046,005 A | 4/2000 | Ju et al. |
| 6,060,596 A | 5/2000 | Lerner et al. |
| 6,064,755 A | 5/2000 | Some |
| 6,114,149 A | 9/2000 | Fry et al. |
| 6,117,631 A | 9/2000 | Nilsen |
| 6,124,092 A | 9/2000 | O'neill et al. |
| 6,138,077 A | 10/2000 | Brenner |
| 6,140,489 A | 10/2000 | Brenner |
| 6,172,214 B1 | 1/2001 | Brenner |
| 6,194,454 B1 | 2/2001 | Dow |
| 6,197,506 B1 | 3/2001 | Fodor et al. |
| 6,197,554 B1 | 3/2001 | Lin et al. |
| 6,235,475 B1 | 5/2001 | Brenner et al. |
| 6,235,483 B1 | 5/2001 | Wolber et al. |
| 6,265,163 B1 | 7/2001 | Albrecht et al. |
| 6,268,152 B1 | 7/2001 | Fodor et al. |
| 6,264,485 B1 | 9/2001 | Boyle |
| 6,284,460 B1 | 9/2001 | Fodor et al. |
| 6,309,822 B1 | 10/2001 | Fodor et al. |
| 6,309,823 B1 | 10/2001 | Cronin et al. |
| 6,326,148 B1 | 12/2001 | Pauletti et al. |
| 6,355,431 B1 | 3/2002 | Chee et al. |
| 6,355,432 B1 | 3/2002 | Fodor et al. |
| 6,372,813 B1 | 4/2002 | Travis |
| 6,395,491 B1 | 5/2002 | Fodor et al. |
| 6,406,848 B1 | 6/2002 | Bridgham et al. |
| 6,436,675 B1 | 8/2002 | Welch et al. |

(Continued)

FOREIGN PATENT DOCUMENTS

| | | |
|---|---|---|
| DE | 102008025656 | 12/2009 |
| EP | 0 799 897 | 10/1997 |

(Continued)

OTHER PUBLICATIONS

Achim et al., May 2015, High-throughput spatial mapping of single-cell RNA-seq data to tissue of origin. Nature Biotechnology, 33(5):503-511.

(Continued)

*Primary Examiner* — Ethan C Whisenant
(74) *Attorney, Agent, or Firm* — KNOBBE, MARTENS OLSON & BEAR, LLP

(57) ABSTRACT

Disclosed herein are methods, compositions, and kits for barcoding nucleic acids. For example, particles for barcoding are provided, where the particle comprises: a first plurality of oligonucleotide barcodes each comprising a target-binding region, and a second plurality of oligonucleotides each comprising a target-specific target-binding region.

24 Claims, 10 Drawing Sheets

Specification includes a Sequence Listing.

(56) References Cited

U.S. PATENT DOCUMENTS

| | | |
|---|---|---|
| 6,440,667 B1 | 8/2002 | Fodor et al. |
| 6,440,706 B1 | 8/2002 | Vogelstein et al. |
| 6,451,536 B1 | 9/2002 | Fodor et al. |
| 6,458,530 B1 | 10/2002 | Morris et al. |
| 6,468,744 B1 | 10/2002 | Cronin et al. |
| 6,480,791 B1 | 11/2002 | Strathmann |
| 6,489,114 B2 | 12/2002 | Laayoun et al. |
| 6,492,121 B2 | 12/2002 | Kurane et al. |
| 6,512,105 B1 | 1/2003 | Hogan et al. |
| 6,514,699 B1 | 2/2003 | O'neill et al. |
| 6,544,739 B1 | 4/2003 | Fodor et al. |
| 6,551,784 B2 | 4/2003 | Fodor et al. |
| 6,576,424 B2 | 6/2003 | Fodor et al. |
| 6,600,996 B2 | 7/2003 | Webster et al. |
| 6,629,040 B1 | 9/2003 | Goodlett et al. |
| 6,653,077 B1 | 11/2003 | Brenner |
| 6,753,147 B2 | 6/2004 | Vogelstein et al. |
| 6,787,308 B2 | 9/2004 | Balasubramanian et al. |
| 6,849,404 B2 | 2/2005 | Park et al. |
| 6,852,488 B2 | 2/2005 | Fodor et al. |
| 6,858,412 B2 | 2/2005 | Willis et al. |
| 7,155,050 B1 | 12/2006 | Sloge |
| 7,393,665 B2 | 7/2008 | Brenner |
| 7,424,368 B2 | 9/2008 | Huang et al. |
| 7,473,767 B2 | 1/2009 | Dimitrov |
| 7,476,786 B2 | 1/2009 | Chan et al. |
| 7,491,496 B2 | 2/2009 | Takuguchi et al. |
| 7,537,897 B2 | 5/2009 | Brenner et al. |
| 7,544,473 B2 | 6/2009 | Brenner |
| 7,635,566 B2 | 12/2009 | Brenner |
| 7,822,555 B2 | 10/2010 | Huang et al. |
| 7,824,856 B2 | 11/2010 | Monforte |
| 7,824,889 B2 | 11/2010 | Vogelstein et al. |
| 7,915,015 B2 | 3/2011 | Vogelstein et al. |
| 7,985,546 B2 | 7/2011 | Church et al. |
| 8,148,068 B2 | 4/2012 | Brenner |
| 8,168,385 B2 | 5/2012 | Brenner |
| 8,241,850 B2 | 8/2012 | Brenner |
| 8,298,767 B2 | 10/2012 | Brenner et al. |
| 8,318,433 B2 | 11/2012 | Brenner |
| 8,445,205 B2 | 5/2013 | Brenner |
| 8,470,996 B2 | 6/2013 | Brenner |
| 8,476,018 B2 | 7/2013 | Brenner |
| 8,481,292 B2 | 7/2013 | Casbon et al. |
| 8,486,682 B2 | 7/2013 | Loeffert |
| 8,535,889 B2 | 9/2013 | Larson et al. |
| 8,563,274 B2 | 10/2013 | Brenner et al. |
| 8,603,749 B2 | 12/2013 | Gillevet |
| 8,679,756 B1 | 3/2014 | Brenner et al. |
| 8,685,678 B2 | 4/2014 | Casbon et al. |
| 8,715,967 B2 | 5/2014 | Casbon et al. |
| 8,722,368 B2 | 5/2014 | Casbon et al. |
| 8,728,766 B2 | 5/2014 | Casbon et al. |
| 8,741,606 B2 | 6/2014 | Casbon et al. |
| 8,835,358 B2 | 9/2014 | Fodor et al. |
| 8,841,071 B2 | 9/2014 | Link |
| 8,856,410 B2 | 10/2014 | Park |
| 9,150,852 B2 | 10/2015 | Samuels et al. |
| 9,228,229 B2 | 1/2016 | Olson et al. |
| 9,290,808 B2 | 3/2016 | Fodor et al. |
| 9,290,809 B2 | 3/2016 | Fodor et al. |
| 9,315,857 B2 | 4/2016 | Fu et al. |
| 9,567,645 B2 * | 2/2017 | Fan ................... C12Q 1/6888 |
| 9,567,646 B2 | 2/2017 | Fan et al. |
| 9,582,877 B2 | 2/2017 | Fu et al. |
| 9,598,736 B2 | 3/2017 | Fan et al. |
| 9,637,799 B2 | 5/2017 | Fan et al. |
| 9,695,468 B2 | 7/2017 | Hindson |
| 9,708,659 B2 | 7/2017 | Fodor et al. |
| 9,727,810 B2 | 10/2017 | Fodor et al. |
| 9,816,137 B2 | 11/2017 | Fodor et al. |
| 9,845,502 B2 | 12/2017 | Fodor et al. |
| 9,905,005 B2 | 2/2018 | Fu et al. |
| 9,951,386 B2 | 4/2018 | Hindson et al. |
| 10,002,316 B2 | 6/2018 | Fodor et al. |
| 10,047,394 B2 | 8/2018 | Fodor et al. |
| 10,059,991 B2 | 8/2018 | Fodor et al. |
| 10,131,958 B1 | 11/2018 | Fan et al. |
| 10,151,003 B2 | 12/2018 | Fan et al. |
| 10,202,641 B2 | 2/2019 | Shum et al. |
| 10,202,646 B2 | 2/2019 | Fodor et al. |
| 10,208,356 B1 | 2/2019 | Fan et al. |
| 10,246,703 B2 | 4/2019 | Church et al. |
| 10,253,375 B1 | 4/2019 | Fan et al. |
| 10,338,066 B2 | 7/2019 | Fan |
| 10,669,570 B2 | 6/2020 | Chang |
| 10,676,779 B2 | 6/2020 | Chang |
| 10,822,643 B2 | 11/2020 | Shum et al. |
| 11,124,823 B2 | 9/2021 | Fu et al. |
| 2002/0065609 A1 | 5/2002 | Ashby |
| 2002/0072058 A1 | 6/2002 | Voelker et al. |
| 2002/0168665 A1 | 11/2002 | Okawa |
| 2002/0187480 A1 | 12/2002 | Brandon |
| 2003/0003490 A1 | 1/2003 | Fan et al. |
| 2003/0013091 A1 | 1/2003 | Dimitrov |
| 2003/0049616 A1 | 3/2003 | Brenner et al. |
| 2003/0082818 A1 | 5/2003 | Bahnson et al. |
| 2003/0104436 A1 | 6/2003 | Morris et al. |
| 2003/0175908 A1 | 9/2003 | Linnarson |
| 2003/0186251 A1 | 10/2003 | Dunn et al. |
| 2003/0207300 A1 | 11/2003 | Matray et al. |
| 2004/0047769 A1 | 3/2004 | Tanaami |
| 2004/0096368 A1 | 5/2004 | Davis |
| 2004/0096892 A1 | 5/2004 | Wang et al. |
| 2004/0121342 A1 | 6/2004 | McKeown |
| 2004/0146901 A1 | 7/2004 | Morris et al. |
| 2004/0157243 A1 | 8/2004 | Huang et al. |
| 2004/0253593 A1 | 12/2004 | Cai |
| 2004/0259118 A1 | 12/2004 | Macevicz |
| 2005/0019776 A1 | 1/2005 | Callow et al. |
| 2005/0053952 A1 | 3/2005 | Hong et al. |
| 2005/0105077 A1 | 5/2005 | Padmanabhan |
| 2005/0170373 A1 | 8/2005 | Monforte |
| 2005/0250147 A1 | 11/2005 | Macevicz |
| 2005/0287548 A1 | 12/2005 | Bao |
| 2006/0002824 A1 | 1/2006 | Chang et al. |
| 2006/0024690 A1 | 2/2006 | Kao |
| 2006/0035258 A1 | 2/2006 | Tadakamalla et al. |
| 2006/0040297 A1 | 2/2006 | Leamon et al. |
| 2006/0041385 A1 | 2/2006 | Bauer |
| 2006/0073506 A1 | 4/2006 | Christians et al. |
| 2006/0211030 A1 | 9/2006 | Brenner |
| 2006/0223122 A1 | 10/2006 | Fogo |
| 2006/0223197 A1 | 10/2006 | Vielsack |
| 2006/0234234 A1 | 10/2006 | Van Dongen |
| 2006/0246453 A1 | 11/2006 | Kato |
| 2006/0263709 A1 | 11/2006 | Matsumura et al. |
| 2006/0263789 A1 | 11/2006 | Kincaid |
| 2006/0280352 A1 | 12/2006 | Muschler et al. |
| 2006/0286570 A1 | 12/2006 | Rowlen et al. |
| 2007/0020640 A1 | 1/2007 | Mccloskey et al. |
| 2007/0259340 A1 | 1/2007 | Schramm |
| 2007/0031829 A1 | 2/2007 | Yasuno et al. |
| 2007/0042400 A1 | 2/2007 | Choi et al. |
| 2007/0042419 A1 | 2/2007 | Barany et al. |
| 2007/0065823 A1 | 3/2007 | Dressman et al. |
| 2007/0105090 A1 | 5/2007 | Cassidy et al. |
| 2007/0117121 A1 | 5/2007 | Hutchison et al. |
| 2007/0117134 A1 | 5/2007 | Kou |
| 2007/0133856 A1 | 6/2007 | Dutta-Choudhury |
| 2007/0172873 A1 | 7/2007 | Brenner et al. |
| 2007/0178478 A1 | 8/2007 | Dhallan et al. |
| 2007/0202523 A1 | 8/2007 | Becker |
| 2008/0038727 A1 | 2/2008 | Spier |
| 2008/0070303 A1 | 3/2008 | West et al. |
| 2008/0119736 A1 | 5/2008 | Dentinger |
| 2008/0194414 A1 | 8/2008 | Albert et al. |
| 2008/0261204 A1 | 10/2008 | Lexow |
| 2008/0269068 A1 | 10/2008 | Church et al. |
| 2008/0274458 A1 | 11/2008 | Latham et al. |
| 2008/0299609 A1 | 12/2008 | Kwon et al. |
| 2008/0318802 A1 | 12/2008 | Brenner |
| 2009/0061513 A1 | 3/2009 | Andersson et al. |
| 2009/0105959 A1 | 4/2009 | Braverman et al. |

(56) References Cited

U.S. PATENT DOCUMENTS

| | | |
|---|---|---|
| 2009/0137407 A1 | 5/2009 | Church et al. |
| 2009/0220385 A1 | 9/2009 | Brown |
| 2009/0226891 A2 | 9/2009 | Nova et al. |
| 2009/0252414 A1 | 10/2009 | Suzuki |
| 2009/0253586 A1 | 10/2009 | Nelson et al. |
| 2009/0283676 A1 | 11/2009 | Skoglund |
| 2009/0290151 A1 | 11/2009 | Agrawal |
| 2009/0298709 A1 | 12/2009 | Ma |
| 2010/0069250 A1 | 3/2010 | White, III et al. |
| 2010/0105049 A1 | 4/2010 | Ehrich et al. |
| 2010/0105886 A1 | 4/2010 | Woudenberg et al. |
| 2010/0120630 A1 | 5/2010 | Huang et al. |
| 2010/0159533 A1 | 6/2010 | Lipson et al. |
| 2010/0255471 A1 | 10/2010 | Clarke et al. |
| 2010/0267028 A1 | 10/2010 | Clarke |
| 2010/0291666 A1 | 11/2010 | Collier et al. |
| 2010/0300895 A1 | 12/2010 | Nobile et al. |
| 2010/0323348 A1 | 12/2010 | Hamady et al. |
| 2010/0330574 A1 | 12/2010 | Whitman et al. |
| 2011/0038507 A1 | 2/2011 | Hager |
| 2011/0059436 A1 | 3/2011 | Hardin et al. |
| 2011/0059556 A1 | 3/2011 | Strey et al. |
| 2011/0070584 A1 | 3/2011 | Wohlgemuth et al. |
| 2011/0072889 A1 | 3/2011 | Albitar et al. |
| 2011/0160078 A1 | 6/2011 | Fodor et al. |
| 2011/0201507 A1 | 8/2011 | Rava et al. |
| 2011/0230358 A1 | 9/2011 | Rava |
| 2011/0244455 A1 | 10/2011 | Larson et al. |
| 2011/0294689 A1 | 12/2011 | Namsaraev |
| 2012/0010091 A1 | 1/2012 | Linnarson |
| 2012/0014977 A1 | 1/2012 | Furihata et al. |
| 2012/0034607 A1 | 2/2012 | Rothberg |
| 2012/0045844 A1 | 2/2012 | Rothberg et al. |
| 2012/0065081 A1 | 3/2012 | Chee |
| 2012/0071331 A1 | 3/2012 | Casbon et al. |
| 2012/0087862 A1 | 4/2012 | Hood |
| 2012/0142018 A1 | 6/2012 | Jiang et al. |
| 2012/0149603 A1 | 6/2012 | Cooney |
| 2012/0156675 A1 | 6/2012 | Lueerssen et al. |
| 2012/0163681 A1 | 6/2012 | Lohse et al. |
| 2012/0165219 A1 | 6/2012 | Van Der Zaag et al. |
| 2012/0173159 A1 | 7/2012 | Davey et al. |
| 2012/0190020 A1 | 7/2012 | Oliphant et al. |
| 2012/0220022 A1 | 8/2012 | Ehrlich et al. |
| 2012/0220494 A1 | 8/2012 | Samuels et al. |
| 2012/0231972 A1 | 9/2012 | Golyshin et al. |
| 2012/0252012 A1 | 10/2012 | Armougom et al. |
| 2012/0253689 A1 | 10/2012 | Rogan |
| 2012/0316074 A1 | 12/2012 | Saxonov |
| 2012/0322681 A1 | 12/2012 | Kung et al. |
| 2013/0005585 A1 | 1/2013 | Anderson et al. |
| 2013/0022977 A1 | 1/2013 | Lapidus et al. |
| 2013/0035248 A1 | 2/2013 | Icenhour |
| 2013/0040344 A1 | 2/2013 | Ju |
| 2013/0040843 A1 | 2/2013 | Von Toerne et al. |
| 2013/0040847 A1 | 2/2013 | Thrippleton |
| 2013/0045994 A1 | 2/2013 | Shinozuka et al. |
| 2013/0190206 A1 | 7/2013 | Leonard |
| 2013/0210643 A1 | 8/2013 | Casbon et al. |
| 2013/0210659 A1 | 8/2013 | Watson et al. |
| 2013/0224743 A1 | 8/2013 | Casbon et al. |
| 2013/0225418 A1 | 8/2013 | Watson |
| 2013/0225623 A1 | 8/2013 | Buxbaum et al. |
| 2013/0237458 A1 | 9/2013 | Casbon et al. |
| 2013/0267424 A1 | 10/2013 | Casbon et al. |
| 2013/0274117 A1 | 10/2013 | Church |
| 2013/0295568 A1 | 11/2013 | Link |
| 2013/0323732 A1 | 12/2013 | Anderson et al. |
| 2014/0024032 A1 | 1/2014 | Raj |
| 2014/0057799 A1 | 2/2014 | Johnson |
| 2014/0147860 A1 | 5/2014 | Kaduchak et al. |
| 2014/0155274 A1 | 6/2014 | Xie et al. |
| 2014/0155295 A1 | 6/2014 | Hindson et al. |
| 2014/0178438 A1 | 6/2014 | Sahin et al. |
| 2014/0194324 A1 | 7/2014 | Gormley |
| 2014/0206079 A1 | 7/2014 | Malinoski |
| 2014/0206547 A1 | 7/2014 | Wang et al. |
| 2014/0216128 A1 | 8/2014 | Trotter et al. |
| 2014/0227684 A1 | 8/2014 | Hindson et al. |
| 2014/0227705 A1 | 8/2014 | Vogelstein et al. |
| 2014/0228255 A1 | 8/2014 | Hindson et al. |
| 2014/0235506 A1 | 8/2014 | Hindson et al. |
| 2014/0243242 A1 | 8/2014 | Nicol |
| 2014/0272952 A1 | 9/2014 | May et al. |
| 2014/0274811 A1 | 9/2014 | Arnold |
| 2014/0287963 A1 | 9/2014 | Hindson et al. |
| 2014/0303005 A1 | 10/2014 | Samuels et al. |
| 2014/0309945 A1 | 10/2014 | Park et al. |
| 2014/0315211 A1 | 10/2014 | Sugino et al. |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005199 A1 | 1/2015 | Hindson et al. |
| 2015/0005200 A1 | 1/2015 | Hindson et al. |
| 2015/0017652 A1 | 1/2015 | Robins et al. |
| 2015/0066385 A1 | 3/2015 | Schnall-levin et al. |
| 2015/0118680 A1 | 4/2015 | Fodor et al. |
| 2015/0119255 A1 | 4/2015 | Fodor et al. |
| 2015/0119256 A1 | 4/2015 | Fodor et al. |
| 2015/0119257 A1 | 4/2015 | Fodor et al. |
| 2015/0119258 A1 | 4/2015 | Fodor et al. |
| 2015/0119290 A1 | 4/2015 | Fodor et al. |
| 2015/0133319 A1 | 5/2015 | Fu et al. |
| 2015/0203897 A1 | 7/2015 | Robins et al. |
| 2015/0225778 A1 | 8/2015 | Hindson et al. |
| 2015/0247182 A1 | 9/2015 | Faham et al. |
| 2015/0259734 A1 | 9/2015 | Asbury et al. |
| 2015/0298091 A1 | 10/2015 | Weitz et al. |
| 2015/0307874 A1 | 10/2015 | Jaitin et al. |
| 2015/0329852 A1 | 11/2015 | Nolan |
| 2015/0376609 A1 | 12/2015 | Hindson et al. |
| 2016/0026758 A1 | 1/2016 | Jabara et al. |
| 2016/0122753 A1 | 5/2016 | Mikkelsen et al. |
| 2016/0208322 A1 | 7/2016 | Anderson et al. |
| 2016/0244828 A1 | 8/2016 | Mason |
| 2016/0257993 A1 | 9/2016 | Fu et al. |
| 2016/0289669 A1 | 10/2016 | Fan et al. |
| 2016/0289670 A1 | 10/2016 | Samuels |
| 2016/0289740 A1 | 10/2016 | Fu et al. |
| 2016/0312276 A1 | 10/2016 | Fu et al. |
| 2016/0320720 A1 | 11/2016 | Fan et al. |
| 2016/0376648 A1 | 12/2016 | Fodor et al. |
| 2017/0073730 A1 | 3/2017 | Betts et al. |
| 2017/0342405 A1 | 11/2017 | Fu et al. |
| 2017/0344866 A1 | 11/2017 | Fan et al. |
| 2018/0002738 A1 | 1/2018 | Wang et al. |
| 2018/0002764 A1 | 1/2018 | Fan et al. |
| 2018/0037942 A1 | 2/2018 | Fu et al. |
| 2018/0088112 A1 | 3/2018 | Fan |
| 2018/0251825 A1 | 9/2018 | Stoeckius |
| 2018/0258500 A1 | 9/2018 | Fan et al. |
| 2018/0291470 A1 | 10/2018 | Fan et al. |
| 2018/0327835 A1 | 11/2018 | Fodor et al. |
| 2019/0100798 A1 | 4/2019 | Fodor et al. |
| 2019/0119726 A1 | 4/2019 | Shum et al. |
| 2019/0323088 A1 | 10/2019 | Boutet |
| 2020/0002766 A1 | 1/2020 | Genolet |
| 2020/0224247 A1 | 7/2020 | Lazaruk |
| 2020/0255888 A1 | 8/2020 | Jensen |

FOREIGN PATENT DOCUMENTS

| | | |
|---|---|---|
| EP | 1 473 080 | 11/2004 |
| EP | 1 647 600 | 4/2006 |
| EP | 1 845 160 | 10/2007 |
| EP | 2 541 250 | 1/2013 |
| EP | 2 623 613 | 8/2013 |
| EP | 2 805 769 | 11/2014 |
| JP | 2005-233974 | 9/2005 |
| JP | 2008-256428 | 10/2008 |
| JP | 2013-039275 | 2/2013 |
| WO | WO 89/01050 | 2/1989 |

(56) References Cited

FOREIGN PATENT DOCUMENTS

| | | |
|---|---|---|
| WO | WO 96/24061 | 8/1996 |
| WO | WO 97/10365 | 3/1997 |
| WO | WO 99/15702 | 4/1999 |
| WO | WO 99/28505 | 6/1999 |
| WO | WO 00/58516 | 10/2000 |
| WO | WO 02/056014 | 7/2002 |
| WO | WO 02/059355 | 8/2002 |
| WO | WO 02/070684 | 9/2002 |
| WO | WO 04/017374 | 2/2004 |
| WO | WO 05/042759 | 5/2005 |
| WO | WO 05/071110 | 8/2005 |
| WO | WO 05/080604 | 9/2005 |
| WO | WO 05/111242 | 11/2005 |
| WO | WO 06/071776 | 7/2006 |
| WO | WO 06/102264 | 9/2006 |
| WO | WO 06/116127 | 11/2006 |
| WO | WO 07/087310 | 8/2007 |
| WO | WO 07/087312 | 8/2007 |
| WO | WO 07/147079 | 12/2007 |
| WO | WO 08/096318 | 8/2008 |
| WO | WO 08/147428 | 12/2008 |
| WO | WO 08/150432 | 12/2008 |
| WO | WO 09/148560 | 12/2009 |
| WO | WO 09/152928 | 12/2009 |
| WO | WO 10/030818 | 3/2010 |
| WO | WO 10/117620 | 10/2010 |
| WO | WO 11/123246 | 10/2011 |
| WO | WO 11/143659 | 11/2011 |
| WO | WO 11/155833 | 12/2011 |
| WO | WO 12/038839 | 3/2012 |
| WO | WO 12/042374 | 4/2012 |
| WO | WO 12/047297 | 4/2012 |
| WO | WO 12/048341 | 4/2012 |
| WO | WO 12/083225 | 6/2012 |
| WO | WO 12/108864 | 8/2012 |
| WO | WO 12/129363 | 9/2012 |
| WO | WO 12/140224 | 10/2012 |
| WO | WO 12/142213 | 10/2012 |
| WO | WO 12/148477 | 11/2012 |
| WO | WO 12/149042 | 11/2012 |
| WO | WO 12/162267 | 11/2012 |
| WO | WO 13/019075 | 2/2013 |
| WO | WO 13/117595 | 8/2013 |
| WO | WO 13/130674 | 9/2013 |
| WO | WO 13/148525 | 10/2013 |
| WO | WO 13/173394 | 11/2013 |
| WO | WO 13/176767 | 11/2013 |
| WO | WO 13/177206 | 11/2013 |
| WO | WO 13/188831 | 12/2013 |
| WO | WO 13/188872 | 12/2013 |
| WO | WO 13/191775 | 12/2013 |
| WO | WO 14/015084 | 1/2014 |
| WO | WO 14/015098 | 1/2014 |
| WO | WO 14/018460 | 1/2014 |
| WO | WO 14/028537 | 2/2014 |
| WO | WO 14/071361 | 5/2014 |
| WO | WO 14/093676 | 6/2014 |
| WO | WO 14/108850 | 7/2014 |
| WO | WO 14/124336 | 8/2014 |
| WO | WO 14/124338 | 8/2014 |
| WO | WO 14/126937 | 8/2014 |
| WO | WO 14/144495 | 9/2014 |
| WO | WO 14/201273 | 12/2014 |
| WO | WO 14/210353 | 12/2014 |
| WO | WO 15/002908 | 1/2015 |
| WO | WO 15/035087 | 3/2015 |
| WO | WO 2015/031691 A1 * | 3/2015 |
| WO | WO 15/044428 | 4/2015 |
| WO | WO 15/047186 | 4/2015 |
| WO | WO 15/103339 | 7/2015 |
| WO | WO 15/134787 | 9/2015 |
| WO | WO 15/200869 | 12/2015 |
| WO | WO 16/044227 | 3/2016 |
| WO | WO 16/118915 | 7/2016 |
| WO | WO 16/138496 | 9/2016 |
| WO | WO 16/138500 | 9/2016 |
| WO | WO 16/149418 | 9/2016 |
| WO | WO 16/160844 | 10/2016 |
| WO | WO 17/079593 | 5/2017 |
| WO | WO 17/205691 | 11/2017 |
| WO | WO 18/089377 | 5/2018 |

OTHER PUBLICATIONS

Algae, Wikipedia.org, accessed Mar. 4, 2016, 20 pp.
Alkan et al., Oct. 2009, Personalized copy number and segmental duplication maps using next-generation sequencing. Nat Genet., 41(10):1061-1067.
Anderson, Feb. 11, 2014, Study describes RNA sequencing applications for molecular indexing methods, genomeweb.com, 5 pp.
Ansorge, 2009, Next-generation DNA sequencing techniques. New Biotechnology, 25(4):195-203.
Applied Biosystems, Apr. 2008, SOLID™ System Barcoding, Application Note, 4 pp.
Archaea, Wikipedia.org, accessed May 11, 2016, 26 pp.
Atanur et al., Jun. 2010, The genome sequence of the spontaneously hypertensive rat: Analysis and functional significance. Genome Res., 20(6):791-803.
Audic et al., 1997, The Significance of Digital Gene Expression Profiles. Genome Research, 7:986-995.
Begley Jun. 20, 2017, Psst, the human genome was never completely sequenced. STAT News, 7 pp.
Bendall et al., May 6, 2011, Single-cell mass cytometry of differential immune and drug responses across a human hematopoietic continuum. Science, 332(6030):687-696.
Bionumbers, Aug. 21, 2010, Useful fundamental numbers in molecular biology, http:/bionumbers.hms.harvard.edu/KeyNumbers/aspx, 4 pp.
Bioscribe, Feb. 5, 2015, Massively parallel sequencing technology for single-cell gene expression published (press release), 3 pp.
Blainey, May 2013, The future is now: single-cell genomics of bacteria and archaea, FEMS Microbiol Rev., 37(3):407-427.
Bogdanova et al., Jan. 2008, Normalization of full-length enriched cDNA, Molecular Biosystems, 4(3):205-212.
Bonaldo et al., Sep. 1996, Normalization and subtraction: two approaches to facilitate gene discovery. Genome Res., 6(9):791-806.
Bontoux et al, "Integrating whole transcriptome assays on a lab-on-a-chip for single cell gene profiling", Lab on a Chip, (2008) vol. 8, No. 3, pp. 443-450.
Bose et al., Jun. 6, 2015, Scalable microfluidics for single-cell RNA printing and sequencing, Genome Biology, 16(1):120.
Brady et al., "Construction of cDNA libraries form single cells", Methods in Enzymology, Academic Press, US, (1993) vol. 225, doi: 10.1016/0076-6879(93)25039-5, ISSN 0076-6879, pp. 611-623.
Braha et al., 2000, Simultaneous stochastic sensing of divalent metal ions. Nature Biotechnology, 18:1005-1007.
Bratke et al., Sep. 2005, Differential expression of human granzymes A, B, and K in natural killer cells and during CD8+ T cell differentiation in peripheral blood. Eur J Immunol., 35(9):2608-2616.
Brenner et al., 2000, Gene expression analysis by massively parallel signature sequencing (MPSS) on microbead arrays. Nature Biotechnology, 18:630-634.
Brenner et al., Feb. 15, 2000, In vitro cloning of complex mixtures of DNA on microbeads: physical separation of differentially expressed cDNAs. Proc Natl Acad Sci, 97(4):1665-1670.
Brinza et al., Apr. 16-20, 2016, Detection of somatic mutations at 0.1% frequency from cfDNA in peripheral blood with a multiplex next-generation sequencing assay, conference poster, AACR 107th Annual Meeting. 1 p.
Brisco et al., Jun. 25, 2012, Quantification of RNA integrity and its use for measurement of transcript number, Nucleic Acids Research, 40(18):e144.
Brodin et al., 2015, Challenges with using primer IDs to improve accuracy of next generation sequencing. PLoS One, 19(3):1-12.

(56) References Cited

OTHER PUBLICATIONS

Buschmann et al., Aug. 7, 2014, Enhancing the detection of barcoded reads in high throughput DNA sequencing DNA by controlling the false discovery rate, BMC Bioinformatics, 15(1):264.
Butkus, Feb. 6, 2014, Cellular research set to launch first gene expression platform using 'molecular indexing' technology, genomeweb.com, 5 pp.
Bystrykh, May 17, 2012, Generalized DNA barcode design based on hamming codes, PLoS One, 7(5):E36852.
Cai, Mar. 2013, Turning single cells in microarrays by super-resolution bar-coding, Brief Funct Genomics, 12(2):75-80.
Carr et al., Dec. 15, 2009, Inferring relative proportions of DNA variants from sequencing electropherograms. Bioinformatics, 25(24):3244-3250.
Caruccio et al., Oct. 2009, Nextera™ technology for NGS DNA library preparation: simultaneous fragmentation and tagging by in vitro transposition, 16(3), 3 pp.
Casbon et al., Jul. 2011, A method for counting PCR template molecules with application to next-generation sequencing. Nucleic Acids Res., 39(12):881.
Castellarnau et al., Jan. 2015, Stochastic particle barcoding for single-cell tracking and multiparametric analysis, Small, 11(4):489-498.
Castle et al., Apr. 16, 2010, DNA copy number, including telomeres and mitochondria, assayed using next-generation sequencing. BMC Genomics, 11:244. doi: 10.1186/1471-2164-11-244.
Chamberlain et al., Dec. 9, 1988, Deletion screening of the Duchenne muscular dystrophy locus via multiplex DNA amplification. Nucleic Acids Res., 16(23):11141-11156.
Chang et al., Aug. 2002, Detection of allelic imbalance in ascitic supernatant by digital single nucleotide polymorphism analysis. Clin Cancer Res., 8(8):2580-2585.
Chee et al., 1996, Accessing genetic information with high-density DNA arrays, Science, 274:610-614.
Chee, 1991, Enzymatic multiplex DNA sequencing. Nucleic Acids Research, 19(12): 3301-3305.
Chen et al., Apr. 9, 2015, Spatially resolved, highly multiplexed RNA profiling in single cells. Science Express, pp. 1-21.
Church et al., 1988, Multiplex DNA sequencing. Science, 240:185-188.
Clontech Laboratories, Inc., May 15, 2007, Super SMART™ PCR cDNA Synthesis Kit User Manual, 39 pp.
Cloonan et al., "Stem cell transcriptome profiling via massive-scale mRNA sequencing", Nature Methods, (Jul. 2008) vol. 5, No. 7, pp. 613-619.
Costa et al., Aug. 22, 2012, Single-tube nested real-time PCR as a new highly sensitive approach to trace hazelnut, J. Agric Food Chem, 60(33):8103-8110.
Costello et al., Apr. 1, 2013, Discovery and characterization of artefactual mutations in deep coverage targeted capture sequencing data due to oxidative DNA damage during sample preparation. Nucleic Acids Res, 41(6):e67.
Cox, May 2001, Bar coding objects with DNA, Analyst, 126(5):545-547.
Craig et al., Oct. 2008, Identification of genetic variants using bar-coded multiplexed sequencing. Nat Methods, 5(10):887-893.
Cusanovich et al., May 7, 2014, Multiplex single-cell profiling of chromatin accessibility by combinatorial cellular indexing. Science Express, pp. 1-9.
Custom Antibody Services, Precision Antibody, accessed Apr. 16, 2014, 2 pp.
Daines et al., Aug. 2009, High-throughput multiplex sequencing to discover copy number variants in *Drosophila*. Genetics, 182(4):935-941.
Dalerba et al., 2011, Single-cell dissection of transcriptional heterogeneity in human colon tumors, Nat Biotechnol., 29(12):1120-1127 and Supplementary Material.
D'Antoni et al., May 1, 2006, Rapid quantitative analysis using a single molecule counting approach. Anal Biochem. 352(1):97-109.

Daser et al., 2006, Interrogation of genomes by molecular copy-number counting (MCC). Nature Methods, 3(6):447-453.
De Saizieu et al., 1998, Bacterial transcript imaging by hybridization of total RNA to oligonucleotide arrays. Nature Biotechnology, 16:45-48.
Di Carlo et al., Dec. 1, 2008, Dynamic single-cell analysis for quantitative biology, Analytical Chemistry, 78(23):7918-7925.
Dirks et al., Oct. 26, 2004, Triggered amplification by hybridization chain reaction., Proc Natl Acad Sci U S A, 101(43), 15275-15278.
Eberwine et al., "Analysis of gene expression in single live neurons", Proc. Nati. Acad. Sci. USA, (Apr. 1992) vol. 89, No. 7. pp. 3010-3014.
Evanko, 2004, Hybridization chain reactions Nature Methods, 1:186.
Fan et al., 2000, Parallel Genotyping of Human SNPs Using Generic High-density Oligonucleotide Tag Arrays. Genome Research, 10:853-860.
Fan et al., 2009, Microfluidic digital PCR enables rapid prenatal diagnosis of fetal aneuploidy. Am Obstet Gynecol. 200:543.e1-543.87.
Fan et al., Feb. 6, 2015, Combinatorial labeling of single cells for gene expression cytometry. Science, 347(6222):1258367-8.
Fan et al., Jul. 19, 2012, Non-invasive prenatal measurement of the fetal genome. Nature, 487(7407):320-324.
Fan, Nov. 2010, Molecular counting: from noninvasive prenatal diagnostics to whole-genome haplotyping, doctoral dissertation, Stanford University, 185 pp.
Feldhaus et al., Jan. 15, 2000, Oligonucleotide-conjugated beads for transdominant genetic experiments, Nucleic Acids Res., 28(2):534-543.
Fish, Wikipedia.org, accessed Nov. 2, 2014, 11 pp.
Fox-Walsh et al., Oct. 2011, A multiplex RNA-seq strategy to profile poly(A+) RNA: application to analysis of transcription response and 3' end formation., Genomics, 98(4),266-271.
Fu et al., Feb. 4, 2014, Molecular indexing enables quantitative targeted RNA sequencing and reveals poor efficiencies in standard library preparations, PNAS, 111(5):1891-1896.
Fu et al., Mar. 18, 2014, Digital encoding of cellular mRNAs enabling precise and absolute gene expression measurement by single-molecule counting. Anal Chem., 86(6):2867-2870.
Fu et al., May 31, 2011, Counting individual DNA molecules by the stochastic attachment of diverse labels. Proc Natl Acad Sci, 108(22):9026-9031.
Fungus, Wikipedia.org, accessed Jun. 3, 2013, 28 pp.
Gerry et al., 1999, Universal DNA microarray method for multiplex detection of low abundance point mutations. Journal of Molecular Biology, 292(2): 251-262.
Gillespie, 1977, Exact stochastic simulation of coupled chemical reactions. The Journal of Physical Chemistry, 81(25):2340-2361.
Gong et al., 2010, Massively parallel detection of gene expression in single cells using subnanolitre wells, Lab Chip, 10:2334-2337.
Grant et al., Nov. 15, 2002, SNP genotyping on a genome-wide amplified DOP-PCR template. Nucleic Acids Res, 30(22):e125.
Gu et al., Apr. 16-20, 2016, Complete workflow for detection of low frequency somatic mutations from cell-free DNA using Ion Torrent™ platforms, conference poster, AACR 107th Annual Meeting, 1 p.
Gunderson et al., May 2004, Decoding randomly ordered DNA arrays. Genome Res. 14(5):870-877.
Gundry et al., Jan. 3, 2012, Direct mutation analysis by high-throughput sequencing: from germline to low-abundant, somatic variants. Mutat Res. 729(1-2):1-15.
Gundry et al., Mar. 2012, Direct, genome-wide assessment of DNA mutations in single cells. Nucleic Acids Res., 40(5):2032-40.
Hacia et al., 1999, Determination of ancestral alleles for human single-nucleotide polymorphisms using high-density oligonucleotide arrays. Nature Genetics, 22:164-167.
Haff, 1994, Improved quantitative PCR using nested primers, PCR Methods and Applications, 3:332-337.
Hamady et al., Mar. 2008, Error-correcting barcoded primers for pyrosequencing hundreds of samples in multiplex. Nat Methods, 5(3):235-237.
Harbers, "The current status of cDNA cloning", Genomics, (2008) vol. 91, No. 3, pp. 232-242.

(56) References Cited

OTHER PUBLICATIONS

Harrington et al., 2009, Cross-sectional characterization of HIV-1 env compartmentalization in cerebrospinal fluid over the full disease course, AIDS, 23(8) 907-915.
Hartmann, "Gene expression profiling of single cells on large-scale oligonucleotide arrays", Nucleic Acids Research, (Oct. 2006) vol. 34, No. 21, p. e143.
Hashimshony et al., Sep. 27, 2012, CEL-Seq: single-cell RNA-Seq by multiplexed linear amplification Cell Rep. 2(3):666-673.
Hensel et al., Jul. 21, 1995, Simultaneous identification of bacterial virulence genes by negative selection. Science, 269(5222):400-403.
Herne et al., Jan. 1997, Characterization of DNA probes immobilized on gold surfaces, Journal of American Chemical Society, 119:8916-8920.
Hiatt et al., Feb. 2010, Parallel, tag-directed assembly of locally derived short sequence reads. Nat Methods, 7(2):119-122.
Hiatt et al., May 2013, Single molecule molecular inversion probes for targeted, high-accuracy detection of low-frequency variation. Genome Res., 23(5):843-854.
Hollas et al., 2003, A stochastic approach to count RNA molecules using DNA sequencing methods. Lecture Notes in Computer Science, 2812:55-62.
How many species of bacteria are there? Wisegeek.org, accessed Jan. 21, 2014, 2 pp.
Hug et al., 2003, Measure of the number of molecular of a single mRNA species in a complex mRNA preparation, Journal of Theoretical Biology, 221:615-624.
Ingolia et al., Apr. 10, 2009, Genome-wide analysis in vivo of translation with nucleotide resolution using ribosome profiling. Science, 324(5924):218-223.
Islam et al., "Highly multiplexed and strand specific single-cell RNA 5' end sequencing", Nature Protocols, (2012) vol. 7, No. 5, pp. 813-828.
Islam et al., 2011, Characterization of the single-cell transcriptional landscape by highly multiplex RNA-seq. Genome Research, 21:1160-1167.
Islam et al., 2014, Quantitative single-cell RNA-seq with unique molecular identifiers, Nature Methods, 11(2):163-168.
Jabara et al., Dec. 3, 2011, Accurate sampling and deep sequencing of the HIV-1 protease gene using a Primer ID, PNAS, 108(50):20166-20171.
Jabara, Apr. 23, 2010, Capturing the cloud: High throughput sequencing of multiple individual genomes from a retroviral population. Biology Lunch Bunch Series, Training Initiatives in Biomedical & Biological Sciences of the University of North Carolina at Chapel Hill.
Jiang et al., 2011, Synthetic spike-in standards for RNA-seq experiments, Genome Research, 21(9):1543-1551.
Junker et al., May 21, 2015, Single-cell transcriptomics enters the age of mass production, Molecular Cell, 58:563-564.
Kanagawa, 2003, Bias and artifacts in multitemplate polymerase chain reactions (PCR), Journal of Bioscience and Bioengineering, 96(4):317-323.
Karrer et al., "In situ isolation of mRNA from individual plant cells: creation of cell-specific cDNA libraries.", Proc. Natl. Acad. Sci. USA, (Apr. 1995) vol. 92, No. 9, pp. 3614-3618.
Kebschull et al., Jul. 17, 2015, Sources of PCR-induced distortions in high-throughput sequencing data sets, Nucleic Acids Research, 15 pp.
Keys et al., Jun. 2015, Primer ID informs next-generation sequencing platforms and reveals preexisting drug resistance mutations in the HIV-1 reverse transcriptase coding domain, AIDS Research and Human Retroviruses, 31(6):658-668.
Kim et al., Jun. 8, 2007, Polony multiplex analysis of gene expression (PMAGE) in mouse hypertrophic cardiomyopathy, Science, 316(5830):1481-1484.
Kinde et al., Jun. 7, 2011, Detection and quantification of rare mutations with massively parallel sequencing, Proc. Natl Acad Sci, 108(23):9530-0535.

Kivioja et al., Jan. 2012, Counting absolute numbers of molecules using unique molecular identifiers. Nature Methods, 9(1):72-76.
Klein et al., May 21, 2015, Droplet barcoding for single-cell transcriptomics applied to embryonic stem cells, Cell, 161:1187-1201.
Ko et al., "RNA-conjugated template-switching RT-PCR method for generating an *Escherichia coli* cDNA library for small RNAs", Journal of Microbiological Methods, (2006) vol. 64, No. 3, pp. 297-304.
Koboldt et al., Sep. 1, 2009, VarScan: variant detection in massively parallel sequencing of individual and pooled samples. Bioinformatics. 25(17):2283-2285.
Kolodziejczyk et al., May 21, 2015, The technology and biology of single-cell RNA sequencing, Molecular Cell, 58:610-620.
Konig et al., Jul. 2010, iCLIP reveals the function of hnRNAP particles in splicing at individual nucleotide resolution, Nature Structural & Molecular Biology, 17(7):909-916.
Kotake et al., 1996, A simple nested RT-PCR method for quantitation of the relative amounts of multiple cytokine mRNAs in small tissue samples, Journal of Immunological Methods, 199:193-203.
Kurimoto et al., "Global single-cell cDNA amplification to provide a template for representative high-density oligonucleotide microarray analysis", Nature Protocols, (2007) vol. 2, No. 3, pp. 739-752.
Kurimoto et al., Mar. 17, 2006, An improved single-cell cDNA amplification method for efficient high-density oligonucleotide microarray analysis, Nucleic Acids Res., 34(5):e42.
Lamble et al., Nov. 20, 2013, Improved workflows for high throughput library preparation using the transposome-based nextera system, BMC Biotechnology, 13(1):104.
Larson et al., Nov. 2009, A single molecule view of gene expression. Trends Cell Biol. 19(11):630-637.
Leamon et al., Nov. 2003, A massively parallel PicoTiterPlate based platform for discrete picoliter-scale polymerase chain reactions, Electrophoresis, 24(21):3769-3777.
Lee et al., 2010, Large-scale arrays of picolitre chambers for single-cell analysis of large cell populations, Lab Chip, 10:2952-2958.
Lee et al., Mar. 21, 2014, Highly multiplexed subcellular RNA sequencing in situ. Science. 343(6177):1360-1363.
Lin et al., Feb. 2007, Self-assembled combinatoral encoding nanoarrays for multiplexed biosensing, Nano Letters, 7(2):507-512.
List of sequenced bacterial genomes, Wikipedia.org, accessed Jan. 24, 2014, 57 pp.
Liu et al., Single-cell transcriptome sequencing: recent advances and remaining challenges, F1000Research 2016, 5(F1000 Faculty Rev):182, 9 pp.
Lizardi et al., Jul. 1998, Mutation detection and single-molecule counting using isothermal rolling-circle amplification. Nat Genet. 19(3):225-32.
Lockhart et al., 1996, Expression monitoring by hybridization to high-density oligonucleotide arrays. Nature Biotechnology, 14:1675-1680.
Lovatt et al., Feb. 2014, Transcriptome in vivo analysis (TIVA) of spatially defined single cells in live tissue. Nat Methods. 11(2):190-196.
Loy et al., Oct. 2, 2018, A rapid library preparation method with custom assay designs for detection of variants at 0.1% allelic frequency in liquid biopsy samples, undated, 1 p.
Lucito et al., 1996, Representational Oligonucleotide Microarray Analysis: A High-Resolution Method to Detect Genome Copy Number Variation. Genome Research, 13: 2291-2305.
Maamar et al., 2007, Noise in Gene Expression Determines Cell Fate in Bacillus subtilis. Science, 317:526-529.
Macaulay et al., 2015, G&T-seq: parallel sequencing of single-cell genomes and transcriptomes. Nature Methods, pp. 1-7.
Macosko et al., 2015, Highly parallel genome-wide expression profiling of individual cells using nanoliter droplets, Cell 161:1202-1214 (and supplemental information).
Maeda et al., "Development of a DNA barcode tagging method for monitoring dynamic changes in gene expression by using an ultra high-throughput sequencer", BioTechniques, (Jul. 2008), vol. 45, No. 1, pp. 95-97.

(56) References Cited

OTHER PUBLICATIONS

Makrigiorgos et al., Sep. 2002, A PCR-Based amplification method retaining quantities difference between two complex genomes. Nature Biotech, 20(9):936-939.
Mammal, Wikipedia.org, accessed Sep. 22, 2011, 16 pp.
Marcus et al., 2006, Microfluidic single-cell mRNA isolation and analysis, Ana. Chem. 78:3084-3089.
Mardis, "Next-generation DNA sequencing methods", Annu. Rev. Genomics Hum. Genet., (2008) vol. 9, pp. 387-402.
Marguerat et al, "Next-generation sequencing: applications beyond genomes", Biochemical Society Transactions, (2008) vol. 36, No. 5, pp. 1091-1096.
Margulies et al., Sep. 15, 2005 Genome sequencing in microfabricated high-density picolitre reactors, Nature, 437:376-380.
Martinez et al., Jul. 2012, A microfluidic approach to encapsulate living cells in uniform alginate hydrogel microparticles, Macromol. Biosci, 12(7):946-951.
Massachusetts General Hospital, Overview of Illumina Chemistry, http://nextgen.mgh.harvard.edu/IlluminaChemistry.html, downloaded Dec. 31/2018, 2 pp.
McCloskey et al., Dec. 2007, Encoding PCR products with batch-stamps and barcodes. Biochem Genet. 45(11-12):761-767.
Medvedev et al., Nov. 2010, Detecting copy number variation with mated short reads. Genome Res. 20(11):1613-1622.
Mei et al., Mar. 22, 2010, Identification of recurrent regions of Copy-Number Variants across multiple individuals. BMC Bioinformatics. 11:147.
Merriam-Webster, definition of associate,: http://www.merriam-webster.com/dictionary/associate, accessed Apr. 5, 2016.
Meyer et al., "Parallel tagged sequencing on the 454 platform", Nature Protocols, (2008) vol. 3, No. 2, pp. 267-278.
Miller et al., 2006, Directed evolution by in vitro compartmentalization, Nature Methods, 3:561-570.
Miner et al., 2004, Molecular barcodes detect redundancy and contamination in hairpin-bisulfite PCR. Nucleic Acids Research, 32(17):e135.
Mortazavi et al., 2008, Mapping and quantifying mammalian transcriptomes by RNA-Seq. Nat. Methods. 5:621-628.
Muller et al., Oct. 17, 2018, Genome organization and DNA accessibility control antigenic variation in trypanosomes, Nature, 563(7729):121-125.
Murinae, Wikipedia.org, accessed Mar. 18, 2013, 21 pp.
Nadai et al., 2008, Protocol for nearly full-length sequencing of HIV-1 RNA from plasma, PLoS One, 3(1):e1420.
Nagai et al., 2001, Development of a microchamber array for picoleter PCR, Anal. Chem., 73:1043-1047.
Navin et al., 2015, The first five years of single-cell cancer genomics and beyond, Genome Research, 25(10):1499-1507.
Newell et al., Jan. 27, 2012, Cytometry by time-of-flight shows combinatorial cytokine expression and virus-specific cell niches within a continuum of CD8+ T cell phenotypes. Immunity. 36(1):142-152.
Novak et al., Jan. 20, 2011, Single-cell multiplex gene detection and sequencing with microfluidically generated agarose emulsions, Angew Chem Int Ed Engl., 50(2):390-395.
Ogino et al., Nov. 2002, Quantification of PCR bias caused by a single nucleotide polymorphism in SMN gene dosage analysis. J Mol Diagn. 4(4):185-190.
Ozkumur et al., Apr. 3, 2013, Inertial focusing for tumor antigen-dependent and -independent sorting of rare circulating tumor cells, Sci Transl Med, 5(179):1-20.
Parameswaran et al., 2007, A pyrosequencing-tailored nucleotide barcode design unveils opportunities for large-scale sample multiplexing. Nucleic Acids Res. 35(19):e130.
Park et al., May 2010, Discovery of common Asian copy number variants using integrated high-resolution array CGH and massively parallel DNA sequencing. Nat Genet. 42(5):400-405.
Patanjali et al., Mar. 1991, Construction of a uniform-abundance (normalized) CNDA library, Proceedings of the National Academy of Sciences, 88(5):1943-1947.

Peng et al., Mar. 11, 2016, Reducing amplification artifacts in high multiplex amplicon sequencing by using molecular barcodes, BMC Genomics, retrieved from the internet: url:http://bmcgenomics.biomedcentral.com/articles/0.1186/s12864-015-1806-8, 14 pp.
Peters et al., Jan. 14, 2015, Co-barcoded sequence reads from long DNA fragments: a cost-effective solution for "perfect genome" sequencing. Frontiers in Genetics, 5(Article 466)1-8.
Pfaffi et al., Mar. 2004, Determination of stable housekeeping genes, differentially regulated target genes and sample integrity: BestKeeper—Excel-based tool using pair-wise correlations, Biotechnology Letters, 26(6):505-515.
Picelli et al., Jul. 30, 2014, Tn5 transposase and tagmentation procedures for massively scaled sequencing projects, Genome Research 24(12):2033-2040.
Pihlak et al., 2008, Rapid genome sequencing with short universal tiling probes. Nature Biotechnology, 26:676-684.
Pinkel et al., 2005, Comparative Genomic Hybridization. Annual Review of Genomics and Human Genetics, 6:331-354.
Plant, Wikipedia.org, accessed Aug. 28, 2015, 14 pp.
Pleasance et al., Jan. 14, 2010, A small-cell lung cancer genome with complex signatures of tobacco exposure. Nature. 463(7278):184-190.
Plessy et al., Feb. 2013, Population transcriptomics with single-cell resolution: a new field made possible by microfluidics: a technology for high throughput transcript counting and data-driven definition of cell types, Bioessays, 35(2):131-140.
Poole et al., 2007, Measuring global gene expression in polyploidy; a cautionary note from allohexaploid wheat, Funct. Integr Genomics, 7:207-219.
Protozoa, Wikipedia.org, accessed May 11, 2016, 10 pp.
Qiu et al., Oct. 2003, DNA sequence-based "bar codes" for tracking the origins of expressed sequence tags from a maize cDNA library constructed using multiple mRNA sources. Plant Physiol. 133(2):475-481.
Rajeevan et al., Oct. 2003, Global amplification of sense RNA: a novel method to replicate and archive mRNA for gene expression analysis, Genomics, 82(4):491-497.
Robinson et al., 2010, A scaling normalization method for differential expression analysis of RNA-seq data, Genome Biology, vol. 11, 9 pp.
Roche Diagnostics GmbH, 2006, Genome Sequencer 20 System: First to the Finish (product brochure), 40 pp.
Sasagawa et al., 2013, Quartz-Seq: a highly reproducible and sensitive single-cell RNA sequencing method, reveals non-genetic gene expression heterogeneity. Genome Biology, 14:R31.
Sasuga et al., Dec. 2008, Single-cell chemical lysis method for analyses of intracellular molecules using an array of picoliter-scale microwells, Anal Chem, 80(23):9141-9149.
Satija et al., May 2015, Spatial reconstruction of single-cell gene expression data. Nature Biotechnology, 33(5):495-508.
Schmitt et al., Sep. 4, 2012, Detection of ultra-rare mutations by next-generation sequencing. Proc Natl Acad Sci U S A. 109(36):14508-14513.
Sebat et al., 2004, Large-Scale Copy Number Polymorphism in the Human Genome. Science, 305:525-528.
Shalek et al., Jun. 13, 2013, Single-cell transcriptomics reveals bimodality in expression and splicing in immune cells. Nature. 498(7453):236-240.
Shendure et al., "Next-generation DNA sequencing", Nature Biotechnology, (Oct. 2008) vol. 26, No. 10, pp. 1135-1145.
Shiroguchi et al., Jan. 24, 2012, Digital RNA sequencing minimizes sequence-dependent bias and amplification noise with optimized single-molecule barcodes. Proc Natl Acad Sci U S A. 109(4):1347-1352.
Shoemaker et al., 1996, Quantitative phenotypic analysis of yeast deletion mutants using a highly parallel molecular bar-coding strategy. Nature Genetics, 14:450-456.
Shortreed et al., Sep. 2, 2005, A thermodynamic approach to designing structure-free combinatorial DNA word sets, Nucleic Acids Research, 33(15):4965-4977.

(56) References Cited

OTHER PUBLICATIONS

Siegel et al., Apr. 12, 2010, Genome-wide analysis of mRNA abundance in two life-cycle stages of trypanosoma brucei and identification of splicing and polyadenylation sites, Nucleic Acids Research, 38(15):4946-4957.

Simpson et al., Feb. 15, 2010, Copy number variant detection in inbred strains from short read sequence data. Bioinformatics. 26(4):565-567.

Smith et al., 2010, Highly-multiplexed barcode sequencing: an efficient method for parallel analysis of pooled samples. Nucleic Acids Research, 38(13):e142.

Sogin et al., 2006, Microbilal diversity in the deep sea and the underexplored "rare biosphere," PNAS, 103:12115-12120.

Solomatin et al., 2009, Methods of site-specific labling of NRA with fluorescent dyes, Methods in Enzymology, vol. 469, 22 pp.

Sommer et al., Nov. 16, 1989, Minimal homology requirements for PCR primers, Nucleic Acids Research, 17(16):6749.

Song et al., 2013, Design rules for size-based cell sorting and sheathless cell focusing by hydrophoresis, Journal of Chromatography A, 1302:191-196.

Soumillon et al., Mar. 5, 2014, Characterization of directed differentiation by high-throughput single-cell RNA-Seq, bioRxiv preprint, http://biorxiv.org/content/early/2014/03/05/003236.full.pdf, 13 pp.

Speicher et al., Oct. 2005, The new cytogenetics: blurring the boundaries with molecular biology, Nature Reviews Genetics, 6(10):782-792.

Stratagene 1998 Catalog, Gene Characterization Kits, p. 39.

Subkhankulova et al., "Comparative evaluation of linear and exponential amplification techniques for expression profiling at the single cell level", Genome Biology, (Mar. 2006) vol. 7, No. R18, pp. 1-16.

Takahashi et al., Mar. 2006, Novel technique of quantitative nested real-time PCR assay for *Mycobacterium tuberculosis* DNA, Journal of Clinical Microbiology, 44(3):1029-1039.

Tan et al., Apr. 2013, Genome-wide comparison of DNA hydroxymethylation in mouse embryonic stem cells and neural progenitor cells by a new comparative hMeDIP-seq method. Nucleic Acids Res. 41(7):884.

Tang et al., "RNA-Seq analysis to capture the transcriptome landscape of a single cell", Nature Protocols, (2010) vol. 5, No. 3, pp. 516-535.

Taudien et al., Apr. 19, 2010, Haplotyping and copy number estimation of the highly polymorphic human beta-defensin locus on 8p23 by 454 amplicon sequencing. BMC Genomics. 11:252.

The Tibbs Times, UNC bioscience newsletter, Apr. 2010, 17 pp.

Tomaz et al., Aug. 2010, Differential methylation as a cause of allele dropout at the Imprinted GNAS locus. Genet Test Mol Biomarkers. 14(4):455-460.

Treutlein et al., May 15, 2014, Reconstructing lineage hierarchies of the distal lung epithelium using single-cell RNA-seq. Nature. 509(7500):371-375.

Vandesompele et al., Jun. 18, 2002, Accurate normalization of real-time quantitative RT-PCR data by geometric averaging of multiple internal control genes, Genome Biology, 3(7).

Velculescu et al., 1995, Serial Analysis of Gene Expression. Science, 270:484-487.

Velculescu et al., 1997, Characterization of the Yeast Transcriptome. Cell, 88:243-251.

Virus, Wikipedia.org, accessed Nov. 24, 2012, 34 pp.

Vogelstein et al., 1999, Digital PCR. Proc. Natl. Acad. Sci., 96(16):9236-9241.

Vollbrecht et al., 2018, Validation and comparison of two NGS assays for the detection of EGFR T790M resistance mutation in liquid biopsies of NSCLC patients, Oncotarget, 9(26):18529-18539.

Walker et al., Jan. 1, 1992, Isothermal in vitro amplification of DNA by a restriction enzyme/DNA polymerase system. Proc Natl Acad Sci U S A., 89(1):392-396.

Walsh et al., Jul. 13, 2010, Detection of inherited mutations for breast and ovarian cancer using genomic capture and massively parallel sequencing, Proc Natl Acad Sci U S A. 107(28):12629-12633.

Wang et al., 2009, RNA-Seq: a revolutionary tool for transcriptomics. Nature Reviews Genetics, 10:57-63.

Wang et al., Jan. 2012, A novel in situ RNA analysis platform for formalin-fixed, paraffin-embedded tissues, The Journal of Molecular Diagnostics, 14(1):22-29.

Wang et al., May 21, 2015, Advances and applications of single-cell sequencing technologies, Molecular Cell, 58(4):598-609.

Wang et al., Oct. 2010, ICLIP predicts the dual splicing effects of TIA-RNA interactions, PLoS Biol, 8(10):e1000530.

Warren et al., Nov. 21, 2006, Transcription factor profiling in individual hematopoietic progenitors by digital RT-PCR, PNAS, 103(47):17807-17812.

Weber et al., Sep. 15, 2003, A real-time polymerase chain reaction assay for quantification of allele ratios and correction of amplification bias. Anal Biochem. 320(2):252-258.

Weiner et al., Apr. 2008, Kits and their unique role in molecular biology: a brief retrospective, BioTechniques, 44:701-704.

White et al., Aug. 23, 2011, High-throughput microfluidic single-cell RT-qPCR, PNAS, 108(34):13999-14004.

Wittes et al., 1999, Searching for Evidence of Altered Gene Expression: a Comment on Statistical Analysis of Microarray Data. Journal of the National Cancer Institute, 91(5):400-401.

Wodicka et al., 1997, Genome-wide expression monitoring in *Saccharomyces cerevisiae*, Nature Biotechnology, 15:1359-1367.

Wojdacz et al., May 16, 2009, Primer design versus PCR bias in methylation independent PCR amplifications. Epigenetics. 4(4):231-234.

Wood et al., Aug. 2010, Using next-generation sequencing for high resolution multiplex analysis of copy number variation from nanogram quantities of DNA from formalin-fixed paraffin-embedded specimens. Nucleic Acids Res. 36(14):e151.

Wu et al., Jan. 2014, Quantitative assessment of single-cell RNA-sequencing methods. Nat Methods. 11(1):41-46.

Yandell et al., Sep. 2011, A probabilistic disease-gene finder for personal genomes. Genome Res. 21(9):1529-1542.

Ye et al., 2001, Fluorescent microsphere-based readout technology for multiplexed human single nucleotide polymorphism analysis and bacterial identification. Human Mutation, 17(4):305-316.

Yoon et al., Sep. 2009, Sensitive and accurate detection of copy number variants using read depth of coverage. Genome Res. 19(9):1586-1592.

Zagordi et al., 2010, Error correction of next-generation sequencing data and reliable estimation of HIV quasispecies, Nucleic Acids Research, 38:7400-7409.

Zhang et al., Jun. 19, 2012, DNA-based hybridization chain reaction for amplified bioelectronic signal and ultrasensitive detection of proteins. Anal Chem., 84(12),5392-5399.

Zhang et al., Mar. 20, 2011, The impact of next-generation sequencing on genomics. J Genet Genomics. 38(3):95-109.

Zhao et al., 2005, Homozygous Deletions and Chromosome Amplifications in Human Lung Carcinomas Revealed by Single Nucleotide Polymorphism Array Analysis. Cancer Research, 65:5561-5570.

Zheng et al., Feb. 2016, Haplotyping germline and cancer genomes with high-throughput linked-read sequencing. Nature Biotechnology, 34(3):303-311.

Zheng et al., Jan. 16, 2017, Massively parallel digital transcriptional profiling of single cells, Nature Communications, 8:14049.

Zhou et al., 2001, Counting alleles reveals a connection between chromosome 18q loss and vascular invasion. Nature Biotechnology, 19:78-81.

Zhu et al., "Reverse transcriptase template switching: a SMART approach for full-length cDNA library construction.", BioTechniques, (Apr. 2001) vol. 30, No. 4, pp. 892-897.

Complaint filed in *Becton, Dickinson and Company and Cellular Research Inc.* v. *10X Genomics, Inc.* on Nov. 15, 2018.

First Amended Complaint filed in *Becton, Dickinson and Company and Cellular Research Inc.* v. *10X Genomics, Inc.* (C.A. No. 18-1800-RGA)) on Feb. 8, 2019.

(56) References Cited

OTHER PUBLICATIONS

Motion to Dismiss and Opening Brief in Support of the Motion to Dismiss filed in *Becton, Dickinson and Company and Cellular Research Inc.* v. *10X Genomics, Inc.* (C.A. No. 18-1800-RGA)) on Jan. 18, 2019.
Plaintiff's Opposition to Defendant 10X Genomics's Motion to Dismiss Pursuant to Federal Rule of Civil Procedure 12(b)(6), filed Feb. 15, 2019 in USDC District of Delaware, C.A. No. 18-1800 (RGA), 3 pp.
Defendant 10X Genomics's Opening Brief in Support of Its Motion to Dismiss Pursuant to Federal Rule of Civil Procedure 12(b)(6), dated Mar. 1, 2019 in USDC District of Delaware, C.A. No. 18-1800 RGA, 101 pp.
Plaintiff's Brief in Opposition to Defendant's Motion to Dismiss Pursuant to Fed. R. Civ. P. 12(b)(6), filed Mar. 29, 2019 in USDC District of Delaware, C.A. No. 18-1800 (RGA), 27 pp.
Defendant 10X Genomics's Reply Brief in Support of Its Motion to Dismiss Pursuant to Federal Rule of Civil Procedure 12(b)(6), dated Apr. 12, 2019 in USDC District of Delaware, C.A. No. 18-1800 RGA, 15 pp.
Decision in Inter Partes Review Case IRP2019-00565, entered Jul. 22, 2019, 30 pp.
Decision in Inter Partes Review Case IRP2019-00566, entered Jul. 22, 2019, 13 pp.
Office Action dated Sep. 8, 2017 in U.S. Appl. No. 15/046,225.
Office Action dated May 3, 2018 in U.S. Appl. No. 15/046,225.
Office Action dated Mar. 19, 2019 in U.S. Appl. No. 15/046,225.
International Search Report and Written Opinion dated May 3, 2016 in PCT/US16/018354.
Examination report dated Sep. 5, 2018 in European patent application No. 16710357.1.
Examination report dated Apr. 26, 2019 in European patent application No. 16710357.1.
Office action dated Oct. 3, 2013 for U.S. Appl. No. 12/969,581.
Response with allowed claims dated Mar. 4, 2014 for U.S. Appl. No. 12/969,581.
Notice of allowance dated Mar. 21, 2014 for U.S. Appl. No. 12/969,581.
Notice of allowance dated Jun. 19, 2014 for U.S. Appl. No. 12/969,581.
Notice of allowance dated Aug. 22, 2014 for U.S. Appl. No. 12/969,581.
Office action dated Dec. 3, 2015 for U.S. Appl. No. 14/281,706.
Office action dated Jul. 20, 2016 for U.S. Appl. No. 14/281,706.
Office action dated Jan. 9, 2018 in U.S. Appl. No. 15/217,896.
Office action dated Jan. 12, 2018 in U.S. Appl. No. 15/217,886.
Office action dated Jul. 20, 2018 in U.S. Appl. No. 15/217,886.
Office Action dated Oct. 11, 2016 in U.S. Appl. No. 15/224,460.
Office Action dated May 8, 2017 in U.S. Appl. No. 15/224,460.
Office Action dated Nov. 5, 2018 in U.S. Appl. No. 16/038,790.
Office Action dated Jan. 14, 2019 in U.S. Appl. No. 16/219,553.
Office Action dated May 7, 2015 for U.S. Appl. No. 13/327,526.
Notice of allowance dated Jan. 21, 2016 for U.S. Appl. No. 13/327,526.
Office action dated Feb. 18, 2015 for U.S. Appl. No. 14/540,007.
Office action dated Sep. 24, 2015 for U.S. Appl. No. 14/540,007.
Notice of allowance dated Dec. 15, 2015 for U.S. Appl. No. 14/540,007.
Office action dated Mar. 19, 2015 for U.S. Appl. No. 14/540,018.
Office action dated Oct. 6, 2015 for U.S. Appl. No. 14/540,018.
Notice of allowance dated Dec. 21, 2015 for U.S. Appl. No. 14/540,018.
Office Action dated Feb. 26, 2015 for U.S. Appl. No. 14/540,029.
Office action dated Sep. 1, 2015 for U.S. Appl. No. 14/540,029.
Office Action dated Jul. 28, 2017 in U.S. Appl. No. 14/975,441.
International Search Report and Written Opinion dated Jun. 6, 2012 in PCT/US11/065291.
Restriction Requirement dated Mar. 15, 2016 in U.S. Appl. No. 14/381,488.
Office Action dated May 10, 2016 in U.S. Appl. No. 14/381,488.
Office Action dated Aug. 12, 2016 in U.S. Appl. No. 14/381,488.
Office Action dated Feb. 13, 2017 in U.S. Appl. No. 14/381,488.
Office Action dated Jun. 7, 2017 in U.S. Appl. No. 14/381,488.
Office Action dated Nov. 16, 2017 in U.S. Appl. No. 14/381,488.
Office Action dated May 10, 2018 in U.S. Appl. No. 14/381,488.
International Search Report and Written Opinion dated Sep. 6, 2013 in PCT/US13/028103.
Examination Report No. 1 for standard patent application, dated Oct. 24, 2017, Australian patent application No. 2013226081.
Office Action dated Feb. 17, 2017 in Canadian patent application No. 2,665,575.
Office Action dated Feb. 15, 2018 in Canadian patent application No. 2,865,575.
Office Action dated Dec. 13, 2018 in Canadian patent application No. 2,865,575.
Office Action dated Jun. 6, 2016 in Chinese patent application No. 201380022187.9.
Office Action dated Dec. 27, 2016 in Chinese patent application No. 201380022187.9.
Office Action dated Jul. 14, 2017 in Chinese patent application No. 201380022187.9.
European search report and search opinion dated Jul. 17, 2015 for European patent application No. 13755319.4.
Examination report dated Jul. 12, 2016 in European patent application No. 13755319.4.
Extended European Search Report dated Feb. 8, 2018 in patent application No. 17202409.3.
Search and Examination Report dated Aug. 6, 2014 for GB patent application No. 1408829.8.
Search and Examination Report dated Jan. 27, 2016 in GB patent application No. 1408829.8.
Examination Report dated Jun. 8, 2016 in GB patent application No. 1408829.8.
Official Action dated Dec. 28, 2016 in Japanese patent application No. 2014-558975.
Final Decision dated Aug. 30, 2017 in Japanese patent application No. 2014-558975.
Notice of Reasons for Rejection dated Apr. 2, 2018 in Japanese patent application No. 2014-558975.
Notice of Reasons for Rejection dated Dec. 5, 2018 in Japanese patent application No. 2017-245295.
Search Report and Written Opinion dated Mar. 1, 2016 in Singapore patent application No. 11201405274W.
Written Opinion dated May 26, 2017 in Singapore patent application No. 11201405274W.
Examination Report dated Mar. 18, 2019 in Singapore patent application No. 1120140274W.
International search report and written opinion dated Aug. 16, 2013 for PCT/US2013/027891.
Extended European Search Report dated Dec. 15, 2015 in European patent application No. 13754428.4.
Examination Report dated Mar. 16, 2018 in European patent application No. 13754428.4.
Restriction Requirement dated Mar. 17, 2016 in U.S. Appl. No. 14/472,363.
Office Action dated Apr. 11, 2016 in U.S. Appl. No. 14/472,363.
Office action dated Dec. 31, 2015 for U.S. Appl. No. 14/800,526.
Office action dated Apr. 11, 2016 for U.S. Appl. No. 14/800,526.
Office action dated Aug. 17, 2016 for U.S. Appl. No. 14/800,526,.
Office Action dated Oct. 25. 2016 in U.S. Appl. No. 14/872,337.
Office action dated Sep. 26, 2016 in U.S. Appl. No. 15/167,807.
Office Action dated May 23, 2019 in U.S. Appl. No. 15/459,977.
Office action dated Oct. 25, 2018 in U.S. Appl. No. 16/012,584.
Office action dated Mar. 1, 2019 in U.S. Appl. No. 16/012,584.
First Action Interview Pilot Program Pre-Interview Communication dated Oct. 15, 2018 in U.S. Appl. No. 15/987,851.
First Action Interview Office Action Summary dated Jan. 25, 2019 in U.S. Appl. No. 15/987,851.
Office Action dated Apr. 22, 2019 in U.S. Appl. No. 15/987,851.
International Search Report and Written Opinion dated Feb. 3, 2015 in PCT/US/14/053301.
Examination Report No. 1 for standard patent application, dated Jul. 20, 2018 Australian patent application No. 2014312208.

(56) References Cited

OTHER PUBLICATIONS

First Office Action dated Jan. 2, 2019 in Chinese patent application No. 201480059505.3.
Examination Report dated Apr. 10, 2017 in European patent application No. 14761937.3.
Examination Report dated Oct. 10, 2017 in European patent application No. 14761937.3.
Extended European Search Report dated Mar. 22, 2019 in patent application No. 18195513.9.
Search and Examination Report dated Aug. 26, 2015 in GB patent application No. 1511591.8.
Examination Report dated Feb. 19, 2016 in Great Britain patent application No. GB1511591.8.
Examination Report dated Jun. 15, 2016 in Great Britain patent application No. GB1511591.8.
Combined Search and Examination Report dated Feb. 21, 2017 in GB patent application No. 1609740.4.
Examination Report dated Jan. 3, 2018 in GB patent application No. 1609740.4.
Third Party Observation dated Jun. 14, 2018 in Japanese patent application No. 2016-537867.
Official Action dated Jul. 30, 2018 in Japanese patent application No. 2016-537867.
Office Action dated May 13, 2016 in U.S. Appl. No. 14/508,911.
Office Action dated Mar. 24, 2017 in U.S. Appl. No. 15/409,355.
Office Action dated Oct. 16, 2017 in U.S. Appl. No. 15/409,355.
International search report and written opinion dated Dec. 19, 2014 for PCT Application No. US2014/059542.
First Office Action dated Dec. 19, 2017 in Chinese patent application No. 201460061859.1.
Second Office Action dated Sep. 7, 2018 in Chinese patent application No. 201480061859.1.
Notice of Reasons for Rejection dated Aug. 31, 2018 in Japanese patent application No. 2016-520632.
Office Action dated Jul. 25, 2018 in U.S. Appl. No. 15/108,268.
Office Action dated Nov. 9, 2017 in U.S. Appl. No. 15/004,618.
Office Action dated Jul. 5, 2016 in U.S. Appl. No. 15/004,618.
International Search Report and Written Opinion dated Jun. 20, 2016 in PCT/US16/14612.
Extended European Search Report dated Jun. 11, 2018 in European patent application No. 16740872.3.
Office Action dated Jan. 19, 2017 in U.S. Appl. No. 15/055,445.
Office Action dated Nov. 1, 2017 in U.S. Appl. No. 15/667,125.
International Search Report and Written Opinion dated Jun. 17, 2016 in PCT/US16/019962.
Written Opinion dated Jul. 5, 2016 in PCT/US16/019962.
Written Opinion dated Sep. 27, 2016 in PCT/US16/019962.
Examination report dated Sep. 26, 2018 in European patent application No. 16714081.3.
Office Action dated Jan. 7, 2019 in U.S. Appl. No. 15/055,407.
Invitation to Pay Additional Search Fees dated Jun. 2, 2016 in PCT/US16/019971.
International Search Report and Written Opinion dated Aug. 9, 2016 in PCT/US16/019971.
Office Action dated May 1, 2020 in U.S. Appl. No. 15/557,789.
Office Action dated Oct. 22, 2020 in U.S. Appl. No. 15/557,789.
Office Action dated Jul. 20, 2021 in U.S. Appl. No. 15/557,789.
International Search Report and Written Opinion dated Jun. 9, 2016 in PCT/US16/022712.
International Search Report and Written Opinion dated Dec. 5, 2016 in PCT/US16/024783.
Examination Report dated Jan. 2, 2019 in European examination report No. 16757986.1.
Office Action dated May 15, 2019 in U.S. Appl. No. 15/064,307.
Office Action dated Sep. 8, 2017 in U.S. Appl. No. 15/134,967.
Office Action dated Nov. 16, 2018 in U.S. Appl. No. 15/134,967.
International Search Report and Written Opinion dated Sep. 28, 2016 in PCT/US16/028694.
Examination Report dated Dec. 12, 2018 in European patent application No. 16719706.0.
Office Action dated Jan. 7, 2020 in U.S. Appl. No. 15/574,122.
Office Action dated Jul. 14, 2020 in U.S. Appl. No. 15/574,122.
Office Action dated Nov. 24, 2020 in U.S. Appl. No. 15/574,122.
Office Action dated Jan. 6, 2021 in U.S. Appl. No. 15/574,122.
International Search Report and Written Opinion dated Sep. 27, 2016 in PCT/US16/034473.
International Search Report and Written Opinion dated Jan. 31, 2017 in PCT/US16/050694.
Office Action dated Mar. 8, 2018 in U.S. Appl. No. 15/608,780.
Office action dated Jul. 25, 2019 in U.S. Appl. No. 15/581,914.
Office action dated Jan. 30, 2020 in U.S. Appl. No. 15/581,914.
Examination Report dated Oct. 26, 2020 in European patent application No. 17735675.5.
International Search Report and Written Opinion dated Sep. 8, 2017 in PCT/US2017/030097.
International Search Report and Written Opinion dated Aug. 7, 2017 in PCT/US2017/034576.
Examination report dated Nov. 26, 2011 in European patent application No. 18833768.7.
International Search Report and Written Opinion dated Mar. 4, 2019 in application No. PCT/US2018/066291.
International Search Report and Written Opinion dated May 28, 2020 in PCT/US2020/017749.
International Search Report and Written Opinion dated Jun. 25, 2020 in PCT/US2020/013685.
Office Action dated Sep. 23, 2021 in U.S. Appl. No. 16/743,898.
International search report and written opinion dated May 7, 2012 for PCT/IB2011/003160.
Notice of opposition dated Jul. 22, 2015 for European patent application No. 11810645.9.
Notice of opposition dated Jul. 9, 2015 for European patent application No. 11810645.9.
Statement of Opposition of Strawman Limited filed against European Patent No. EP2414548B1 on Jul. 19, 2016.
Statement of Opposition filed against European Patent No. EP2414548B1 on Jul. 26, 2016.
Statement of Opposition filed against European Patent No. EP2414548B1 on Jul. 21, 2016.
Submission dated Jan. 15, 2018 by Strawman Limited in preparation for upcoming oral proceedings in opposition against European Patent No. EP2414548B1.
Submission dated Jan. 15, 2018 by Vossius & Partner in preparation for upcoming oral proceedings in opposition against European Patent No. EP2414548B1.
Third-Party Pre-Issuance Submission filed on Jun. 15, 2018 for U.S. Appl. No. 15/847,752.
Third-Party Pre-Issuance Submission filed on Jun. 11, 2018 for U.S. Appl. No. 15/847,752.
Third-Party Pre-Issuance Submission filed on May 21, 2018 for U.S. Appl. No. 15/847,752.

* cited by examiner

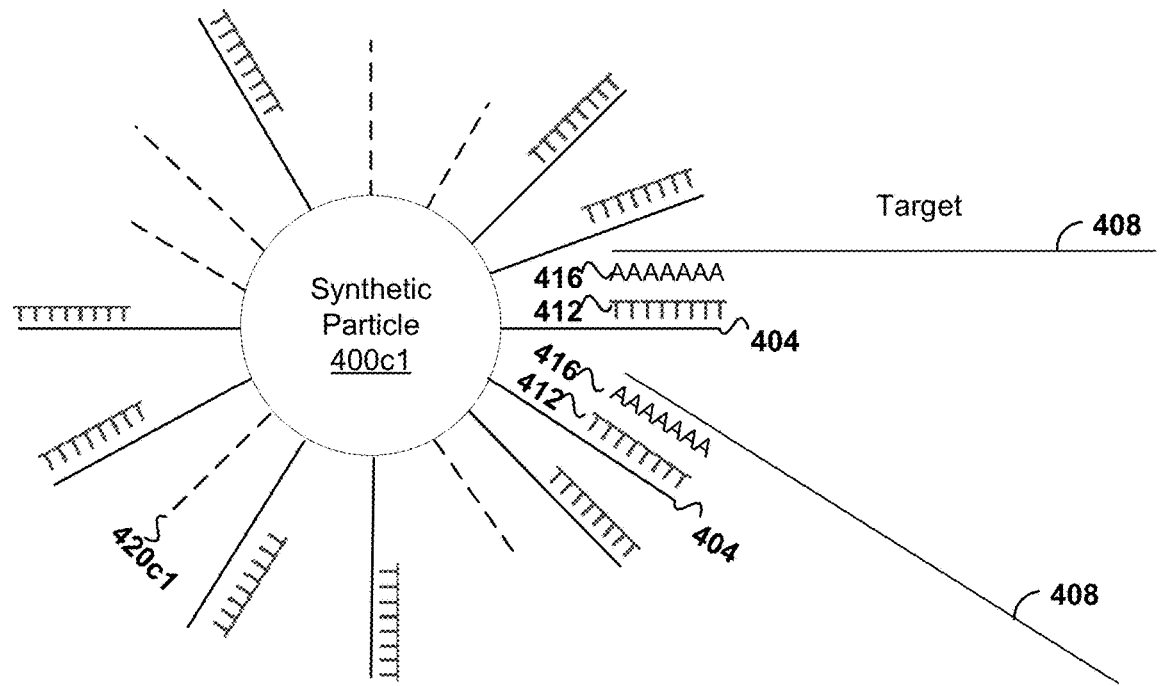
FIG. 4C1
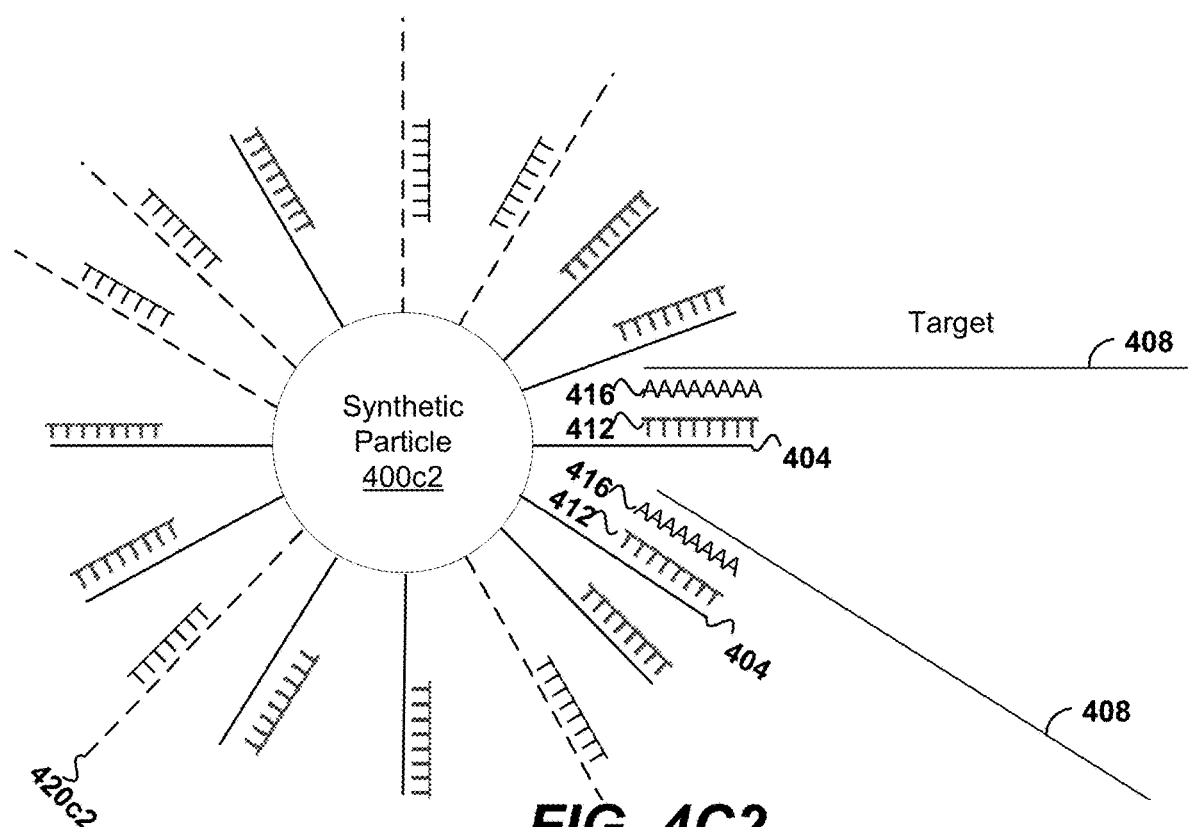
FIG. 4C2

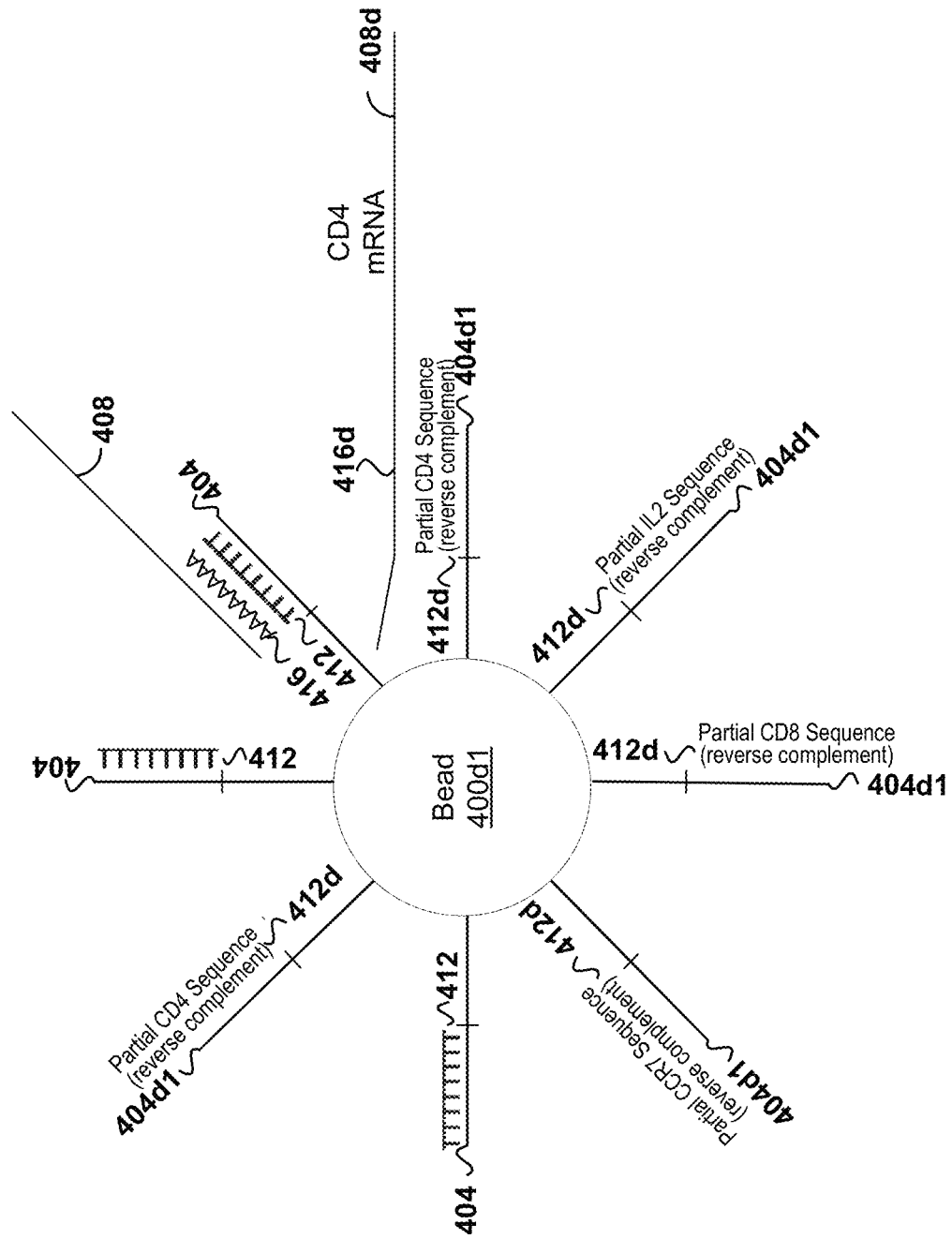
FIG. 4D1

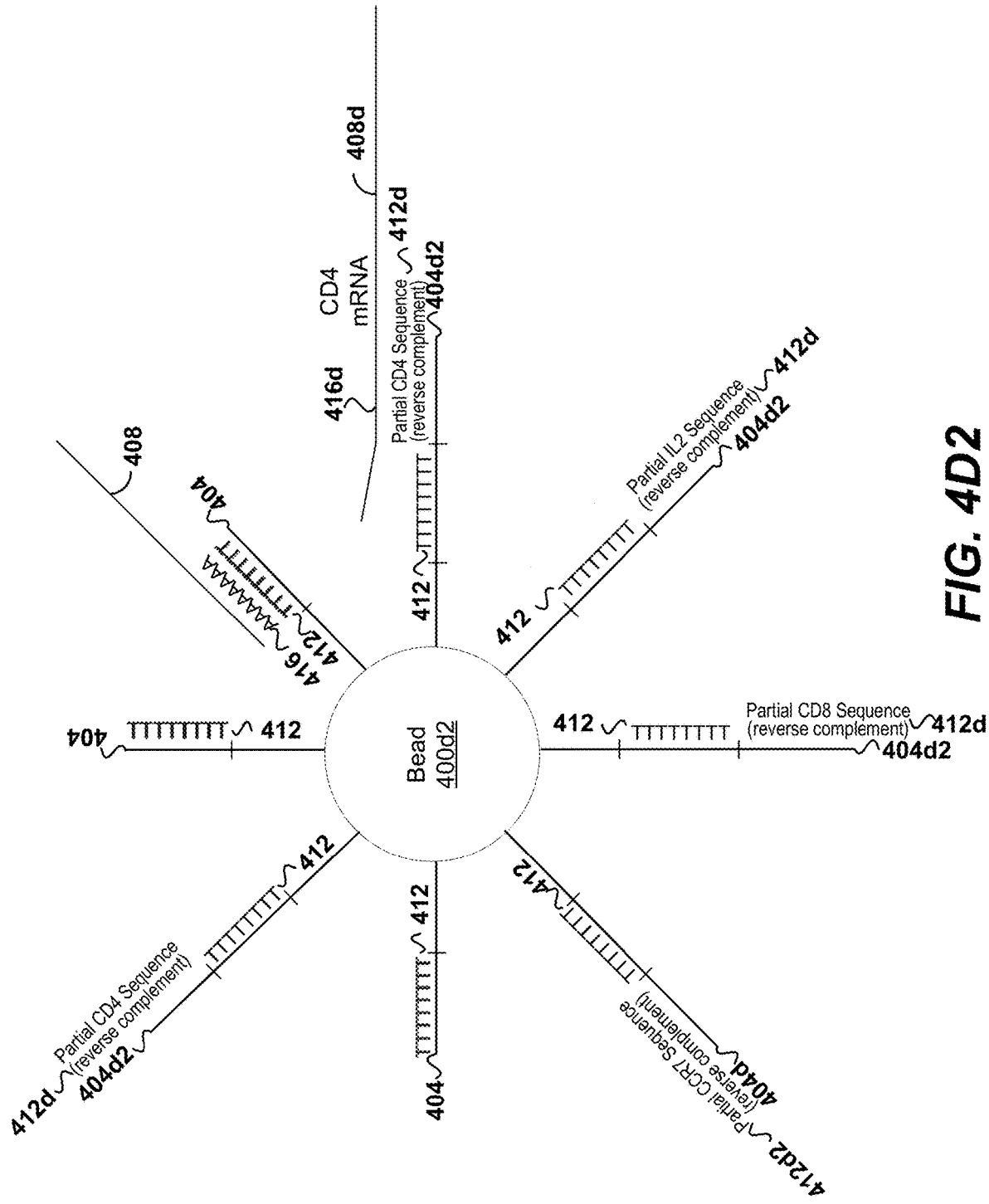
FIG. 4D2

FIG. 5A

SEQ ID NO: 1

5' | TCTCTCTCT | ACACGACGCTCTTCCGATCT | GATGGATG | ACTGGCCTGCGA | CTACACGA
GGTAGCGGGTGAC | TTCCAAGG | NNNNNNNN
TTTTTTTTTTTTTT 3'
412

SEQ ID NO: 2

5' | TCTCTCTCT | ACACGACGCTCTTCCGATCT | GATGGATG | ACTGGCCTGCGA | CTACACGA
GGTAGCGGGTGAC | TTCCAAGG | NNNNNNNN
sequence targeting gene of interest 3'
412d ← 404d1

FIG. 5C

SEQ ID NO: 3

5' | TCTCTCTCT | ACACGACGCTCTTCCGATCT | GATGGATG | ACTGGCCTGCGA | CTACACGA
GGTAGCGGGTGAC | TTCCAAGG | NNNNNNNN
TTTTTTTTTTTTTT | sequence targeting gene of interest 3'
412  412d ← 404d2

PARTICLES ASSOCIATED WITH OLIGONUCLEOTIDES

RELATED APPLICATIONS

The present application is a U.S. national phase application under 35 U.S.C. § 371 of International Application No. PCT/US2018/066291, filed on Dec. 18, 2018, and published on Jun. 27, 2019 as WO 2019/126209, which claims priority under 35 U.S.C. § 119(e) to U.S. Provisional Application No. 62/607,812, filed on Dec. 19, 2017; the content of each of these related applications is incorporated herein by reference in its entirety.

REFERENCE TO SEQUENCE LISTING

The present application is being filed along with a Sequence Listing in electronic format. The Sequence Listing is provided as a file entitled Sequence_Listing_BDCRI_030WO.txt, created on Dec. 18, 2018, which is 2.1 kilobytes in size. The information in the electronic format of the Sequence Listing is incorporated herein by reference in its entirety.

BACKGROUND

Field

The present disclosure relates generally to the field of molecular barcoding of targets and more particularly to improving target capturing.

Description of the Related Art

Methods and techniques such as barcoding using beads coupled to nucleic acid barcodes are useful for cell analysis, in particular deciphering gene expression profiles to determine the states of cells using, for example, reverse transcription, polymerase chain reaction (PCR) amplification, and next generation sequencing (NGS). However, the sensitivity of these methods and techniques can be improved.

SUMMARY

Disclosed herein include embodiments of a synthetic particle. In some embodiments, the synthetic particles comprises: a first plurality of oligonucleotide barcodes; and a second plurality of oligonucleotide barcodes, wherein each of the first plurality of oligonucleotide barcodes and the second plurality of oligonucleotide barcodes comprises an identical cellular label sequence, and a molecular label sequence, wherein at least 10 of the first plurality of oligonucleotide barcodes and the second plurality of oligonucleotide barcodes comprise different molecular label sequences, wherein each of the first plurality of oligonucleotide barcodes comprises a target-binding region, and wherein each of the second plurality of oligonucleotide barcodes comprises a target-specific target-binding region.

In some embodiments, the target-binding region of an oligonucleotide barcode of the first plurality of oligonucleotide barcodes comprises a target-specific target-binding region. In some embodiments, the target-binding region of an oligonucleotide barcode of the first plurality of oligonucleotide barcodes comprises a poly(dT) region. An oligonucleotide barcode of the second plurality of oligonucleotide barcodes can comprise a poly(dT) region.

In some embodiments, the ratio of the first plurality of oligonucleotide barcodes and the second plurality of oligonucleotide barcodes ranges from 1:10 to 10:1. Each of the first plurality of oligonucleotide barcodes and/or the second plurality of oligonucleotide barcodes can comprise a sample label sequence. At least one of the second plurality of oligonucleotide barcodes is shorter than at least one of the first plurality of oligonucleotide barcodes. The target-binding region and the target-specific target binding region can have at most 50% sequence identity. At least two of the first plurality of oligonucleotide barcodes and/or the second plurality of oligonucleotide barcodes can have different lengths. Sequences of at least two of the second plurality of oligonucleotide barcodes and/or the second plurality of oligonucleotide barcodes can be identical. At least two of the first plurality of oligonucleotide barcodes and/or second plurality of oligonucleotide barcodes can comprise an identical sequence.

In some embodiments, the synthetic particle comprises a first plurality of spacer oligonucleotides, wherein each of the first plurality of spacer oligonucleotides does not comprise the target-binding region and the target-specific target-binding region. The synthetic particle can comprise a second plurality of spacer oligonucleotides, wherein each of the second plurality of spacer oligonucleotides does not comprise the target-binding region and the target-specific target-binding region.

In some embodiments, at least one of the first plurality of spacer oligonucleotides is shorter than at least one of the second plurality of spacer oligonucleotides. At least one of the second plurality of spacer oligonucleotides can be shorter than at least one of the first plurality of spacer oligonucleotides. At least two of the first plurality of spacer oligonucleotides and/or the second plurality of spacer oligonucleotides can have different lengths. Sequences of at least two of the first plurality of spacer oligonucleotides and/or the second plurality of spacer oligonucleotides can be identical. At least two of the first plurality of spacer oligonucleotides and/or the second plurality of spacer oligonucleotides can comprise an identical sequence.

In some embodiments, at least one of the first plurality of oligonucleotide barcodes is shorter than at least one of the second plurality of oligonucleotide barcodes. At least one of the second plurality of oligonucleotide barcodes can be shorter than at least one of the first plurality of oligonucleotide barcodes. At least two of the first plurality of oligonucleotide barcodes and/or the second plurality of oligonucleotide barcodes can have different lengths. Sequences of at least two of the first plurality of oligonucleotide barcodes and/or the second plurality of oligonucleotide barcodes can be identical. At least two of the first plurality of oligonucleotide barcodes and/or the second plurality of oligonucleotide barcodes can comprise an identical sequence.

In some embodiments, at least 100 of the first plurality of oligonucleotide barcodes and/or second plurality of oligonucleotide barcodes comprise different molecular label sequences. The target-binding region can comprise a target-specific sequence, an oligo(dT) sequence, a random multimer, or any combination thereof. Two target-specific target-binding regions of two oligonucleotide barcodes of the second plurality of oligonucleotide barcodes can comprise different target-specific sequences. Each cellular label sequence can comprise at least 6 nucleotides. Each molecular label sequence can comprise at least 6 nucleotides. Each of the first plurality of oligonucleotide barcodes and/or second plurality of oligonucleotide barcodes can comprise a spatial label sequence, and wherein the spatial label sequences differ from one another by at least one nucleotide. Each of the first plurality of oligonucleotide barcodes and/or second plurality of oligonucleotide barcodes can comprise a universal sequence, wherein the universal sequences are the same.

In some embodiments, at least one of the first plurality of oligonucleotide barcodes and/or second plurality of oligonucleotide barcodes is immobilized on the synthetic particle. At least one of the first plurality of oligonucleotide barcodes and/or second plurality of oligonucleotide barcodes can be partially immobilized on the synthetic particle. At least one of the first plurality of oligonucleotide barcodes and/or second plurality of oligonucleotide barcodes can be enclosed in the synthetic particle. At least one of the first plurality of oligonucleotide barcodes and/or second plurality of oligonucleotide barcodes can be partially enclosed in the synthetic particle. The synthetic particle can be disruptable. The synthetic particle can comprise a bead. The bead can comprise a magnetic bead. The synthetic particle can comprises a disruptable hydrogel particle, such as a disruptable hydrogel bead.

In some embodiments, each of the first plurality of oligonucleotide barcodes and/or the second plurality of oligonucleotide barcodes can comprise a linker functional group, the synthetic particle can comprise a solid support functional group, and the support functional group and the linker functional group can be associated with each other. The linker functional group and the support functional group can be individually selected from the group consisting of C6, biotin, streptavidin, primary amine(s), aldehyde(s), ketone(s), sulfide(s) and any combination thereof.

Disclosed herein include embodiments of a kit or a composition. In some embodiments, the kit or composition comprises: a plurality of synthetic particles, wherein each synthetic particle comprises: a first plurality of oligonucleotide barcodes; and a second plurality of oligonucleotide barcodes, wherein each of the first plurality of oligonucleotide barcodes and the second plurality of oligonucleotide barcodes comprises an identical cellular label sequence and a molecular label sequence, wherein at least 10 of the first plurality of oligonucleotide barcodes and the second plurality of oligonucleotide barcodes comprise different molecular label sequences, wherein each of the first plurality of oligonucleotide barcodes comprises a target-binding region, and wherein each of the second plurality of oligonucleotide barcodes comprises a target-specific target-binding region; and optionally instructions for using the plurality of synthetic particles. In some embodiments, the kit comprises a buffer, one or more reagents for a reverse transcription reaction, one or more reagents for an amplification reaction, or a combination thereof.

In some embodiments, the plurality of synthetic particles comprises at least 94 synthetic particles. The kit can comprise a plurality of partitions each comprising a synthetic particle of the plurality synthetic particles. The plurality of partitions can comprise microwells of a microwell array. The plurality of partitions ca comprise a plurality of droplets.

In some embodiments, the target-binding region of an oligonucleotide barcode of the first plurality of oligonucleotide barcodes comprises a target-specific target-binding region. The target-binding region of an oligonucleotide barcode of the first plurality of oligonucleotide barcodes can comprise a poly(dT) region. An oligonucleotide barcode of the second plurality of oligonucleotide barcodes can comprise a poly(dT) region.

In some embodiments, the ratio of the first plurality of oligonucleotide barcodes and the second plurality of oligo- nucleotide barcodes ranges from 1:10 to 10:1. Each of the first plurality of oligonucleotide barcodes and/or the second plurality of oligonucleotide barcodes can comprise a sample label sequence. At least one of the second plurality of oligonucleotide barcodes can be shorter than at least one of the first plurality of oligonucleotide barcodes. The target-binding region and the sequence-specific target-binding region can have at most 50% sequence identity. At least two of the first plurality of oligonucleotide barcodes and/or the second plurality of oligonucleotide barcodes can have different lengths. Sequences of at least two of the first plurality of oligonucleotide barcodes and/or the second plurality of oligonucleotide barcodes can be identical. At least two of the first plurality of oligonucleotide barcodes and/or the second plurality of oligonucleotide barcodes can comprise an identical sequence.

In some embodiments, each synthetic particle comprises a first plurality of spacer oligonucleotides, wherein each of the first plurality of spacer oligonucleotides does not comprise the target-binding region and the target-specific target-binding region. Each synthetic particle can comprise a second plurality of spacer oligonucleotides, wherein each of the second plurality of spacer oligonucleotides does not comprise does not comprise the target-binding region and the target-specific target-binding region.

In some embodiments, at least one of the first plurality of spacer oligonucleotides is shorter than at least one of the second plurality of spacer oligonucleotides. At least one of the second plurality of spacer oligonucleotides can be shorter than at least one of the first plurality of spacer oligonucleotides. At least two of the first plurality of spacer oligonucleotides and/or the second plurality of spacer oligonucleotides can have different lengths. Sequences of at least two of the first plurality of spacer oligonucleotides and/or the second plurality of spacer oligonucleotides can be identical. At least two of the first plurality of spacer oligonucleotides and/or the second plurality of spacer oligonucleotides can comprise an identical sequence.

In some embodiments, at least one of the first plurality of oligonucleotide barcodes is shorter than at least one of the second plurality of oligonucleotide barcodes. At least one of the second plurality of oligonucleotide barcodes can be shorter than at least one of the first plurality of oligonucleotide barcodes. At least two of the first plurality of oligonucleotide barcodes and/or the second plurality of oligonucleotide barcodes can have different lengths. Sequences of at least two of the first plurality of oligonucleotide barcodes and/or the second plurality of oligonucleotide barcodes can be identical. At least two of the first plurality of oligonucleotide barcodes and/or the second plurality of oligonucleotide barcodes can comprise an identical sequence.

In some embodiments, at least 100 of the first plurality of oligonucleotide barcodes and/or the second plurality of oligonucleotide barcodes comprise different molecular label sequences. The target-binding region can comprise a target-specific sequence, an oligo(dT) sequence, a random multimer, or any combination thereof. Two target-specific target-binding regions of two oligonucleotide barcodes of the second plurality of oligonucleotide barcodes can comprise different target-specific sequences. Each cellular label sequence can comprise at least 6 nucleotides. Each molecular label sequence can comprise at least 6 nucleotides. Each of the first plurality of oligonucleotide barcodes and/or the second plurality of oligonucleotide barcodes can comprise a spatial label sequence, and wherein spatial label sequences differ from one another by at least one nucleotide. Each of the first plurality of oligonucleotide barcodes and/or the second plurality of oligonucleotide barcodes can comprises a universal sequence, wherein universal sequences are the same.

In some embodiments, at least one of the plurality of synthetic particle oligonucleotides is immobilized on the synthetic particle. At least one of the first plurality of oligonucleotide barcodes can be partially immobilized on the synthetic particle. At least one of the first plurality of oligonucleotide barcodes can be enclosed in the synthetic particle. At least one of the first plurality of oligonucleotide barcodes can be partially enclosed in the synthetic particle. The synthetic particle can be disruptable. The synthetic particle can comprise a bead. The bead can comprise a magnetic bead. The synthetic particle can comprise a disruptable hydrogel particle, such as a hydrogel bead.

In some embodiments, each of the first plurality of oligonucleotide barcodes and/or the second plurality of oligonucleotide barcodes comprises a linker functional group, the synthetic particle comprises a solid support functional group, and the support functional group and the linker functional group are associated with each other. The linker functional group and the support functional group can be individually selected from the group consisting of C6, biotin, streptavidin, primary amine(s), aldehyde(s), ketone(s), sulfide(s) and any combination thereof.

Disclosed herein include embodiments of a method for determining the numbers of targets in a sample. In some embodiments, the method comprises: barcoding copies of a first plurality of targets using a first plurality of oligonucleotide barcodes associated with a synthetic particle to generate copies of a first plurality of barcoded targets; barcoding copies of a second plurality of targets in a sample using a second plurality of oligonucleotide barcodes associated with the synthetic particle to generate copies of a second plurality of barcoded targets, wherein each of the first plurality of oligonucleotide barcodes and the second plurality of oligonucleotide barcodes comprises an identical cellular label sequence and a molecular label sequence, wherein at least 10 of the first plurality of oligonucleotide barcodes and the second plurality of oligonucleotide barcodes comprise different molecular label sequences, wherein each of the first plurality of oligonucleotide barcodes comprises a target-binding region, and wherein each of the second plurality of oligonucleotide barcodes comprises a target-specific target-binding region; and estimating the number of each of the first plurality of targets and/or the second plurality of targets using the molecular label sequences of the first plurality of oligonucleotide barcodes and the second plurality of oligonucleotide barcodes.

In some embodiments, the target-binding region of an oligonucleotide barcode of the first plurality of oligonucleotide barcodes comprises a target-specific target-binding region. The target-binding region of an oligonucleotide barcode of the first plurality of oligonucleotide barcodes can comprise a poly(dT) region. An oligonucleotide barcode of the second plurality of oligonucleotide barcodes can comprise a poly(dT) region.

In some embodiments, first plurality of targets comprises mRNA molecules of a cell, and wherein the second plurality of targets comprises DNA molecules of the cell. The first plurality of targets can comprise mRNA molecules of a cell, and the second plurality of targets can comprise RNA molecules of a virus, a bacterium, and/or a fungus infecting the cell.

In some embodiments, barcoding the copies of the first plurality of targets in the sample using the first plurality of oligonucleotide barcodes associated with the synthetic particle comprises: hybridizing the first plurality of targets to the first plurality of oligonucleotide barcodes on the synthetic particle, wherein barcoding the copies of the second plurality of targets in the sample using the second plurality of oligonucleotide barcodes associated with the synthetic particle comprises: hybridizing the second plurality of targets to the second plurality of oligonucleotide barcodes on the synthetic particle. Barcoding the copies of the first plurality of targets can comprise: reverse transcribing the first plurality of targets to generate barcoded cDNAs of the first plurality of targets, and wherein barcoding the copies of the second plurality of targets comprises: reverse transcribing the second plurality of targets to generate barcoded cDNAs of the second plurality of targets. The method can comprise amplifying the barcoded cDNAs of the first plurality of targets and/or amplifying the barcoded cDNAs of the second plurality of targets using second strand synthesis to generate first double-stranded barcoded targets and second double-stranded barcoded targets, respectively. The method can comprise amplifying the first double-stranded barcoded targets and second double-stranded barcoded targets to generate first labeled target amplicons and second labeled target amplicons, respectively.

Disclosed herein include embodiments of a method for capturing targets in a sample. In some embodiments, the method comprises: hybridizing copies of a first plurality of targets using a first plurality of oligonucleotide barcodes associated with a synthetic particle to generate copies of a first plurality of barcoded targets; hybridizing copies of a second plurality of targets using a second plurality of oligonucleotide barcodes associated with the synthetic particle to generate copies of a second plurality of barcoded targets, wherein each of the first plurality of oligonucleotide barcodes and the second plurality of oligonucleotide barcodes comprises an identical cellular label sequence and a molecular label sequence, wherein at least 10 of the first plurality of oligonucleotide barcodes and the second plurality of oligonucleotide barcodes comprise different molecular label sequences, wherein each of the first plurality of oligonucleotide barcodes comprises a target-binding region, and wherein each of the second plurality of oligonucleotide barcodes comprises a target-specific target-binding region.

In some embodiments, the copies of the second plurality of barcoded targets comprise at least 50% of copies of a target of the plurality of targets. The copies of the second plurality of barcoded targets can comprise at least 75% of copies of a target of the second plurality of targets. The copies of the second plurality of barcoded targets can comprise at least 95% of copies of a target of the second plurality of targets. The copies of the second plurality of barcoded targets can comprise at least 50% of copies of each target of the second plurality of targets. The copies of the second plurality of barcoded targets can comprise at least 75% of copies of each target of the second plurality of targets. The copies of the second plurality of barcoded targets can comprise at least 95% of copies of each target of the second plurality of targets.

In some embodiments, the first plurality of targets and the second plurality of targets comprises mRNAs, the method comprising: reverse transcribing the first plurality of targets to generate first barcoded cDNAs of the first plurality of targets; and reverse transcribing the second plurality of targets to generate second barcoded cDNAs of the second plurality of targets. The method can comprise amplifying the first barcoded cDNAs and the second barcoded cDNAs using second strand synthesis to generate first barcoded double-stranded targets and second barcoded double-stranded targets, respectively. The method can comprise amplifying the first barcoded targets and the second barcoded targets to generate first labeled target amplicons and second labeled target amplicons, respectively.

In some embodiments, the first plurality of targets and the second plurality of targets are from a single cell, the method comprising associating the synthetic particle with the single cell. The single cell can comprise a rare cell, a tumor cell, a cell from a human, a cell from a tissue, a cell from a tumor, a cell infected with viral polynucleotides, or any combination thereof.

In some embodiments, the method comprises lysing the single cell after associating the synthetic particle with the single cell. Lysing the single cell can comprise heating the sample, contacting the sample with a detergent, changing the pH of the sample, or any combination thereof. The synthetic particle and the single cell can be in the same well. The synthetic particle and the single cell can be in the same droplet.

In some embodiments, the first plurality of targets and/or the second plurality of targets comprises ribonucleic acids (RNAs), messenger RNAs (mRNAs), microRNAs, small interfering RNAs (siRNAs), RNA degradation products, RNAs each comprising a poly(A) tail, RNAs without any poly(A) tail, viral RNAs, and any combination thereof.

In some embodiments, the ratio of the first plurality of oligonucleotide barcodes and the second plurality of oligonucleotide barcodes ranges from 1:10 to 10:1. Each of the first plurality of oligonucleotide barcodes and/or the second plurality of oligonucleotide barcodes can comprise a a sample label sequence. At least one of the second plurality of oligonucleotide barcodes can be shorter than at least one of the first plurality of oligonucleotide barcodes. The target-binding region and the target-specific target-binding region can have at most 50% sequence identity. At least two of the first plurality of oligonucleotide barcodes and/or the second plurality of oligonucleotide barcodes can have different lengths. Sequences of at least two of the first plurality of oligonucleotide barcodes and/or the second plurality of oligonucleotide barcodes are identical. At least two of the first plurality of oligonucleotide barcodes and/or the second plurality of oligonucleotide barcodes can comprise an identical sequence.

In some embodiments, the synthetic particle comprises a first plurality of spacer oligonucleotides, wherein each of the first plurality of spacer oligonucleotides does not comprise the target-binding region and the target-specific target-binding region. The synthetic particle can comprise a second plurality of spacer oligonucleotides, wherein each of the second plurality of spacer oligonucleotides does not comprise the target-binding region and the target-specific target-binding region.

In some embodiments, at least one of the first plurality of spacer oligonucleotides is shorter than at least one of the second plurality of spacer oligonucleotides. At least one of the second plurality of spacer oligonucleotides can be shorter than at least one of the first plurality of spacer oligonucleotides. At least two of the first plurality of spacer oligonucleotides and/or the second plurality of spacer oligonucleotides can have different lengths. Sequences of at least two of the first plurality of spacer oligonucleotides and/or the second plurality of spacer oligonucleotides can be identical. At least two of the first plurality of spacer oligonucleotides and/or the second plurality of spacer oligonucleotides can comprise an identical sequence.

In some embodiments, at least one of the first plurality of oligonucleotide barcodes is shorter than at least one of the second plurality of oligonucleotide barcodes. At least one of the second plurality of oligonucleotide barcodes can be shorter than at least one of the first plurality of oligonucleotide barcodes. At least two of the first plurality of oligonucleotide barcodes and/or the second plurality of oligonucleotide barcodes can have different lengths. Sequences of at least two of the first plurality of oligonucleotide barcodes and/or the second plurality of oligonucleotide barcodes can be identical. At least two of the first plurality of oligonucleotide barcodes and/or the second plurality of oligonucleotide barcodes can comprise an identical sequence.

In some embodiments, at least 100 of the first plurality of oligonucleotide barcodes and/or the second plurality of oligonucleotide barcodes comprise different molecular label sequences. The target-binding region can comprise a target-specific sequence, an oligo(dT) sequence, a random multimer, or any combination thereof. Two target-binding regions of two oligonucleotide barcodes of the second plurality of oligonucleotide barcodes can comprise target-specific sequences. Each cellular label sequence can comprise at least 6 nucleotides. Each molecular label sequence can comprise at least 6 nucleotides. Each of the first plurality of oligonucleotide barcodes and/or the second plurality of oligonucleotide barcodes can comprise a spatial label sequence, and wherein spatial label sequences differ from one another by at least one nucleotide. Each of the first plurality of oligonucleotide barcodes and/or the second plurality of oligonucleotide barcodes can comprise a universal sequence, wherein universal sequences are the same.

In some embodiments, at least one of the first plurality of oligonucleotide barcodes and/or the second plurality of oligonucleotide barcodes is immobilized on the synthetic particle. At least one of the first plurality of oligonucleotide barcodes can be partially immobilized on the synthetic particle. At least one of the first plurality of oligonucleotide barcodes can be enclosed in the synthetic particle. At least one of the first plurality of oligonucleotide barcodes can be partially enclosed in the synthetic particle. The synthetic particle can be disruptable. The synthetic particle can comprise a bead. The bead can comprise a magnetic bead. The synthetic particle can comprise a disruptable hydrogel particle, such as a hydrogel bead.

In some embodiments, each of the first plurality of oligonucleotide barcodes and/or the second plurality of oligonucleotide barcodes comprises a linker functional group, the synthetic particle comprises a solid support functional group, and the support functional group and the linker functional group are associated with each other. The linker functional group and the support functional group can be individually selected from the group consisting of C6, biotin, streptavidin, primary amine(s), aldehyde(s), ketone(s), and any combination thereof.

Disclosed herein include embodiments of a synthetic particle. In some embodiments, the synthetic particle comprises: a plurality of oligonucleotide barcodes, wherein each of the plurality of oligonucleotide barcodes comprises an identical cellular label sequence, a molecular label sequence, and a target-binding region, and wherein at least 10 of the plurality of oligonucleotide barcodes comprise different molecular label sequences, and a first plurality of spacer oligonucleotides, wherein each of the first plurality of spacer oligonucleotides does not comprise the target-binding region. The ratio of the plurality of oligonucleotide barcodes and the first plurality of spacer oligonucleotides can range from 1:10 to 10:1. Each of the first plurality of spacer oligonucleotides can comprise a cellular label sequence or a molecular label sequence.

In some embodiments, at least one of the first plurality of spacer oligonucleotides can be shorter than at least one of the plurality of oligonucleotide barcodes. Each of the first plurality of spacer oligonucleotides can comprise a region that corresponds to the target-binding region, and wherein the region that corresponds to the target-binding region and the target-binding region have different sequences. The region that corresponds to the target-binding region and the target-binding region can have at most 50% sequence identity. At least two of the first plurality of spacer oligonucleotides can have different lengths. Sequences of at least two of the first plurality of spacer oligonucleotides can be identical. At least two of the first plurality of spacer oligonucleotides can comprise an identical sequence.

In some embodiments, the synthetic particle comprises a second plurality of spacer oligonucleotides, wherein each of the second plurality of spacer oligonucleotides does not comprise the target-binding region. At least one of the second plurality of spacer oligonucleotides can be shorter than at least one of the first plurality of spacer oligonucleotides. At least one of the second plurality of spacer oligonucleotides can be shorter than at least one of the plurality of oligonucleotide barcodes. At least two of the second plurality of spacer oligonucleotides can have different lengths. Sequences of at least two of the second plurality of spacer oligonucleotides can be identical. At least two of the second plurality of spacer oligonucleotides comprise an identical sequence.

In some embodiments, at least 100 of the plurality of oligonucleotide barcodes comprise different molecular label sequences. The target-binding region can comprise a gene-specific sequence, an oligo(dT) sequence, a random multimer, or any combination thereof. Two target-binding regions of two oligonucleotide barcodes of the plurality of oligonucleotide barcodes can comprise different gene-specific sequences. Each cellular label sequence of the plurality of oligonucleotide barcodes can comprise at least 6 nucleotides. Each molecular label sequence of the plurality of oligonucleotide barcodes can comprise at least 6 nucleotides. Each of the plurality of oligonucleotide barcodes can comprise a spatial label sequence, and wherein spatial label sequences of the plurality of oligonucleotide barcodes differ from one another by at least one nucleotide. Each of the plurality of oligonucleotide barcodes can comprise a universal label sequence, wherein universal label sequences of the plurality of oligonucleotide barcodes are the same.

In some embodiments, at least one of the plurality of oligonucleotide barcodes is immobilized, partially immobilized, enclosed, partially enclosed, or any combination thereof, on the synthetic particle. The synthetic particle can be disruptable. The synthetic particle can comprise a bead. The bead can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The synthetic particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. The synthetic particle can comprise a disruptable hydrogel particle. Each of the plurality of oligonucleotide barcodes can comprise a linker functional group, the synthetic particle can comprise a solid support functional group, and/or the support functional group and the linker functional group can be associated with each other. The linker functional group and the support functional group can be individually selected from the group consisting of C6, biotin, streptavidin, primary amine(s), aldehyde(s), ketone(s), and any combination thereof. In some embodiments, the plurality of synthetic particles comprises at least 94 synthetic particles. The kit can comprise a microwell array, wherein each microwell of the microwell array comprises a synthetic particle of the plurality synthetic particles. The kit can comprise a buffer, a cartridge, one or more reagents for a reverse transcription reaction, one or more reagents for an amplification reaction, or an combination thereof. The ratio of the plurality of oligonucleotide barcodes and the first plurality of spacer oligonucleotides can range from 1:10 to 10:1. Each of the first plurality of spacer oligonucleotides can comprise a cellular label sequence or a molecular label sequence.

Provided herein include embodiments of a kit. In some embodiments, the kit comprises: a plurality of synthetic particles, wherein each synthetic particle comprises: a plurality of oligonucleotide barcodes, wherein each of the plurality of oligonucleotide barcodes comprises an identical cellular label sequence, a molecular label sequence, and a target-binding region, and wherein at least 10 of the plurality of oligonucleotide barcodes comprise different molecular label sequences, and a first plurality of spacer oligonucleotides, wherein each of the first plurality of spacer oligonucleotides does not comprise the target-binding region. The kit can comprise: instructions for using the plurality of oligonucleotide barcodes.

In some embodiments, at least one of the first plurality of spacer oligonucleotides is shorter than at least one of the plurality of oligonucleotide barcodes. Each of the first plurality of spacer oligonucleotides can comprise a region that corresponds to the target-binding region. The region that corresponds to the target-binding region and the target-binding region can have different sequences. The region that corresponds to the target-binding region and the target-binding region can have at most 50% sequence identity. At least two of the first plurality of spacer oligonucleotides can have different lengths. Sequences of at least two of the first plurality of spacer oligonucleotides can be identical. At least two of the first plurality of spacer oligonucleotides can comprise an identical sequence.

In some embodiments, the synthetic particle comprises a second plurality of spacer oligonucleotides, wherein each of the second plurality of spacer oligonucleotides does not comprise the target-binding region. At least one of the second plurality of spacer oligonucleotides can be shorter than at least one of the first plurality of spacer oligonucleotides. At least one of the second plurality of spacer oligonucleotides can be shorter than at least one of the plurality of oligonucleotide barcodes. At least two of the second plurality of spacer oligonucleotides can have different lengths. Sequences of at least two of the second plurality of spacer oligonucleotides can be identical. At least two of the second plurality of spacer oligonucleotides can comprise an identical sequence.

In some embodiments, at least 100 of the plurality of oligonucleotide barcodes comprise different molecular label sequence sequences. The target-binding region can comprise a gene-specific sequence, an oligo(dT) sequence, a random multimer, or any combination thereof. Two target-binding regions of two oligonucleotide barcodes of the plurality of oligonucleotide barcodes can comprise different gene-specific sequences. Each cellular label sequence of the plurality of oligonucleotide barcodes can comprise at least 6 nucleotides. Each molecular label sequence of the plurality of oligonucleotide barcodes can comprise at least 6 nucleotides. Each of the plurality of oligonucleotide barcodes can comprise a spatial label sequence, and wherein spatial label sequences of the plurality of oligonucleotide barcodes differ from one another by at least one nucleotide. Each of the plurality of oligonucleotide barcodes can comprise a universal label sequence, wherein universal label sequences of the plurality of oligonucleotide barcodes are the same.

In some embodiments, at least one of the plurality of oligonucleotide barcodes is immobilized on, partially immobilized on, enclosed in, partially enclosed in, or any combination thereof, the synthetic particle. The synthetic particle can be disruptable. The synthetic particle can comprise a bead. The bead can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The synthetic particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. The synthetic particle can comprise a disruptable hydrogel particle. Each of the plurality of oligonucleotide barcodes can comprise a linker functional group, the synthetic particle can comprise a solid support functional group, and/or the support functional group and the linker functional group can be associated with each other. The linker functional group and the support functional group can be individually selected from the group consisting of C6, biotin, streptavidin, primary amine(s), aldehyde(s), ketone(s), and any combination thereof.

Embodiments disclosed herein include methods for determining the numbers of targets in a sample. In some embodiments, the method comprises: barcoding copies of a plurality of targets in a sample using a plurality of oligonucleotide barcodes associated with a synthetic particle to generate copies of a plurality of barcoded targets, wherein each of the plurality of oligonucleotide barcodes comprises an identical cellular label sequence, a molecular label sequence, and a target-binding region, and wherein at least 10 of the plurality of oligonucleotide barcodes comprise different molecular label sequences, wherein the synthetic particle comprises a first plurality of spacer oligonucleotides, and wherein each of the first plurality of spacer oligonucleotides does not comprise the target-binding region; and estimating the number of each of the plurality of targets in the sample using the molecular label sequences of the plurality of oligonucleotide barcodes. In some embodiments, barcoding the copies of the plurality of targets in the sample using the plurality of oligonucleotide barcodes associated with the synthetic particle can comprise: hybridizing the plurality of targets to the plurality of oligonucleotide barcodes on the synthetic particle. Barcoding the copies of the plurality of targets can comprise: reverse transcribing the plurality of targets to generate barcoded cDNAs of the plurality of targets. The method can comprise: amplifying the barcoded cDNAs using second strand synthesis to generate barcoded targets, wherein the barcoded targets are double-stranded. The method can comprise: amplifying the barcoded targets to generate labelled target amplicons.

Disclosed herein are embodiments of a method for capturing targets in a sample. In some embodiments, the method comprises: hybridizing copies of a plurality of targets in a sample using a plurality of oligonucleotide barcodes associated with a synthetic particle to generate copies of a plurality of barcoded targets, wherein each of the plurality of oligonucleotide barcodes comprises an identical cellular label sequence, a molecular label sequence, and a target-binding region, and wherein at least 10 of the plurality of oligonucleotide barcodes comprise different molecular label sequences, wherein the synthetic particle comprises a first plurality of spacer oligonucleotides, and wherein each of the first plurality of spacer oligonucleotides does not comprise the target-binding region. In some embodiments, the copies of the plurality of barcoded targets can comprise at least 50%, 75%, 95%, or any combination thereof, of copies of a target of the plurality of targets in the sample. The copies of the plurality of barcoded targets can comprise at least 50%, 75%, 95%, or any combination thereof, of copies of each target of the plurality of targets in the sample. The method can comprise: reverse transcribing the plurality of targets to generate barcoded cDNAs of the plurality of targets. The method can comprise: amplifying the barcoded cDNAs using second strand synthesis to generate barcoded targets, wherein the barcoded targets are double-stranded. The method can comprise: comprising amplifying the barcoded targets to generate labelled target amplicons.

In some embodiments, the sample comprises a single cell, the method comprising associating the synthetic particle with the single cell in the sample. The single cell can comprise a rare cell, a tumor cell, a cell from a human, a cell from a tissue, a cell from a tumor, a cell infected with viral polynucleotides, and any combination thereof. The method can comprise: lysing the single cell after associating the synthetic particle with the single cell. The method can comprise: lysing the single cell comprises heating the sample, contacting the sample with a detergent, changing the pH of the sample, or any combination thereof. The synthetic particle and the single cell can be in the same well. The synthetic particle and the single cell can be in the same droplet. The plurality of targets can comprise ribonucleic acids (RNAs), messenger RNAs (mRNAs), microRNAs, small interfering RNAs (siRNAs), RNA degradation products, RNAs each comprising a poly(A) tail, and any combination thereof.

In some embodiments, the ratio of the plurality of oligonucleotide barcodes and the first plurality of spacer oligonucleotides ranges from 1:10 to 10:1. Each of the first plurality of spacer oligonucleotides can comprise a cellular label sequence or a molecular label sequence. At least one of the first plurality of spacer oligonucleotides can be shorter than at least one of the plurality of oligonucleotide barcodes. Each of the first plurality of spacer oligonucleotides can comprise a region that corresponds to the target-binding region, and wherein the region that corresponds to the target-binding region and the target-binding region have different sequences. The region that corresponds to the target-binding region and the target-binding region can have at most 50% sequence identity. At least two of the first plurality of spacer oligonucleotides can have different lengths. Sequences of at least two of the first plurality of spacer oligonucleotides can be identical. At least two of the first plurality of spacer oligonucleotides can comprise an identical sequence.

In some embodiments, the synthetic particle can comprise a second plurality of spacer oligonucleotides, wherein each of the second plurality of spacer oligonucleotides does not comprise the target-binding region. At least one of the second plurality of spacer oligonucleotides can be shorter than at least one of the first plurality of spacer oligonucleotides. At least one of the second plurality of spacer oligonucleotides can be shorter than at least one of the plurality of oligonucleotide barcodes. At least two of the second plurality of spacer oligonucleotides can have different lengths. Sequences of at least two of the second plurality of spacer oligonucleotides can be identical. At least two of the second plurality of spacer oligonucleotides can comprise an identical sequence.

In some embodiments, at least 100 of the plurality of oligonucleotide barcodes comprise different molecular label sequences. The target-binding region can comprise a gene-specific sequence, an oligo(dT) sequence, a random multimer, or any combination thereof. Two target-binding regions of two oligonucleotide barcodes of the plurality of oligonucleotide barcodes can comprise different gene-specific sequences. Each cellular label sequence of the plurality of oligonucleotide barcodes can comprise at least 6 nucleotides. Each molecular label sequence of the plurality of oligonucleotide barcodes can comprise at least 6 nucleotides. Each of the plurality of oligonucleotide barcodes can comprise a spatial label sequence, and wherein spatial label sequences of the plurality of oligonucleotide barcodes differ from one another by at least one nucleotide. Each of the plurality of oligonucleotide barcodes can comprise a universal label sequence, wherein universal label sequences of the plurality of oligonucleotide barcodes are the same.

In some embodiments, at least one of the plurality of oligonucleotide barcodes is immobilized on, partially immobilized on, enclosed in, partially enclosed in, or any combination thereof, the synthetic particle. The synthetic particle can be disruptable. The synthetic particle can comprise a bead. The bead can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The synthetic particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. The synthetic particle can comprise a disruptable hydrogel particle.

In some embodiments, each of the plurality of oligonucleotide barcodes comprises a linker functional group, the synthetic particle comprises a solid support functional group, and/or the support functional group and the linker functional group are associated with each other. The linker functional group and the support functional group can be individually selected from the group consisting of C6, biotin, streptavidin, primary amine(s), aldehyde(s), ketone(s), and any combination thereof.

BRIEF DESCRIPTION OF THE DRAWINGS

FIGS. 4C1-4C2 are other non-limiting exemplary synthetic particles associated with a plurality of oligonucleotide barcodes and a plurality of spacer oligonucleotides. FIGS. 4D1-4D2 are non-limiting exemplary synthetic particles associated with a plurality of oligonucleotide barcodes with target-specific target-binding regions. The synthetic particles illustrated in FIGS. 4D1-4D2 can comprise one or more of the plurality of spacer oligonucleotides illustrated in FIGS. 4B and 4C1-4C2 (not shown).

FIGS. 5A-5C shows a non-limiting exemplary comparison of an oligonucleotide barcode with a poly(dT) region capable of hybridizing to the poly(A) tail of an mRNA molecule (FIG. 5A), an oligonucleotide barcode with a target-specific target-binding region capable of binding to one or more targets of interests (FIG. 5B), and an oligonucleotide barcode with a poly(dT) region and a target-specific target-binding region (FIG. 5C).

DETAILED DESCRIPTION

Figure 1:
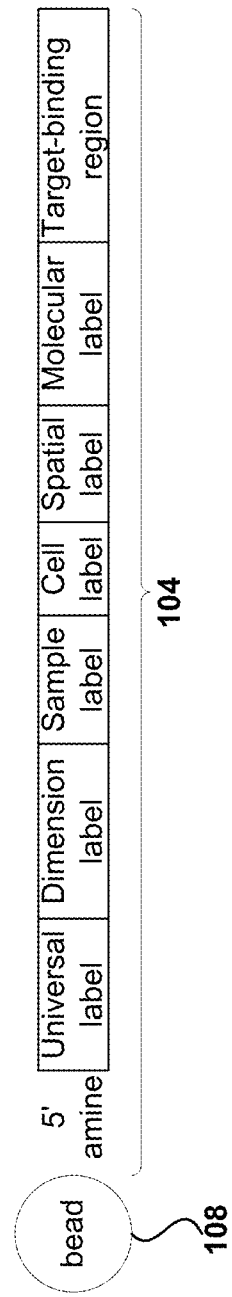
FIG. 1 illustrates a non-limiting exemplary barcode (e.g., a stochastic barcode).

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Determining numbers of nucleic acids or targets, for example messenger ribonucleotide acid (mRNA) molecules, is clinically important for determining, for example, the genes that are expressed in a cell at different stages of development or under different environmental conditions. However, it can be very challenging to determine the absolute number of nucleic acid molecules (e.g., mRNA molecules), especially when the number of molecules is very small. One method to determine the absolute number of molecules in a sample is digital polymerase chain reaction (PCR). Ideally, PCR produces an identical copy of a molecule at each cycle. However, PCR can have disadvantages such that each molecule replicates with a stochastic probability, and this probability varies by PCR cycle and gene sequence, resulting in amplification bias and inaccurate gene expression measurements.

Barcodes (e.g., stochastic barcodes) with unique molecular labels (MLs, also referred to as molecular indexes (MIs)) can be used to count the numbers of molecules. Barcodes with molecular labels that are unique for each cell label can be used to count the numbers of molecules in each cell. Non-limiting exemplary assays for barcoding include the Precise™ assay (Cellular Research, Inc. (Palo Alto, CA)), the Resolve™ assay (Cellular Research, Inc. (Palo Alto, CA)), or the Rhapsody™ assay (Becton, Dickinson and Company (Franklin Lakes, NJ)). However, these methods and techniques can introduce errors, if uncorrected, may result in overestimated cell counts.

The Rhapsody™ assay can utilize a non-depleting pool of barcodes (e.g., stochastic barcodes) with large number, for example 6561 to 65536, unique molecular labels on poly(T) oligonucleotides to hybridize to all poly(A)-mRNAs in a sample during the RT step. In addition to molecular labels, cell labels of the barcodes can be used to identify each single cell in each well of a microwell plate. A barcode can comprise a universal PCR priming site. During RT, target gene molecules react randomly with barcodes. Each target molecule can hybridize to a barcode (e.g., a stochastic barcode) resulting to generate barcoded complementary ribonucleotide acid (cDNA) molecules (e.g., stochastically barcoded cDNA molecules. After labeling, barcoded cDNA molecules from microwells of a microwell plate can be pooled into a single tube for PCR amplification and sequencing. Raw sequencing data can be analyzed to produce the numbers of barcodes with unique molecular labels.

Disclosed herein include embodiments of a synthetic particle. In some embodiments, the synthetic particles comprises: a first plurality of oligonucleotide barcodes; and a second plurality of oligonucleotide barcodes, wherein each of the first plurality of oligonucleotide barcodes and the second plurality of oligonucleotide barcodes comprises an identical cellular label sequence, and a molecular label sequence, wherein at least 10 of the first plurality of oligonucleotide barcodes and the second plurality of oligonucleotide barcodes comprise different molecular label sequences, wherein each of the first plurality of oligonucleotide barcodes comprises a target-binding region, and wherein each of the second plurality of oligonucleotide barcodes comprises a target-specific target-binding region. In some embodiments, the target-binding region of an oligonucleotide barcode of the first plurality of oligonucleotide barcodes comprises a target-specific target-binding region. In some embodiments, the target-binding region of an oligonucleotide barcode of the first plurality of oligonucleotide barcodes comprises a poly(dT) region. An oligonucleotide barcode of the second plurality of oligonucleotide barcodes can comprise a poly(dT) region.

Disclosed herein include embodiments of a kit or a composition. In some embodiments, the kit or composition comprises: a plurality of synthetic particles, wherein each synthetic particle comprises: a first plurality of oligonucleotide barcodes; and a second plurality of oligonucleotide barcodes, wherein each of the first plurality of oligonucleotide barcodes and the second plurality of oligonucleotide barcodes comprises an identical cellular label sequence and a molecular label sequence, wherein at least 10 of the first plurality of oligonucleotide barcodes and the second plurality of oligonucleotide barcodes comprise different molecular label sequences, wherein each of the first plurality of oligonucleotide barcodes comprises a target-binding region, and wherein each of the second plurality of oligonucleotide barcodes comprises a target-specific target-binding region; and optionally instructions for using the plurality of synthetic particles. In some embodiments, the kit comprises a buffer, one or more reagents for a reverse transcription reaction, one or more reagents for an amplification reaction, or a combination thereof. In some embodiments, the plurality of synthetic particles comprises at least 94 synthetic particles. The kit can comprise a plurality of partitions each comprising a synthetic particle of the plurality synthetic particles. The plurality of partitions can comprise microwells of a microwell array. The plurality of partitions ca comprise a plurality of droplets. In some embodiments, the target-binding region of an oligonucleotide barcode of the first plurality of oligonucleotide barcodes comprises a target-specific target-binding region. The target-binding region of an oligonucleotide barcode of the first plurality of oligonucleotide barcodes can comprise a poly(dT) region. An oligonucleotide barcode of the second plurality of oligonucleotide barcodes can comprise a poly(dT) region.

Disclosed herein include embodiments of a method for determining the numbers of targets in a sample. In some embodiments, the method comprises: barcoding copies of a first plurality of targets using a first plurality of oligonucleotide barcodes associated with a synthetic particle to generate copies of a first plurality of barcoded targets; barcoding copies of a second plurality of targets in a sample using a second plurality of oligonucleotide barcodes associated with the synthetic particle to generate copies of a second plurality of barcoded targets, wherein each of the first plurality of oligonucleotide barcodes and the second plurality of oligonucleotide barcodes comprises an identical cellular label sequence and a molecular label sequence, wherein at least 10 of the first plurality of oligonucleotide barcodes and the second plurality of oligonucleotide barcodes comprise different molecular label sequences, wherein each of the first plurality of oligonucleotide barcodes comprises a target-binding region, and wherein each of the second plurality of oligonucleotide barcodes comprises a target-specific target-binding region; and estimating the number of each of the first plurality of targets and/or the second plurality of targets using the molecular label sequences of the first plurality of oligonucleotide barcodes and the second plurality of oligonucleotide barcodes. In some embodiments, the target-binding region of an oligonucleotide barcode of the first plurality of oligonucleotide barcodes comprises a target-specific target-binding region. The target-binding region of an oligonucleotide barcode of the first plurality of oligonucleotide barcodes can comprise a poly(dT) region. An oligonucleotide barcode of the second plurality of oligonucleotide barcodes can comprise a poly(dT) region. In some embodiments, first plurality of targets comprises mRNA molecules of a cell, and wherein the second plurality of targets comprises DNA molecules of the cell. The first plurality of targets can comprise mRNA molecules of a cell, and the second plurality of targets can comprise RNA molecules of a virus, a bacterium, and/or a fungus infecting the cell.

Disclosed herein are embodiments of a particle associated with a plurality of oligonucleotides. In some embodiments, the particle is a synthetic particle. In some embodiments, the synthetic particle comprises: a plurality of oligonucleotide barcodes, wherein each of the plurality of oligonucleotide barcodes comprises an identical cellular label, a molecular label, and a target-binding region, and wherein at least 10 of the plurality of oligonucleotide barcodes comprise different molecular label sequences, and a first plurality of spacer oligonucleotides, wherein each of the first plurality of spacer oligonucleotides does not comprise the target-binding region. The ratio of the plurality of oligonucleotide barcodes and the first plurality of spacer oligonucleotides can range from 1:10 to 10:1. Each of the first plurality of spacer oligonucleotides can comprise a cellular label or a molecular label.

Also provided herein include embodiments of a kit comprising one or more synthetic particle of the disclosure. In some embodiments, the kit comprises: a plurality of synthetic particles, wherein each synthetic particle comprises: a plurality of oligonucleotide barcodes, wherein each of the plurality of oligonucleotide barcodes comprises an identical cellular label, a molecular label, and a target-binding region, and wherein at least 10 of the plurality of oligonucleotide barcodes comprise different molecular label sequences, and a first plurality of spacer oligonucleotides, wherein each of the first plurality of spacer oligonucleotides does not comprise the target-binding region. The kit can comprise: instructions for using the plurality of oligonucleotide barcodes.

Embodiments disclosed herein include methods for determining the numbers of targets in a sample. In some embodiments, the method comprises: barcoding copies of a plurality of targets in a sample using a plurality of oligonucleotide barcodes associated with a synthetic particle to generate copies of a plurality of barcoded targets, wherein each of the plurality of oligonucleotide barcodes comprises an identical cellular label, a molecular label, and a target-binding region, and wherein at least 10 of the plurality of oligonucleotide barcodes comprise different molecular label sequences, wherein the synthetic particle comprises a first plurality of spacer oligonucleotides, and wherein each of the first plurality of spacer oligonucleotides does not comprise the target-binding region; and estimating the number of each of the plurality of targets in the sample using the molecular labels of the plurality of oligonucleotide barcodes.

Disclosed herein are embodiments of a method for capturing targets in a sample. In some embodiments, the method comprises: hybridizing copies of a plurality of targets in a sample using a plurality of oligonucleotide barcodes associated with a synthetic particle to generate copies of a plurality of barcoded targets, wherein each of the plurality of oligonucleotide barcodes comprises an identical cellular label, a molecular label, and a target-binding region, and wherein at least 10 of the plurality of oligonucleotide barcodes comprise different molecular label sequences, wherein the synthetic particle comprises a first plurality of spacer oligonucleotides, and wherein each of the first plurality of spacer oligonucleotides does not comprise the target-binding region.

Some Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, NY 1989). For purposes of the present disclosure, the following terms are defined below.

As used herein, the term "adaptor" can mean a sequence to facilitate amplification or sequencing of associated nucleic acids. The associated nucleic acids can comprise target nucleic acids. The associated nucleic acids can comprise one or more of spatial labels, target labels, sample labels, indexing label, barcodes, stochastic barcodes, or molecular labels. The adapters can be linear. The adaptors can be pre-adenylated adapters. The adaptors can be double- or single-stranded. One or more adaptor can be located on the 5' or 3' end of a nucleic acid. When the adaptors comprise known sequences on the 5' and 3' ends, the known sequences can be the same or different sequences. An adaptor located on the 5' and/or 3' ends of a polynucleotide can be capable of hybridizing to one or more oligonucleotides immobilized on a surface. An adapter can, in some embodiments, comprise a universal sequence. A universal sequence can be a region of nucleotide sequence that is common to two or more nucleic acid molecules. The two or more nucleic acid molecules can have regions of different sequence. Thus, for example, the 5' adapters can comprise identical and/or universal nucleic acid sequences and the 3' adapters can comprise identical and/or universal sequences. A universal sequence that may be present in different members of a plurality of nucleic acid molecules can allow the replication or amplification of multiple different sequences using a single universal primer that is complementary to the universal sequence. Similarly, at least one, two (e.g., a pair) or more universal sequences that may be present in different members of a collection of nucleic acid molecules can allow the replication or amplification of multiple different sequences using at least one, two (e.g., a pair) or more single universal primers that are complementary to the universal sequences. Thus, a universal primer includes a sequence that can hybridize to such a universal sequence. The target nucleic acid sequence-bearing molecules may be modified to attach universal adapters (e.g., non-target nucleic acid sequences) to one or both ends of the different target nucleic acid sequences. The one or more universal primers attached to the target nucleic acid can provide sites for hybridization of universal primers. The one or more universal primers attached to the target nucleic acid can be the same or different from each other.

As used herein the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can be a physical association, direct or indirect. In some embodiments, two or more associated species are "tethered", "attached", or "immobilized" to one another or to a common solid or semisolid surface. An association may refer to covalent or non-covalent means for attaching labels to solid or semi-solid supports such as synthetic particles or beads. An association may be a covalent bond between a target and a label.

As used herein, the term "complementary" can refer to the capacity for precise pairing between two nucleotides. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. A first nucleotide sequence can be said to be the "complement" of a second sequence if the first nucleotide sequence is complementary to the second nucleotide sequence. A first nucleotide sequence can be said to be the "reverse complement" of a second sequence, if the first nucleotide sequence is complementary to a sequence that is the reverse (i.e., the order of the nucleotides is reversed) of the second sequence. As used herein, the terms "complement", "complementary", and "reverse complement" can be used interchangeably. It is understood from the disclosure that if a molecule can hybridize to another molecule it may be the complement of the molecule that is hybridizing.

As used herein, the term "digital counting" can refer to a method for estimating a number of target molecules in a sample. Digital counting can include the step of determining a number of unique labels that have been associated with targets in a sample. This stochastic methodology transforms the problem of counting molecules from one of locating and identifying identical molecules to a series of yes/no digital questions regarding detection of a set of predefined labels.

As used herein, the term "label" or "labels" can refer to nucleic acid codes associated with a target within a sample. A label can be, for example, a nucleic acid label. A label can be an entirely or partially amplifiable label. A label can be entirely or partially sequencable label. A label can be a portion of a native nucleic acid that is identifiable as distinct. A label can be a known sequence. A label can comprise a junction of nucleic acid sequences, for example a junction of a native and non-native sequence. As used herein, the term "label" can be used interchangeably with the terms, "index", "tag," or "label-tag." Labels can convey information. For example, in various embodiments, labels can be used to determine an identity of a sample, a source of a sample, an identity of a cell, and/or a target.

As used herein, the term "non-depleting reservoirs" can refer to a pool of stochastic barcodes made up of many different labels. A non-depleting reservoir can comprise large numbers of different stochastic barcodes such that when the non-depleting reservoir is associated with a pool of targets each target is likely to be associated with a unique stochastic barcode. The uniqueness of each labeled target molecule can be determined by the statistics of random choice, and depends on the number of copies of identical target molecules in the collection compared to the diversity of labels. The size of the resulting set of labeled target molecules can be determined by the stochastic nature of the barcoding process, and analysis of the number of stochastic barcodes detected then allows calculation of the number of target molecules present in the original collection or sample. When the ratio of the number of copies of a target molecule present to the number of unique stochastic barcodes is low, the labeled target molecules are highly unique (i.e. there is a very low probability that more than one target molecule will have been labeled with a given label).

As used herein, the term "nucleic acid" refers to a polynucleotide sequence, or fragment thereof. A nucleic acid can comprise nucleotides. A nucleic acid can be exogenous or endogenous to a cell. A nucleic acid can exist in a cell-free environment. A nucleic acid can be a gene or fragment thereof. A nucleic acid can be DNA. A nucleic acid can be RNA. A nucleic acid can comprise one or more analogs (e.g. altered backbone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g. rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudouridine, dihydrouridine, queuosine, and wyosine. "Nucleic acid", "polynucleotide, "target polynucleotide", and "target nucleic acid" can be used interchangeably.

A nucleic acid can comprise one or more modifications (e.g., a base modification, a backbone modification), to provide the nucleic acid with a new or enhanced feature (e.g., improved stability). A nucleic acid can comprise a nucleic acid affinity tag. A nucleoside can be a base-sugar combination. The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within nucleic acids, the phosphate groups can commonly be referred to as forming the internucleoside backbone of the nucleic acid. The linkage or backbone can be a 3' to 5' phosphodiester linkage.

A nucleic acid can comprise a modified backbone and/or modified internucleoside linkages. Modified backbones can include those that retain a phosphorus atom in the backbone and those that do not have a phosphorus atom in the backbone. Suitable modified nucleic acid backbones containing a phosphorus atom therein can include, for example, phosphorothioates, chiral phosphorothioates, phosphorodithioates, phosphotriesters, aminoalkyl phosphotriesters, methyl and other alkyl phosphonate such as 3'-alkylene phosphonates, 5'-alkylene phosphonates, chiral phosphonates, phosphinates, phosphoramidates including 3'-amino phosphoramidate and aminoalkyl phosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage.

A nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

A nucleic acid can comprise a nucleic acid mimetic. The term "mimetic" can be intended to include polynucleotides wherein only the furanose ring or both the furanose ring and the internucleotide linkage are replaced with non-furanose groups, replacement of only the furanose ring can be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

A nucleic acid can comprise linked morpholino units (i.e. morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C, 4'-C-oxymethylene linkage thereby forming a bicyclic sugar moiety. The linkage can be a methylene (—$CH_2$—), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A nucleic acid may also include nucleobase (often referred to simply as "base") modifications or substitutions. As used herein, "unmodified" or "natural" nucleobases can include the purine bases, (e.g. adenine (A) and guanine (G)), and the pyrimidine bases, (e.g. thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine (1H-pyrimido(5, 4-b)(1,4)benzoxazin-2(3H)-one), phenothiazine cytidine (1H-pyrimido(5,4-b)(1,4)benzothiazin-2(3H)-one),
G-clamps such as a substituted phenoxazine cytidine (e.g. 9-(2-aminoethoxy)-H-pyrimido(5,4-(b) (1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo [2,3-d]pyrimidin-2-one).

As used herein, the term "sample" can refer to a composition comprising targets. Suitable samples for analysis by the disclosed methods, devices, and systems include cells, tissues, organs, or organisms.

As used herein, the term "sampling device" or "device" can refer to a device which may take a section of a sample and/or place the section on a substrate. A sample device can refer to, for example, a fluorescence activated cell sorting (FACS) machine, a cell sorter machine, a biopsy needle, a biopsy device, a tissue sectioning device, a microfluidic device, a blade grid, and/or a microtome.

As used herein, the term "solid support" can refer to discrete solid or semi-solid surfaces to which a plurality of stochastic barcodes may be attached. A solid support may encompass any type of solid, porous, or hollow sphere, ball, bearing, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. A plurality of solid supports spaced in an array may not comprise a substrate. A solid support may be a particle, such as a synthetic particle or a bead.

A solid support can refer to a "substrate." A substrate can be a type of solid support. A substrate can refer to a continuous solid or semi-solid surface on which the methods of the disclosure may be performed. A substrate can refer to an array, a cartridge, a chip, a device, and a slide, for example.

As used here, the term, "spatial label" can refer to a label which can be associated with a position in space.

As used herein, the term "stochastic barcode" can refer to a polynucleotide sequence comprising labels. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "gene-specific stochastic barcode" can refer to a polynucleotide sequence comprising labels and a target-binding region that is gene-specific. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "stochastic barcoding" can refer to the random labeling (e.g., barcoding) of nucleic acids. Stochastic barcoding can utilize a recursive Poisson strategy to associate and quantify labels associated with targets. As used herein, the term "stochastic barcoding" can be used interchangeably with "gene-specific stochastic barcoding."

As used here, the term "target" can refer to a composition which can be associated with a stochastic barcode. Exemplary suitable targets for analysis by the disclosed methods, devices, and systems include oligonucleotides, DNA, RNA, mRNA, microRNA, tRNA, and the like. Targets can be single or double stranded. In some embodiments targets can be proteins. In some embodiments targets are lipids.

As used herein, the term "reverse transcriptases" can refer to a group of enzymes having reverse transcriptase activity (i.e., that catalyze synthesis of DNA from an RNA template). In general, such enzymes include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants or derivatives thereof. Non-retroviral reverse transcriptases include non-LTR retrotransposon reverse transcriptases, retroplasmid reverse transcriptases, retron reverse transciptases, and group II intron reverse transcriptases. Examples of group II intron reverse transcriptases include the *Lactococcus lactis* Ll.LtrB intron reverse transcriptase, the *Thermosynechococcus elongatus* TeI4c intron reverse transcriptase, or the *Geobacillus stearothermophilus* GsI-IIC intron reverse transcriptase. Other classes of reverse transcriptases can include many classes of non-retroviral reverse transcriptases (i.e., retrons, group II introns, and diversity-generating retroelements among others).

Disclosed herein are systems and methods for identifying a signal cell label. In some embodiments, the method comprises: (a) stochastically barcoding a plurality of targets in a sample of cells using a plurality of stochastic barcodes to create a plurality of stochastically barcoded targets, wherein each of the plurality of stochastic barcodes comprises a cell label and a molecular label; (b) obtaining sequencing data of the plurality of stochastically barcoded targets; (c) determining the numbers of molecular labels with distinct sequences associated with each of the cell labels of the plurality of stochastic barcodes; (d) determining a rank of each of the cell labels of the plurality of stochastic barcodes based on the number of molecular labels with distinct sequences associated with each of the cell labels; (e) generating a cumulative sum plot based on the number of molecular labels with distinct sequences associated with each of the cell labels determined in (c) and the rank of each of the cell labels determined in (d); (f) generating a second derivative plot of the cumulative sum plot; (g) determining a minimum of the second derivative plot of the cumulative sum plot, wherein the minimum of the second derivative plot corresponds to a cell label threshold; and (h) identifying each of the cell labels as a signal cell label or a noise cell label based on the number of molecular labels with distinct sequences associated with each of the cell labels determined in (c) and the cell label threshold determined in (g).

Barcodes

Barcoding, such as stochastic barcoding, has been described in, for example, Fu et al., *Proc Natl Acad Sci U.S.A.*, 2011 May 31, 108(22):9026-31; U.S. Patent Application Publication No. US2011/0160078; Fan et al., *Science*, 2015 Feb. 6, 347(6222):1258367; US Patent Application Publication No. US2015/0299784; and PCT Application Publication No. WO2015/031691; the content of each of these, including any supporting or supplemental information or material, is incorporated herein by reference in its entirety. In some embodiments, the barcode disclosed herein can be a stochastic barcode which can be a polynucleotide sequence that may be used to stochastically label (e.g., barcode, tag) a target. Barcodes can be referred to stochastic barcodes if the ratio of the number of different barcode sequences of the stochastic barcodes and the number of occurrence of any of the targets to be labeled can be, or be about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be, for example, an mRNA species comprising mRNA molecules with identical or nearly identical sequences. Barcodes can be referred to as stochastic barcodes if the ratio of the number of different barcode sequences of the stochastic barcodes and the number of occurrence of any of the targets to be labeled is at least, or is at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1. Barcode sequences of stochastic barcodes can be referred to as molecular labels.

A barcode, for example a stochastic barcode, can comprise one or more labels. Exemplary labels can include a universal label, a cell label, a barcode sequence (e.g., a molecular label), a sample label, a plate label, a spatial label, and/or a pre-spatial label. FIG. 1 illustrates an exemplary barcode 104 with a spatial label. The barcode 104 can comprise a 5' amine that may link the barcode to a solid support 108. The barcode can comprise a universal label, a dimension label, a spatial label, a cell label, and/or a molecular label. The order of different labels (including but not limited to the universal label, the dimension label, the spatial label, the cell label, and the molecule label) in the barcode can vary. For example, as shown in FIG. 1, the universal label may be the 5'-most label, and the molecular label may be the 3'-most label. The spatial label, dimension label, and the cell label may be in any order. In some embodiments, the universal label, the spatial label, the dimension label, the cell label, and the molecular label are in any order. The barcode can comprise a target-binding region. The target-binding region can interact with a target (e.g., target nucleic acid, RNA, mRNA, DNA) in a sample. For example, a target-binding region can comprise an oligo (dT) sequence which can interact with poly(A) tails of mRNAs. In some instances, the labels of the barcode (e.g., universal label, dimension label, spatial label, cell label, and barcode sequence) may be separated by 1, 2, 3, 4, 5, 6, 7, 8, 9, 10, 11, 12, 13, 14, 15, 16, 17, 18, 19, 20, or more nucleotides.

A label, for example the cell label, can comprise a unique set of nucleic acid sub-sequences of defined length, e.g. seven nucleotides each (equivalent to the number of bits used in some Hamming error correction codes), which can be designed to provide error correction capability. The set of error correction sub-sequences comprise seven nucleotide sequences can be designed such that any pairwise combination of sequences in the set exhibits a defined "genetic distance" (or number of mismatched bases), for example, a set of error correction sub-sequences can be designed to exhibit a genetic distance of three nucleotides. In this case, review of the error correction sequences in the set of sequence data for labeled target nucleic acid molecules (described more fully below) can allow one to detect or correct amplification or sequencing errors. In some embodiments, the length of the nucleic acid sub-sequences used for creating error correction codes can vary, for example, they can be, or be about 1, 2, 3, 4, 5, 6, 7, 8, 9, 10, 15, 20, 30, 31, 40, 50, or a number or a range between any two of these values, nucleotides in length. In some embodiments, nucleic acid sub-sequences of other lengths can be used for creating error correction codes.

The barcode can comprise a target-binding region. The target-binding region can interact with a target in a sample. The target can be, or comprise, ribonucleic acids (RNAs), messenger RNAs (mRNAs), microRNAs, small interfering RNAs (siRNAs), RNA degradation products, RNAs each comprising a poly(A) tail, or any combination thereof. In some embodiments, the plurality of targets can include deoxyribonucleic acids (DNAs).

In some embodiments, a target-binding region can comprise an oligo(dT) sequence which can interact with poly(A) tails of mRNAs. One or more of the labels of the barcode (e.g., the universal label, the dimension label, the spatial label, the cell label, and the barcode sequence (e.g., a molecular label)) can be separated by one or more spacers from another one or two of the remaining labels of the barcode. The spacer can be, for example, 1, 2, 3, 4, 5, 6, 7, 8, 9, 10, 11, 12, 13, 14, 15, 16, 17, 18, 19, 20, or more nucleotides in length. In some embodiments, none of the labels of the barcode is separated by spacer.

Universal Labels

A barcode can comprise one or more universal labels. In some embodiments, the one or more universal labels can be the same for all barcodes in the set of barcodes attached to a given solid support. In some embodiments, the one or more universal labels can be the same for all barcodes attached to a plurality of particles (e.g., synthetic particles such as beads). In some embodiments, a universal label can comprise a nucleic acid sequence that is capable of hybridizing to a sequencing primer. Sequencing primers can be used for sequencing barcodes comprising a universal label. Sequencing primers (e.g., universal sequencing primers) can comprise sequencing primers associated with high-throughput sequencing platforms. In some embodiments, a universal label can comprise a nucleic acid sequence that is capable of hybridizing to a PCR primer. In some embodiments, the universal label can comprise a nucleic acid sequence that is capable of hybridizing to a sequencing primer and a PCR primer. The nucleic acid sequence of the universal label that is capable of hybridizing to a sequencing or PCR primer can be referred to as a primer binding site. A universal label can comprise a sequence that can be used to initiate transcription of the barcode. A universal label can comprise a sequence that can be used for extension of the barcode or a region within the barcode. A universal label can be, or be about, 1, 2, 3, 4, 5, 10, 15, 20, 25, 30, 35, 40, 45, 50, or a number or a range between any two of these values, nucleotides in length. For example, a universal label can comprise at least about 10 nucleotides. A universal label can be at least, or at most, 1, 2, 3, 4, 5, 10, 15, 20, 25, 30, 35, 40, 45, 50, 100, 200, or 300 nucleotides in length. In some embodiments, a cleavable linker or modified nucleotide can be part of the universal label sequence to enable the barcode to be cleaved off from the support.

Dimension Labels

A barcode can comprise one or more dimension labels. In some embodiments, a dimension label can comprise a nucleic acid sequence that provides information about a dimension in which the labeling (e.g., stochastic labeling) occurred. For example, a dimension label can provide information about the time at which a target was stochastically barcoded. A dimension label can be associated with a time of barcoding (e.g., stochastic barcoding) in a sample. A dimension label can be activated at the time of labeling. Different dimension labels can be activated at different times. The dimension label provides information about the order in which targets, groups of targets, and/or samples were stochastically barcoded. For example, a population of cells can be stochastically barcoded at the G0 phase of the cell cycle. The cells can be pulsed again with barcodes (e.g., stochastic barcodes) at the G1 phase of the cell cycle. The cells can be pulsed again with barcodes at the S phase of the cell cycle, and so on. Barcodes at each pulse (e.g., each phase of the cell cycle), can comprise different dimension labels. In this way, the dimension label provides information about which targets were labelled at which phase of the cell cycle. Dimension labels can interrogate many different biological times. Exemplary biological times can include, but are not limited to, the cell cycle, transcription (e.g., transcription initiation), and transcript degradation. In another example, a sample (e.g., a cell, a population of cells) can be stochastically labeled before and/or after treatment with a drug and/or therapy. The changes in the number of copies of distinct targets can be indicative of the sample's response to the drug and/or therapy.

A dimension label can be activatable. An activatable dimension label can be activated at a specific time point. The activatable label can be, for example, constitutively activated (e.g., not turned off). The activatable dimension label can be, for example, reversibly activated (e.g., the activatable dimension label can be turned on and turned off). The dimension label can be, for example, reversibly activatable at least 1, 2, 3, 4, 5, 6, 7, 8, 9, 10, or more times. The dimension label can be reversibly activatable, for example, at least 1, 2, 3, 4, 5, 6, 7, 8, 9, 10, or more times. In some embodiments, the dimension label can be activated with fluorescence, light, a chemical event (e.g., cleavage, ligation of another molecule, addition of modifications (e.g., pegylated, sumoylated, acetylated, methylated, deacetylated, demethylated), a photochemical event (e.g., photocaging), and introduction of a non-natural nucleotide.

The dimension label can, in some embodiments, be identical for all barcodes (e.g., stochastic barcodes) attached to a given solid support (e.g., a synthetic particle, such as a bead), but different for different solid supports (e.g., synthetic particles). In some embodiments, at least 60%, 70%, 80%, 85%, 90%, 95%, 97%, 99%, or 100% of barcodes on the same solid support can comprise the same dimension label. In some embodiments, at least 60% of barcodes on the same solid support can comprise the same dimension label. In some embodiments, at least 95% of barcodes on the same solid support can comprise the same dimension label.

There can be as many as $10^6$ or more unique dimension label sequences represented in a plurality of solid supports (e.g., synthetic particles). A dimension label can be, or be about 1, 2, 3, 4, 5, 10, 15, 20, 25, 30, 35, 40, 45, 50, or a number or a range between any two of these values, nucleotides in length. A dimension label can be at least, or at most, 1, 2, 3, 4, 5, 10, 15, 20, 25, 30, 35, 40, 45, 50, 100, 200, or 300 nucleotides in length. A dimension label can comprise between about 5 to about 200 nucleotides. A dimension label can comprise between about 10 to about 150 nucleotides. A dimension label can comprise between about 20 to about 125 nucleotides in length.

Spatial Labels

A barcode can comprise one or more spatial labels. In some embodiments, a spatial label can comprise a nucleic acid sequence that provides information about the spatial orientation of a target molecule which is associated with the barcode. A spatial label can be associated with a coordinate in a sample. The coordinate can be a fixed coordinate. For example a coordinate can be fixed in reference to a substrate. A spatial label can be in reference to a two or three-dimensional grid. A coordinate can be fixed in reference to a landmark. The landmark can be identifiable in space. A landmark can be a structure which can be imaged. A landmark can be a biological structure, for example an anatomical landmark. A landmark can be a cellular landmark, for instance an organelle. A landmark can be a non-natural landmark such as a structure with an identifiable identifier such as a color code, bar code, magnetic property, fluorescents, radioactivity, or a unique size or shape. A spatial label can be associated with a physical partition (e.g. a well, a container, a microsphere, a tube, a microcapsule, or a droplet). In some embodiments, multiple spatial labels are used together to encode one or more positions in space.

The spatial label can be identical for all barcodes attached to a given solid support (e.g., a synthetic particle such as a bead), but different for different solid supports (e.g., synthetic particles). In some embodiments, the percentage of barcodes on the same solid support comprising the same spatial label can be, or be about, 60%, 70%, 80%, 85%, 90%, 95%, 97%, 99%, 100%, or a number or a range between any two of these values. In some embodiments, the percentage of barcodes on the same solid support comprising the same spatial label can be at least, or at most, 60%, 70%, 80%, 85%, 90%, 95%, 97%, 99%, or 100%. In some embodiments, at least 60% of barcodes on the same solid support can comprise the same spatial label. In some embodiments, at least 95% of barcodes on the same solid support can comprise the same spatial label.

There can be as many as $10^6$ or more unique spatial label sequences represented in a plurality of solid supports (e.g., synthetic particles such as a bead). A spatial label can be, or be about, 1, 2, 3, 4, 5, 10, 15, 20, 25, 30, 35, 40, 45, 50, or a number or a range between any two of these values, nucleotides in length. A spatial label can be at least, or at most, 1, 2, 3, 4, 5, 10, 15, 20, 25, 30, 35, 40, 45, 50, 100, 200, or 300 nucleotides in length. A spatial label can comprise between about 5 to about 200 nucleotides. A spatial label can comprise between about 10 to about 150 nucleotides. A spatial label can comprise between about 20 to about 125 nucleotides in length.

Cell Labels

A barcode can comprise one or more cell labels. In some embodiments, a cell label can comprise a nucleic acid sequence that provides information for determining which target nucleic acid originated from which cell. In some embodiments, the cell label is identical for all barcodes attached to a given solid support (e.g., a synthetic particle such as a bead), but different for different solid supports (e.g., synthetic particles). In some embodiments, the percentage of barcodes on the same solid support comprising the same cell label can be, or be about 60%, 70%, 80%, 85%, 90%, 95%, 97%, 99%, 100%, or a number or a range between any two of these values. In some embodiments, the percentage of barcodes on the same solid support comprising the same cell label can be, or be about 60%, 70%, 80%, 85%, 90%, 95%, 97%, 99%, or 100%. For example, at least 60% of barcodes on the same solid support can comprise the same cell label. As another example, at least 95% of barcodes on the same solid support can comprise the same cell label.

There can be as many as $10^6$ or more unique cell label sequences represented in a plurality of solid supports (e.g., synthetic particles). A cell label can be, or be about, 1, 2, 3, 4, 5, 10, 15, 20, 25, 30, 35, 40, 45, 50, or a number or a range between any two of these values, nucleotides in length. A cell label can be at least, or at most, 1, 2, 3, 4, 5, 10, 15, 20, 25, 30, 35, 40, 45, 50, 100, 200, or 300 nucleotides in length. For example, a cell label can comprise between about 5 to about 200 nucleotides. As another example, a cell label can comprise between about 10 to about 150 nucleotides. As yet another example, a cell label can comprise between about 20 to about 125 nucleotides in length.

Barcode Sequences

A barcode can comprise one or more barcode sequences. In some embodiments, a barcode sequence can comprise a nucleic acid sequence that provides identifying information for the specific type of target nucleic acid species hybridized to the barcode. A barcode sequence can comprise a nucleic acid sequence that provides a counter (e.g., that provides a rough approximation) for the specific occurrence of the target nucleic acid species hybridized to the barcode (e.g., target-binding region).

In some embodiments, a diverse set of barcode sequences are attached to a given solid support (e.g., a synthetic particle, such as a bead). In some embodiments, there can be, or be about, $10^2$, $10^3$, $10^4$, $10^5$, $10^6$, $10^7$, $10^8$, $10^9$, or a number or a range between any two of these values, unique molecular label sequences. For example, a plurality of barcodes can comprise about 6561 barcodes sequences with distinct sequences. As another example, a plurality of barcodes can comprise about 65536 barcode sequences with distinct sequences. In some embodiments, there can be at least, or at most, $10^2$, $10^3$, $10^4$, $10^5$, $10^6$, $10^7$, $10^8$, or $10^9$, unique barcode sequences. The unique molecular label sequences can be attached to a given solid support (e.g., a synthetic particle).

A barcode can be, or be about, 1, 2, 3, 4, 5, 10, 15, 20, 25, 30, 35, 40, 45, 50, or a number or a range between any two of these values, nucleotides in length. A barcode can be at least, or at most, 1, 2, 3, 4, 5, 10, 15, 20, 25, 30, 35, 40, 45, 50, 100, 200, or 300 nucleotides in length.

Molecular Labels

A stochastic barcode can comprise one or more molecular labels. Molecular labels can include barcode sequences. In some embodiments, a molecular label can comprise a nucleic acid sequence that provides identifying information for the specific type of target nucleic acid species hybridized to the stochastic barcode. A molecular label can comprise a nucleic acid sequence that provides a counter for the specific occurrence of the target nucleic acid species hybridized to the stochastic barcode (e.g., target-binding region).

In some embodiments, a diverse set of molecular labels are attached to a given solid support (e.g., a synthetic particle such as a bead). In some embodiments, there can be, or be about, $10^2$, $10^3$, $10^4$, $10^5$, $10^6$, $10^7$, $10^8$, $10^9$, or a number or a range of unique molecular label sequences. For example, a plurality of stochastic barcodes can comprise about 6561 molecular labels with distinct sequences. As another example, a plurality of stochastic barcodes can comprise about 65536 molecular labels with distinct sequences. In some embodiments, there can be at least, or at most, $10^2$, $10^3$, $10^4$, $10^5$, $10^6$, $10^7$, $10^8$, or $10^9$, unique molecular label sequences. Stochastic barcodes with the unique molecular label sequences can be attached to a given solid support (e.g., a synthetic particle).

For stochastic barcoding using a plurality of stochastic barcodes, the ratio of the number of different molecular label sequences and the number of occurrence of any of the targets can be, or be about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be an mRNA species comprising mRNA molecules with identical or nearly identical sequences. In some embodiments, the ratio of the number of different molecular label sequences and the number of occurrence of any of the targets is at least, or at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1.

A molecular label can be, or be about, 1, 2, 3, 4, 5, 10, 15, 20, 25, 30, 35, 40, 45, 50, or a number or a range between any two of these values, nucleotides in length. A molecular label can be at least, or at most, 1, 2, 3, 4, 5, 10, 15, 20, 25, 30, 35, 40, 45, 50, 100, 200, or 300 nucleotides in length.

Target-Binding Region

A barcode can comprise one or more target-binding regions, such as capture probes. In some embodiments, a target-binding region can hybridize with a target of interest. In some embodiments, a target-binding region can comprise a nucleic acid sequence that hybridizes specifically to a target (e.g. target nucleic acid, such as a cellular nucleic acid to be analyzed). For example, a target-binding region can hybridize to a target nucleic acid at a specific gene sequence. In some embodiments, a target-binding region can comprise a nucleic acid sequence that can attach (e.g., hybridize) to a specific location of a specific target nucleic acid. In some embodiments, the target-binding region can comprise a nucleic acid sequence that is capable of specific hybridization to a restriction enzyme site overhang (e.g. an EcoRI sticky-end overhang). The barcode can then ligate to any nucleic acid molecule comprising a sequence complementary to the restriction site overhang.

In some embodiments, a target-binding region can comprise a non-specific target nucleic acid sequence. A non-specific target nucleic acid sequence can refer to a sequence that can bind to multiple target nucleic acids, independent of the specific sequence of the target nucleic acid. For example, target-binding region can comprise a random multimer sequence, or an oligo(dT) sequence that hybridizes to the poly(A) tails on mRNA molecules. A random multimer sequence can be, for example, a random dimer, trimer, quatramer, pentamer, hexamer, septamer, octamer, nonamer, decamer, or higher multimer sequence of any length. In some embodiments, the target-binding region is the same for all barcodes attached to a given synthetic particle (e.g., a bead). In some embodiments, the target-binding regions for the plurality of barcodes attached to a given synthetic particle can comprise two or more different target binding sequences. A target-binding region can be, or be about, 5, 10, 15, 20, 25, 30, 35, 40, 45, 50, or a number or a range between any two of these values, nucleotides in length. A target-binding region can be at most about 5, 10, 15, 20, 25, 30, 35, 40, 45, 50, or more nucleotides in length.

In some embodiments, a target-binding region can comprise an oligo(dT) which can hybridize with mRNAs comprising polyadenylated ends. A target-binding region can be gene-specific. For example, a target-binding region can be configured to hybridize to a specific region of a target. A target-binding region can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these values, nucleotides in length. A target-binding region can be at least, or at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30, nucleotides in length. A target-binding region can be about 5-30 nucleotides in length. When a barcode comprises a gene-specific target-binding region, the barcode can be referred to herein as a gene-specific barcode.

In some embodiments, a barcode does not include a target-binding region. In some embodiments, a barcode includes a region corresponding to a target-binding region with a sequence that has a low binding affinity (e.g., does not bind) to some, most, substantially all, or all of the mRNA molecules in a cell or cells of a sample. For example, a barcode can comprise a region that corresponds to a target-binding region can have a sequence that does not bind to mRNA molecules of interest. If the target-binding region of a first barcode comprises an oligo(dT) sequence that is capable of hybridizing to the poly(A) tail of an mRNA molecule, the corresponding region of a second barcode can include, for example, a sequence that is not similar, or substantially similar, to a poly(dT) sequence. If the target-binding region of a first barcode comprises a target-binding region with a sequence that is capable of hybridizing specifically to a particular gene sequence, the corresponding region of a second barcode can include, for example, a sequence that is not similar, or substantially similar, to the target-binding region.

Orientation Property

A barcode can comprise one or more orientation properties which can be used to orient (e.g., align) the barcodes. A barcode can comprise a moiety for isoelectric focusing. Different barcodes can comprise different isoelectric focusing points. When these barcodes are introduced to a sample, the sample can undergo isoelectric focusing in order to orient the barcodes into a known way. In this way, the orientation property can be used to develop a known map of barcodes in a sample. Exemplary orientation properties can include, electrophoretic mobility (e.g., based on size of the barcode), isoelectric point, spin, conductivity, and/or self-assembly. For example, barcodes with an orientation property of self-assembly, can self-assemble into a specific orientation (e.g., nucleic acid nanostructure) upon activation.

Affinity Property

A barcode can comprise one or more affinity properties. For example, a spatial label can comprise an affinity property. An affinity property can include a chemical and/or biological moiety that can facilitate binding of the barcode to another entity (e.g., cell receptor). For example, an affinity property can comprise an antibody, for example, an antibody specific for a specific moiety (e.g., receptor) on a sample. In some embodiments, the antibody can guide the barcode to a specific cell type or molecule. Targets at and/or near the specific cell type or molecule can be stochastically labeled. The affinity property can, in some embodiments, provide spatial information in addition to the nucleotide sequence of the spatial label because the antibody can guide the barcode to a specific location. The antibody can be a therapeutic antibody, for example a monoclonal antibody or a polyclonal antibody. The antibody can be humanized or chimeric. The antibody can be a naked antibody or a fusion antibody.

The antibody can be a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

The antibody fragment can be, for example, a portion of an antibody such as F(ab')2, Fab', Fab, Fv, sFv and the like. In some embodiments, the antibody fragment can bind with the same antigen that is recognized by the full-length antibody. The antibody fragment can include isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins"). Exemplary antibodies can include, but are not limited to, antibodies for cancer cells, antibodies for viruses, antibodies that bind to cell surface receptors (CD8, CD34, CD45), and therapeutic antibodies.

Universal Adaptor Primer

A barcode can comprise one or more universal adaptor primers. For example, a gene-specific barcode, such as a gene-specific stochastic barcode, can comprise a universal adaptor primer. A universal adaptor primer can refer to a nucleotide sequence that is universal across all barcodes. A universal adaptor primer can be used for building gene-specific barcodes. A universal adaptor primer can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these nucleotides in length. A universal adaptor primer can be at least, or at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30 nucleotides in length. A universal adaptor primer can be from 5-30 nucleotides in length.

Linker

When a barcode comprises more than one of a type of label (e.g., more than one cell label or more than one barcode sequence, such as one molecular label), the labels may be interspersed with a linker label sequence. A linker label sequence can be at least about 5, 10, 15, 20, 25, 30, 35, 40, 45, 50, or more nucleotides in length. A linker label sequence can be at most about 5, 10, 15, 20, 25, 30, 35, 40, 45, 50, or more nucleotides in length. In some instances, a linker label sequence is 12 nucleotides in length. A linker label sequence can be used to facilitate the synthesis of the barcode. The linker label can comprise an error-correcting (e.g., Hamming) code.

Solid Supports

Barcodes, such as stochastic barcodes, disclosed herein can, in some embodiments, be associated with a solid support. The solid support can be, for example, a particle or a synthetic particle. In some embodiments, some or all of the barcode sequence, such as molecular labels for stochastic barcodes (e.g., the first barcode sequences) of a plurality of barcodes (e.g., the first plurality of barcodes) on a solid support differ by at least one nucleotide. The cell labels of the barcodes on the same solid support can be the same. The cell labels of the barcodes on different solid supports can differ by at least one nucleotide. For example, first cell labels of a first plurality of barcodes on a first solid support can have the same sequence, and second cell labels of a second plurality of barcodes on a second solid support can have the same sequence. The first cell labels of the first plurality of barcodes on the first solid support and the second cell labels of the second plurality of barcodes on the second solid support can differ by at least one nucleotide. A cell label can be, for example, about 5-20 nucleotides long. A barcode sequence can be, for example, about 5-20 nucleotides long. The synthetic particle can be, for example, a bead.

The synthetic particle can be, for example, a silica gel bead, a controlled pore glass bead, a magnetic bead, a Dynabead, a Sephadex/Sepharose bead, a cellulose bead, a polystyrene bead, or any combination thereof. The synthetic particle can comprise a material such as polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, or any combination thereof.

In some embodiments, a synthetic particle can be a polymeric particle, for example a deformable particle or a gel particle, functionalized with barcodes or stochastic barcodes (such as gel beads from 10× Genomics (San Francisco, CA). In some implementation, a gel particle can comprise one or more polymer-based gels. Gel particles can be generated, for example, by encapsulating one or more polymeric precursors into droplets. Upon exposure of the polymeric precursors to an accelerator (e.g., tetramethylethylenediamine (TEMED)), a gel particle may be generated.

In some embodiments, the particle can be degradable. For example, the polymeric particle or bead can dissolve, melt, or degrade, for example, under a desired condition. The desired condition can include an environmental condition. The desired condition may result in the polymeric particle dissolving, melting, or degrading in a controlled manner. A gel particle may dissolve, melt, or degrade due to a chemical stimulus, a physical stimulus, a biological stimulus, a thermal stimulus, a magnetic stimulus, an electric stimulus, a light stimulus, or any combinations thereof.

Reagents, such as oligonucleotide barcodes, may be coupled/immobilized to the interior surface of a synthetic particle (e.g., the interior accessible via diffusion of an oligonucleotide barcode and/or materials used to generate an oligonucleotide barcode) and/or the outer surface of a gel particle or any other microcapsule described herein. The particle can be, for example, a gel bead. Association (e.g., coupling, or immobilization) may be via any form of chemical bonding (e.g., covalent bond, ionic bond) or physical phenomena (e.g., Van der Waals forces, dipole-dipole interactions, etc.). In some embodiments, association (e.g., coupling or immobilization) of a reagent to a particle or any other solid support (e.g., microcapsule) described herein may be reversible, such as, for example, via a labile moiety (e.g., via a chemical cross-linker, including chemical cross-linkers described herein). Upon application of a stimulus, the labile moiety may be cleaved and the immobilized reagent set free. In some embodiments, the labile moiety is a disulfide bond. For example, in the case where an oligonucleotide barcode is immobilized to a gel particle via a disulfide bond, exposure of the disulfide bond to a reducing agent can cleave the disulfide bond and free the oligonucleotide barcode from the particle. The labile moiety may be included as part of a gel particle, bead, or microcapsule, as part of a chemical linker that links a reagent to a gel bead or microcapsule, and/or as part of a reagent. In some embodiments, at least one barcode of the plurality of barcodes can be immobilized on the particle, partially immobilized on the particle, enclosed in the particle, partially enclosed in the particle, or any combination thereof.

In some embodiments, a particle (for example a gel bead) can comprise a wide range of different polymers including but not limited to: polymers, heat sensitive polymers, photosensitive polymers, magnetic polymers, pH sensitive polymers, salt-sensitive polymers, chemically sensitive polymers, polyelectrolytes, polysaccharides, peptides, proteins, and/or plastics. Polymers may include but are not limited to materials such as poly(N-isopropylacrylamide) (PNIPAAm), poly(styrene sulfonate) (PSS), poly(allyl amine) (PAAm), poly(acrylic acid) (PAA), poly(ethylene imine) (PEI), poly(diallyldimethyl-ammonium chloride) (PDADMAC), poly(pyrolle) (PPy), poly(vinylpyrrolidone) (PVPON), poly(vinyl pyridine) (PVP), poly(methacrylic acid) (PMAA), poly(methyl methacrylate) (PMMA), polystyrene (PS), poly(tetrahydrofuran) (PTHF), poly(phthaladehyde) (PTHF), poly(hexyl viologen) (PHV), poly(L-lysine) (PLL), poly(L-arginine) (PARG), poly(lactic-co-glycolic acid) (PLGA).

Numerous chemical stimuli can be used to trigger the disruption, dissolution, or degradation of the particles. Examples of these chemical changes may include, but are not limited to pH-mediated changes to the particle wall, disintegration of the particle wall via chemical cleavage of crosslink bonds, triggered depolymerization of the particle wall, and particle wall switching reactions. Bulk changes may also be used to trigger disruption of the particles.

Bulk or physical changes to the microcapsule or particles through various stimuli also offer many advantages in designing capsules to release reagents. Bulk or physical changes occur on a macroscopic scale, in which particle rupture is the result of mechano-physical forces induced by a stimulus. These processes may include, but are not limited to pressure induced rupture, particle wall melting, or changes in the porosity of the particle wall.

Biological stimuli may also be used to trigger disruption, dissolution, or degradation of particles. Generally, biological triggers resemble chemical triggers, but many examples use biomolecules, or molecules commonly found in living systems such as enzymes, peptides, saccharides, fatty acids, nucleic acids and the like. For example, particles may comprise polymers with peptide cross-links that are sensitive to cleavage by specific proteases. More specifically, one example may comprise a microcapsule comprising GFLGK peptide cross links. Upon addition of a biological trigger such as the protease Cathepsin B, the peptide cross links of the shell well are cleaved and the contents of the particles are released. In other cases, the proteases may be heat-activated. In another example, particles comprise a shell wall comprising cellulose. Addition of the hydrolytic enzyme chitosan serves as biologic trigger for cleavage of cellulosic bonds, depolymerization of the shell wall, and release of its inner contents.

The particles may also be induced to release their contents upon the application of a thermal stimulus. A change in temperature can cause a variety changes to the particles. A change in heat may cause melting of a particle such that the particle wall disintegrates. In other cases, the heat may increase the internal pressure of the inner components of the particle such that the particle ruptures or explodes. In still other cases, the heat may transform the particle into a shrunken dehydrated state. The heat may also act upon heat-sensitive polymers within the wall of a particle to cause disruption of the particle.

Inclusion of magnetic nanoparticles to the particle wall of microcapsules may allow triggered rupture of the particles as well as guide the particles in an array. A device of this disclosure may comprise magnetic particles for either purpose. In one example, incorporation of $Fe_3O_4$ nanoparticles into polyelectrolyte containing particles triggers rupture in the presence of an oscillating magnetic field stimulus.

A particle may also be disrupted, dissolved, or degraded as the result of electrical stimulation. Similar to magnetic particles described in the previous section, electrically sensitive particles can allow for both triggered rupture of the particles as well as other functions such as alignment in an electric field, electrical conductivity or redox reactions. In one example, particles containing electrically sensitive material are aligned in an electric field such that release of inner reagents can be controlled. In other examples, electrical fields may induce redox reactions within the particle wall itself that may increase porosity.

A light stimulus may also be used to disrupt the particles. Numerous light triggers are possible and may include systems that use various molecules such as nanoparticles and chromophores capable of absorbing photons of specific ranges of wavelengths. For example, metal oxide coatings can be used as capsule triggers. UV irradiation of polyelectrolyte capsules coated with $SiO_2$ may result in disintegration of the particle wall. In yet another example, photo switchable materials such as azobenzene groups may be incorporated in the particle wall. Upon the application of UV or visible light, chemicals such as these undergo a reversible cis-to-trans isomerization upon absorption of photons. In this aspect, incorporation of photon switches result in a particle wall that may disintegrate or become more porous upon the application of a light trigger.

Figure 2:
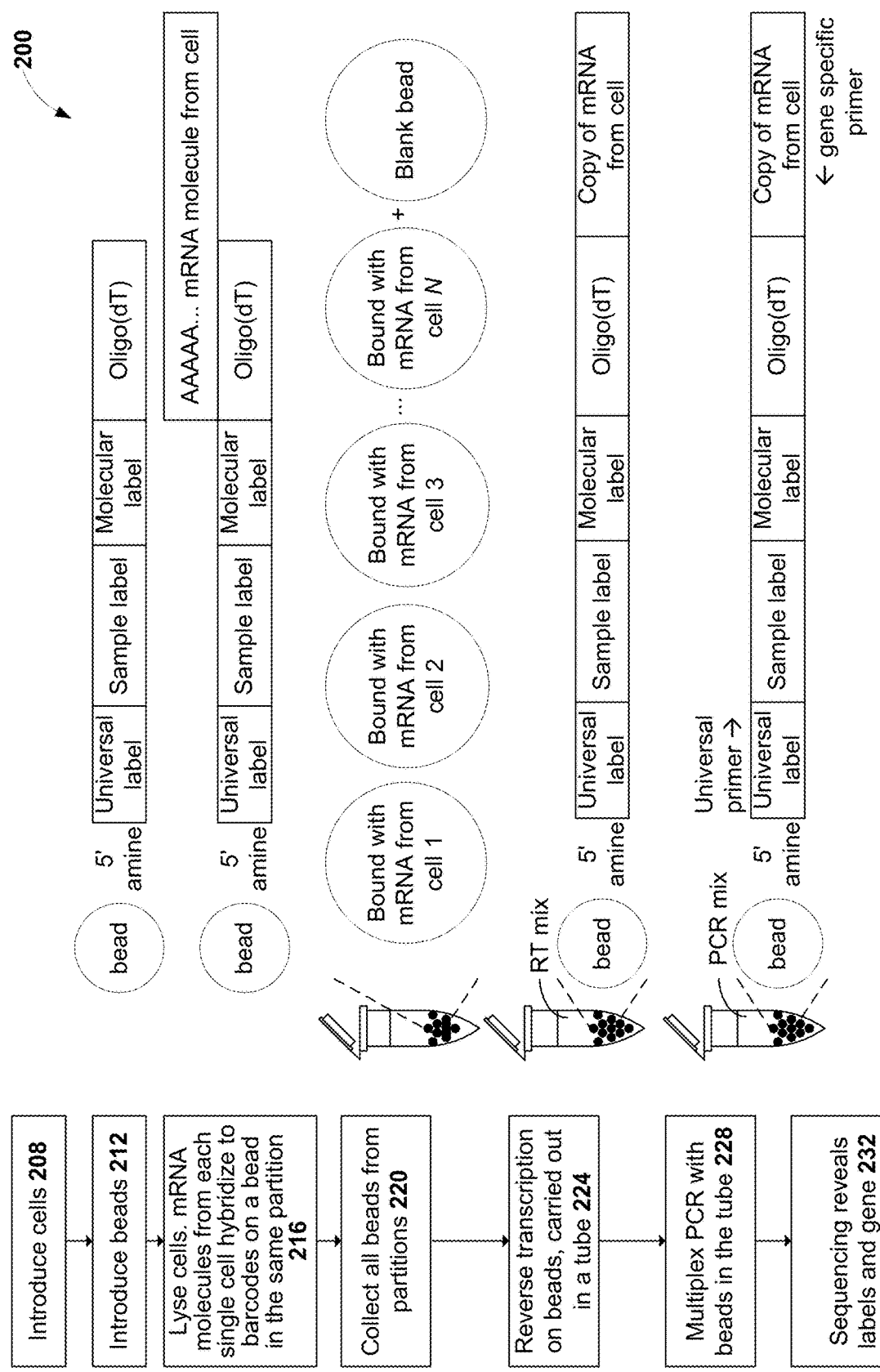
FIG. 2 shows a non-limiting exemplary workflow of barcoding and digital counting (e.g., stochastic barcoding and digital counting).

For example, in a non-limiting example of barcoding (e.g., stochastic barcoding) illustrated in FIG. 2, after introducing cells such as single cells onto a plurality of microwells of a microwell array at block 208, particles can be introduced onto the plurality of microwells of the microwell array at block 212. Each microwell can comprise one particle. The particles can comprise a plurality of barcodes. A barcode can comprise a 5' amine region attached to a particle. The barcode can comprise a universal label, a barcode sequence (e.g., a molecular label), a target-binding region, or any combination thereof.

The barcodes disclosed herein can be associated with (e.g., attached to) a solid support (e.g., a particle or a bead). The barcodes associated with a solid support can each comprise a barcode sequence selected from a group comprising at least 100 or 1000 barcode sequences with unique sequences. In some embodiments, different barcodes associated with a solid support can comprise barcode sequences of different sequences. In some embodiments, a percentage of barcodes associated with a solid support comprises the same cell label. For example, the percentage can be, or be about 60%, 70%, 80%, 85%, 90%, 95%, 97%, 99%, 100%, or a number or a range between any two of these values. As another example, the percentage can be at least, or at most 60%, 70%, 80%, 85%, 90%, 95%, 97%, 99%, or 100%. In some embodiments, barcodes associated with a solid support can have the same cell label. The barcodes associated with different solid supports can have different cell labels selected from a group comprising at least 100 or 1000 cell labels with unique sequences.

The barcodes disclosed herein can be associated to (e.g., attached to) a solid support (e.g., a particle, such as a bead). In some embodiments, stochastically barcoding the plurality of targets in the sample can be performed with a solid support including a plurality of synthetic particles associated with the plurality of barcodes. In some embodiments, the solid support can include a plurality of synthetic particles associated with the plurality of barcodes. The spatial labels of the plurality of barcodes on different solid supports can differ by at least one nucleotide. The solid support can, for example, include the plurality of barcodes in two dimensions or three dimensions. The synthetic particles can be beads. The particles can be silica gel beads, controlled pore glass beads, magnetic beads, Dynabeads, Sephadex/Sepharose beads, cellulose beads, polystyrene beads, or any combination thereof. The solid support can include a polymer, a matrix, a hydrogel, a needle array device, an antibody, or any combination thereof. In some embodiments, the solid supports can be free floating. In some embodiments, the solid supports can be embedded in a semi-solid or solid array. The barcodes may not be associated with solid supports. The barcodes can be individual nucleotides. The barcodes can be associated with a substrate.

As used herein, the terms "tethered," "attached," and "immobilized" are used interchangeably, and can refer to covalent or non-covalent means for attaching barcodes to a solid support. Any of a variety of different solid supports can be used as solid supports for attaching pre-synthesized barcodes or for in situ solid-phase synthesis of barcodes.

In some embodiments, the solid support is a particle, for example a bead. The particle can comprise one or more types of solid, porous, or hollow sphere, ball, bearing, cylinder, or other similar configuration which a nucleic acid can be immobilized (e.g., covalently or non-covalently). The particle can be, for example, composed of plastic, ceramic, metal, polymeric material, or any combination thereof. A particle can be, or comprise, a discrete particle that is spherical (e.g., microspheres) or have a non-spherical or irregular shape, such as cubic, cuboid, pyramidal, cylindrical, conical, oblong, or disc-shaped, and the like. In some embodiments, a particle can be non-spherical in shape.

The particles can comprise a variety of materials including, but not limited to, paramagnetic materials (e.g. magnesium, molybdenum, lithium, and tantalum), superparamagnetic materials (e.g. ferrite ($Fe_3O_4$; magnetite) nanoparticles), ferromagnetic materials (e.g. iron, nickel, cobalt, some alloys thereof, and some rare earth metal compounds), ceramic, plastic, glass, polystyrene, silica, methylstyrene, acrylic polymers, titanium, latex, Sepharose, agarose, hydrogel, polymer, cellulose, nylon, or any combination thereof.

In some embodiments, the particle (e.g., the particle to which the labels are attached) is a hydrogel bead. In some embodiments, the particle comprises hydrogel.

Some embodiments disclosed herein include one or more particles (for example beads). Each of the particles can comprise a plurality of oligonucleotides (e.g., barcodes). Each of the plurality of oligonucleotides can comprise a barcode sequence (e.g., a molecular label), a cell label, and a target-binding region (e.g., an oligo(dT) sequence, a gene-specific sequence, a random multimer, or a combination thereof). The cell label sequence of each of the plurality of oligonucleotides can be the same. The cell label sequences of oligonucleotides on different particles can be different such that the oligonucleotides on different particles can be identified. The number of different cell label sequences can be different in different implementations. In some embodiments, the number of cell label sequences can be, or be about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, a number or a range between any two of these values, or more. In some embodiments, the number of cell label sequences can be at least, or at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. In some embodiments, no more than 1, 2, 3, 4, 5, 6, 7, 8, 9, 10, 20, 30, 40, 50, 60, 70, 80, 90, 100, 200, 300, 400, 500, 600, 700, 800, 900, 1000, or more of the plurality of the particles include oligonucleotides with the same cell sequence. In some embodiment, the plurality of particles that include oligonucleotides with the same cell sequence can be at most 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10% or more. In some embodiments, none of the plurality of the particles has the same cell label sequence.

The plurality of oligonucleotides on each particle can comprise different barcode sequences (e.g., molecular labels). In some embodiments, the number of barcode sequences can be, or be about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, or a number or a range between any two of these values. In some embodiments, the number of barcode sequences can be at least, or at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. For example, at least 100 of the plurality of oligonucleotides comprise different barcode sequences. As another example, in a single particle, at least 100, 500, 1000, 5000, 10000, 15000, 20000, 50000, a number or a range between any two of these values, or more of the plurality of oligonucleotides comprise different barcode sequences. Some embodiments provide a plurality of the particles comprising barcodes. In some embodiments, the ratio of an occurrence (or a copy or a number) of a target to be labeled and the different barcode sequences can be at least 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90, or more. In some embodiments, each of the plurality of oligonucleotides further comprises a sample label, a universal label, or both. The particle can be, for example, a nanoparticle or microparticle.

The size of a particle can vary. For example, the diameter of the particle can range from 0.1 micrometer to 50 micrometer. In some embodiments, the diameters of particles can be, or be about, 0.1, 0.5, 1, 2, 3, 4, 5, 6, 7, 8, 9, 10, 20, 30, 40, 50 micrometer, or a number or a range between any two of these values.

The diameter of the particle can be related to the diameter of the wells of the substrate. In some embodiments, the diameter of the particle can be, or be about, 10%, 20%, 30%, 40%, 50%, 60%, 70%, 80%, 90%, 100%, or a number or a range between any two of these values, longer or shorter than the diameter of the well. The diameter of the particle can be related to the diameter of a cell (e.g., a single cell entrapped by a well of the substrate). In some embodiments, the diameter of the particle can be at least, or at most, 10%, 20%, 30%, 40%, 50%, 60%, 70%, 80%, 90%, or 100% longer or shorter than the diameter of the well. The diameter of the particle can be related to the diameter of a cell (e.g., a single cell entrapped by a well of the substrate). In some embodiments, the diameter of the particle can be, or be about, 10%, 20%, 30%, 40%, 50%, 60%, 70%, 80%, 90%, 100%, 150%, 200%, 250%, 300%, or a number or a range between any two of these values, longer or shorter than the diameter of the cell. In some embodiments, the diameter of the particle can be at least, or at most, 10%, 20%, 30%, 40%, 50%, 60%, 70%, 80%, 90%, 100%, 150%, 200%, 250%, or 300% longer or shorter than the diameter of the cell.

A particle can be attached to and/or embedded in a substrate. A particle can be attached to and/or embedded in a gel, hydrogel, polymer and/or matrix. The spatial position of a particle within a substrate (e.g., gel, matrix, scaffold, or polymer) can be identified using the spatial label present on the barcode on the particle which can serve as a location address.

Examples of particles can include, but are not limited to, streptavidin beads, agarose beads, magnetic beads, Dynabeads®, MACS® microbeads, antibody conjugated beads (e.g., anti-immunoglobulin microbeads), protein A conjugated beads, protein G conjugated beads, protein A/G conjugated beads, protein L conjugated beads, oligo(dT) conjugated beads, silica beads, silica-like beads, anti-biotin microbeads, anti-fluorochrome microbeads, and BcMag™ Carboxyl-Terminated Magnetic Beads.

A particle can be associated with (e.g. impregnated with) quantum dots or fluorescent dyes to make it fluorescent in one fluorescence optical channel or multiple optical channels. A particle can be associated with iron oxide or chromium oxide to make it paramagnetic or ferromagnetic. Particles can be identifiable. For example, a particle can be imaged using a camera. A particle can have a detectable code associated with the particle. For example, a particle can comprise a barcode. A particle can change size, for example due to swelling in an organic or inorganic solution. A particle can be hydrophobic. A particle can be hydrophilic. A particle can be biocompatible.

A solid support (e.g., a particle) can be visualized. The solid support can comprise a visualizing tag (e.g., fluorescent dye). A solid support (e.g., a particle) can be etched with an identifier (e.g., a number). The identifier can be visualized through imaging the particles.

A solid support can comprise an insoluble, semi-soluble, or insoluble material. A solid support can be referred to as "functionalized" when it includes a linker, a scaffold, a building block, or other reactive moiety attached thereto, whereas a solid support may be "nonfunctionalized" when it lack such a reactive moiety attached thereto. The solid support can be employed free in solution, such as in a microtiter well format; in a flow-through format, such as in a column; or in a dipstick.

The solid support can comprise a membrane, paper, plastic, coated surface, flat surface, glass, slide, chip, or any combination thereof. A solid support can take the form of resins, gels, microspheres, or other geometric configurations. A solid support can comprise silica chips, microparticles, nanoparticles, plates, arrays, capillaries, flat supports such as glass fiber filters, glass surfaces, metal surfaces (steel, gold silver, aluminum, silicon and copper), glass supports, plastic supports, silicon supports, chips, filters, membranes, microwell plates, slides, plastic materials including multiwell plates or membranes (e.g., formed of polyethylene, polypropylene, polyamide, polyvinylidenedifluoride), and/or wafers, combs, pins or needles (e.g., arrays of pins suitable for combinatorial synthesis or analysis) or particles (e.g., synthetic particles such as beads) in an array of pits or nanoliter wells of flat surfaces such as wafers (e.g., silicon wafers), wafers with pits with or without filter bottoms.

The solid support can comprise a polymer matrix (e.g., gel, hydrogel). The polymer matrix may be able to permeate intracellular space (e.g., around organelles). The polymer matrix may able to be pumped throughout the circulatory system.

A solid support can be a biological molecule. For example a solid support can be, or can comprise, a nucleic acid, a protein, an antibody, a histone, a cellular compartment, a lipid, a carbohydrate, and the like. Solid supports that are biological molecules can be amplified, translated, transcribed, degraded, and/or modified (e.g., pegylated, sumoylated, acetylated, methylated). A solid support that is a biological molecule can provide spatial and time information in addition to the spatial label that is attached to the biological molecule. For example, a biological molecule can comprise a first confirmation when unmodified, but can change to a second confirmation when modified. The different conformations can expose barcodes (e.g., stochastic barcodes) of the disclosure to targets. For example, a biological molecule can comprise barcodes that are inaccessible due to folding of the biological molecule. Upon modification of the biological molecule (e.g., acetylation), the biological molecule can change conformation to expose the barcodes. The timing of the modification can provide another time dimension to the method of barcoding of the disclosure.

In some embodiments, the biological molecule comprising barcode reagents of the disclosure can be located in the cytoplasm of a cell. Upon activation, the biological molecule can move to the nucleus, whereupon barcoding can take place. In this way, modification of the biological molecule can encode additional space-time information for the targets identified by the barcodes.

Substrates and Microwell Array

As used herein, a substrate can refer to a type of solid support. A substrate can refer to a solid support that can comprise barcodes and stochastic barcodes of the disclosure. A substrate can, for example, comprise a plurality of microwells. For example, a substrate can be a well array comprising two or more microwells. In some embodiments, a microwell can comprise a small reaction chamber of defined volume. In some embodiments, a microwell can entrap one or more cells. In some embodiments, a microwell can entrap only one cell. In some embodiments, a microwell can entrap one or more solid supports. In some embodiments, a microwell can entrap only one solid support. In some embodiments, a microwell entraps a single cell and a single solid support (e.g., a particle). A microwell can comprise combinatorial barcode reagents of the disclosure.

Synthesis of Barcodes on Solid Supports

A barcode (e.g., a stochastic barcode) can be synthesized on a solid support (e.g., a particle, such as a synthetic particle or a bead). Pre-synthesized barcodes (e.g., comprising the 5'amine that can link to the solid support) can be attached to solid supports (e.g., particles) through any of a variety of immobilization techniques involving functional group pairs on the solid support and the barcode. The barcode can comprise a functional group. The solid support (e.g., a particle) can comprise a functional group. The barcode functional group and the solid support functional group can comprise, for example, biotin, streptavidin, primary amine(s), carboxyl(s), hydroxyl(s), aldehyde(s), ketone(s), and any combination thereof. A barcode (e.g., a stochastic barcode) can be tethered to a solid support, for example, by coupling (e.g. using 1-Ethyl-3-(3-dimethylaminopropyl) carbodiimide) a 5' amino group on the barcode to the carboxyl group of the functionalized solid support. Residual non-coupled barcodes can be removed from the reaction mixture by performing multiple rinse steps. In some embodiments, the barcode and solid support are attached indirectly via linker molecules (e.g. short, functionalized hydrocarbon molecules or polyethylene oxide molecules) using similar attachment chemistries. The linkers can be cleavable linkers, e.g. acid-labile linkers or photo-cleavable linkers.

The barcodes (e.g., stochastic barcodes) can be synthesized on solid supports (e.g., particles) using any of a number of solid-phase oligonucleotide synthesis techniques, such as phosphodiester synthesis, phosphotriester synthesis, phosphite triester synthesis, and phosphoramidite synthesis. Single nucleotides can be coupled in step-wise fashion to the growing, tethered barcode. A short, pre-synthesized sequence (or block) of several oligonucleotides can be coupled to the growing, tethered barcode.

Barcodes (e.g., stochastic barcodes) can be synthesized by interspersing step-wise or block coupling reactions with one or more rounds of split-pool synthesis, in which the total pool of synthesis particles is divided into a number of individual smaller pools which are then each subjected to a different coupling reaction, followed by recombination and mixing of the individual pools to randomize the growing barcode sequence across the total pool of particles. Split-pool synthesis is an example of a combinatorial synthesis process in which a maximum number of chemical compounds are synthesized using a minimum number of chemical coupling steps. The potential diversity of the compound library thus created is determined by the number of unique building blocks (e.g. nucleotides) available for each coupling step, and the number of coupling steps used to create the library. For example, a split-pool synthesis comprising 10 rounds of coupling using 4 different nucleotides at each step will yield $4^{10}=1,048,576$ unique nucleotide sequences. In some embodiments, split-pool synthesis can be performed using enzymatic methods such as polymerase extension or ligation reactions rather than chemical coupling. For example, in each round of a split-pool polymerase extension reaction, the 3' ends of the barcodes tethered to particles in a given pool can be hybridized with the 5'ends of a set of semi-random primers, e.g. primers having a structure of 5'-$(M)_k$-$(X)_i$-$(N)_j$-3', where $(X)_i$ is a random sequence of nucleotides that is i nucleotides long (the set of primers comprising all possible combinations of $(X)_i$), $(N)_j$ is a specific nucleotide (or series of j nucleotides), and $(M)_k$ is a specific nucleotide (or series of k nucleotides), wherein a different deoxyribonucleotide triphosphate (dNTP) is added to each pool and incorporated into the tethered oligonucleotides by the polymerase.

Methods of Barcoding

The disclosure provides for methods for estimating the number of distinct targets in a sample. In some embodiments, barcoding the plurality of targets comprises hybridizing a plurality of barcodes with a plurality of targets to create barcoded targets (e.g., stochastically barcoded targets). Barcoding the plurality of targets can comprise generating an indexed library of the barcoded targets. Generating an indexed library of the barcoded targets can be performed with a solid support comprising the plurality of barcodes (e.g., stochastic barcodes).

Contacting a Sample and a Barcode

The disclosure provides for methods for contacting a sample (e.g., cells) to a substrate of the disclosure. A sample comprising, for example, a cell, organ, or tissue thin section, can be contacted to barcodes (e.g., stochastic barcodes). The cells can be contacted, for example, by gravity flow wherein the cells can settle and create a monolayer. The sample can be a tissue thin section. The thin section can be placed on the substrate. The sample can be one-dimensional (e.g., forms a planar surface). The sample (e.g., cells) can be spread across the substrate, for example, by growing/culturing the cells on the substrate.

When barcodes are in close proximity to targets, the targets can hybridize to the barcode. The barcodes can be contacted at a non-depletable ratio such that each distinct target can associate with a distinct barcode of the disclosure. To ensure efficient association between the target and the barcode, the targets can be crosslinked to the barcode.

Cell Lysis

Following the distribution of cells and barcodes, the cells can be lysed to liberate the target molecules. Cell lysis can be accomplished by any of a variety of means, for example, by chemical or biochemical means, by osmotic shock, or by means of thermal lysis, mechanical lysis, or optical lysis. Cells can be lysed by addition of a cell lysis buffer comprising a detergent (e.g. SDS, Li dodecyl sulfate, Triton X-100, Tween-20, or NP-40), an organic solvent (e.g. methanol or acetone), or digestive enzymes (e.g. proteinase K, pepsin, or trypsin), or any combination thereof. To increase the association of a target and a barcode, the rate of the diffusion of the target molecules can be altered by for example, reducing the temperature and/or increasing the viscosity of the lysate.

In some embodiments, the sample can be lysed using a filter paper. The filter paper can be soaked with a lysis buffer on top of the filter paper. The filter paper can be applied to the sample with pressure which can facilitate lysis of the sample and hybridization of the targets of the sample to the substrate.

In some embodiments, lysis can be performed by mechanical lysis, heat lysis, optical lysis, and/or chemical lysis. Chemical lysis can include the use of digestive enzymes such as proteinase K, pepsin, and trypsin. Lysis can be performed by the addition of a lysis buffer to the substrate. A lysis buffer can comprise Tris HCl. A lysis buffer can comprise at least about, or at most about, 0.01, 0.05, 0.1, 0.5, or 1 M or more or less Tris HCl. A lysis buffer can comprise about 0.01, 0.05, 0.1, 0.5, or 1 M Tris HCl. The pH of the lysis buffer can be at least about 1, 2, 3, 4, 5, 6, 7, 8, 9, 10, or more. The pH of the lysis buffer can be at most about 1, 2, 3, 4, 5, 6, 7, 8, 9, 10, or more. In some embodiments, the pH of the lysis buffer is about 7.5. The lysis buffer can comprise a salt (e.g., LiCl). The concentration of salt in the lysis buffer can be at least about 0.1, 0.5, or 1 M or more. The concentration of salt in the lysis buffer can be at most about 0.1, 0.5, or 1 M or more. In some embodiments, the concentration of salt in the lysis buffer is about 0.5M. The lysis buffer can comprise a detergent (e.g., SDS, Li dodecyl sulfate, triton X, tween, NP-40). The concentration of the detergent in the lysis buffer can be at least about 0.0001%, 0.0005%, 0.001%, 0.005%, 0.01%, 0.05%, 0.1%, 0.5%, 1%, 2%, 3%, 4%, 5%, 6%, or 7%, or more. The concentration of the detergent in the lysis buffer can be at most about 0.0001%, 0.0005%, 0.001%, 0.005%, 0.01%, 0.05%, 0.1%, 0.5%, 1%, 2%, 3%, 4%, 5%, 6%, or 7% or more. In some embodiments, the concentration of the detergent in the lysis buffer is about 1% Li dodecyl sulfate. The time used in the method for lysis can be dependent on the amount of detergent used. In some embodiments, the more detergent used, the less time needed for lysis. The lysis buffer can comprise a chelating agent (e.g., EDTA, EGTA). The concentration of a chelating agent in the lysis buffer can be at least about 1, 5, 10, 15, 20, 25, or 30 mM, or more. The concentration of a chelating agent in the lysis buffer can be at most about 1, 5, 10, 15, 20, 25, or 30 mM or more. In some embodiments, the concentration of chelating agent in the lysis buffer is about 10 mM. The lysis buffer can comprise a reducing reagent (e.g., beta-mercaptoethanol, DTT). The concentration of the reducing reagent in the lysis buffer can be at least about 1, 5, 10, 15, or 20 mM or more. The concentration of the reducing reagent in the lysis buffer can be at most about 1, 5, 10, 15, or 20 mM or more. In some embodiments, the concentration of reducing reagent in the lysis buffer is about 5 mM. In some embodiments, a lysis buffer can comprise about 0.1M TrisHCl, about pH 7.5, about 0.5M LiCl, about 1% lithium dodecyl sulfate, about 10 mM EDTA, and about 5 mM DTT.

Lysis can be performed at a temperature of about 4, 10, 15, 20, 25, or 30° C. Lysis can be performed for about 1, 5, 10, 15, 20, or more minutes. A lysed cell can comprise at least about 100000, 200000, 300000, 400000, 500000, 600000, 700000, or more target nucleic acid molecules. A lysed cell can comprise at most about 100000, 200000, 300000, 400000, 500000, 600000, 700000, or more target nucleic acid molecules.

Attachment of Barcodes to Target Nucleic Acid Molecules

Following lysis of the cells and release of nucleic acid molecules therefrom, the nucleic acid molecules can randomly associate with the barcodes of the co-localized solid support. Association can comprise hybridization of a barcode's target recognition region to a complementary portion of the target nucleic acid molecule (e.g., oligo(dT) of the barcode can interact with a poly(A) tail of a target). The assay conditions used for hybridization (e.g. buffer pH, ionic strength, temperature, etc.) can be chosen to promote formation of specific, stable hybrids. In some embodiments, the nucleic acid molecules released from the lysed cells can associate with the plurality of probes on the substrate (e.g., hybridize with the probes on the substrate). When the probes comprise oligo(dT), mRNA molecules can hybridize to the probes and be reverse transcribed. The oligo(dT) portion of the oligonucleotide can act as a primer for first strand synthesis of the cDNA molecule. For example, in a non-limiting example of barcoding illustrated in FIG. 2, at block 216, mRNA molecules can hybridize to barcodes on particles. For example, single-stranded nucleotide fragments can hybridize to the target-binding regions of barcodes.

Attachment can further comprise ligation of a barcode's target recognition region and a portion of the target nucleic acid molecule. For example, the target-binding region can comprise a nucleic acid sequence that can be capable of specific hybridization to a restriction site overhang (e.g. an EcoRI sticky-end overhang). The assay procedure can further comprise treating the target nucleic acids with a restriction enzyme (e.g. EcoRI) to create a restriction site overhang. The barcode can then be ligated to any nucleic acid molecule comprising a sequence complementary to the restriction site overhang. A ligase (e.g., T4 DNA ligase) can be used to join the two fragments.

For example, in a non-limiting example of barcoding illustrated in FIG. 2, at block 220, the labeled targets from a plurality of cells (or a plurality of samples) (e.g., target-barcode molecules) can be subsequently pooled, for example, into a tube. The labeled targets can be pooled by, for example, retrieving the barcodes and/or the particles to which the target-barcode molecules are attached.

The retrieval of solid support-based collections of attached target-barcode molecules can be implemented by use of magnetic particles and an externally-applied magnetic field. Once the target-barcode molecules have been pooled, all further processing can proceed in a single reaction vessel. Further processing can include, for example, reverse transcription reactions, amplification reactions, cleavage reactions, dissociation reactions, and/or nucleic acid extension reactions. Further processing reactions can be performed within the microwells, that is, without first pooling the labeled target nucleic acid molecules from a plurality of cells.

Reverse Transcription

The disclosure provides for a method to create a target-barcode conjugate using reverse transcription (e.g., at block 224 of FIG. 2). The target-barcode conjugate can comprise the barcode and a complementary sequence of all or a portion of the target nucleic acid (i.e. a barcoded cDNA molecule, such as a stochastically barcoded cDNA molecule). Reverse transcription of the associated RNA molecule can occur by the addition of a reverse transcription primer along with the reverse transcriptase. The reverse transcription primer can be an oligo(dT) primer, a random hexanucleotide primer, or a target-specific oligonucleotide primer. Oligo(dT) primers can be, or can be about, 12-18 nucleotides in length and bind to the endogenous poly(A) tail at the 3' end of mammalian mRNA. Random hexanucleotide primers can bind to mRNA at a variety of complementary sites. Target-specific oligonucleotide primers typically selectively prime the mRNA of interest.

In some embodiments, reverse transcription of the labeled-RNA molecule can occur by the addition of a reverse transcription primer. In some embodiments, the reverse transcription primer is an oligo(dT) primer, random hexanucleotide primer, or a target-specific oligonucleotide primer. Generally, oligo(dT) primers are 12-18 nucleotides in length and bind to the endogenous poly(A)+ tail at the 3' end of mammalian mRNA. Random hexanucleotide primers can bind to mRNA at a variety of complementary sites. Target-specific oligonucleotide primers typically selectively prime the mRNA of interest.

Reverse transcription can occur repeatedly to produce multiple labeled-cDNA molecules. The methods disclosed herein can comprise conducting at least about 1, 2, 3, 4, 5, 6, 7, 8, 9, 10, 11, 12, 13, 14, 15, 16, 17, 18, 19, or 20 reverse transcription reactions. The method can comprise conducting at least about 25, 30, 35, 40, 45, 50, 55, 60, 65, 70, 75, 80, 85, 90, 95, or 100 reverse transcription reactions.

Amplification

One or more nucleic acid amplification reactions (e.g., at block 228 of FIG. 2) can be performed to create multiple copies of the labeled target nucleic acid molecules. Amplification can be performed in a multiplexed manner, wherein multiple target nucleic acid sequences are amplified simultaneously. The amplification reaction can be used to add sequencing adaptors to the nucleic acid molecules. The amplification reactions can comprise amplifying at least a portion of a sample label, if present. The amplification reactions can comprise amplifying at least a portion of the cell label and/or barcode sequence (e.g., molecular label). The amplification reactions can comprise amplifying at least a portion of a sample tag, a cell label, a spatial label, a barcode (e.g., a molecular label), a target nucleic acid, or a combination thereof. The amplification reactions can comprise amplifying 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 100%, or a range or a number between any two of these values, of the plurality of nucleic acids. The method can further comprise conducting one or more cDNA synthesis reactions to produce one or more cDNA copies of target-barcode molecules comprising a sample label, a cell label, a spatial label, and/or a barcode sequence (e.g., a molecular label).

In some embodiments, amplification can be performed using a polymerase chain reaction (PCR). As used herein, PCR can refer to a reaction for the in vitro amplification of specific DNA sequences by the simultaneous primer extension of complementary strands of DNA. As used herein, PCR can encompass derivative forms of the reaction, including but not limited to, RT-PCR, real-time PCR, nested PCR, quantitative PCR, multiplexed PCR, digital PCR, and assembly PCR.

Amplification of the labeled nucleic acids can comprise non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), and a Qβ replicase (Qβ) method, use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and ramification extension amplification (RAM). In some embodiments, the amplification does not produce circularized transcripts.

In some embodiments, the methods disclosed herein further comprise conducting a polymerase chain reaction on the labeled nucleic acid (e.g., labeled-RNA, labeled-DNA, labeled-cDNA) to produce a labeled-amplicon (e.g., a stochastically labeled-amplicon). The labeled-amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample label, a spatial label, a cell label, and/or a barcode sequence (e.g., a molecular label). The labeled-amplicon can be a single-stranded molecule. The single-stranded molecule can comprise DNA, RNA, or a combination thereof. The nucleic acids of the disclosure can comprise synthetic or altered nucleic acids.

Amplification can comprise use of one or more non-natural nucleotides. Non-natural nucleotides can comprise photolabile or triggerable nucleotides. Examples of non-natural nucleotides can include, but are not limited to, peptide nucleic acid (PNA), morpholino and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise, for example, 1, 2, 3, 4, 5, 6, 7, 8, 9, 10, 11, 12, 13, 14, or 15 or more nucleotides. The one or more primers can comprise at least 1, 2, 3, 4, 5, 6, 7, 8, 9, 10, 11, 12, 13, 14, or 15 or more nucleotides. The one or more primers can comprise less than 12-15 nucleotides. The one or more primers can anneal to at least a portion of the plurality of labeled targets (e.g., stochastically labeled targets). The one or more primers can anneal to the 3' end or 5' end of the plurality of labeled targets. The one or more primers can anneal to an internal region of the plurality of labeled targets. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled targets. The one or more primers can comprise a fixed panel of primers. The one or more primers can comprise at least one or more custom primers. The one or more primers can comprise at least one or more control primers. The one or more primers can comprise at least one or more gene-specific primers.

The one or more primers can comprise a universal primer. The universal primer can anneal to a universal primer binding site. The one or more custom primers can anneal to a first sample label, a second sample label, a spatial label, a cell label, a barcode sequence (e.g., a molecular label), a target, or any combination thereof. The one or more primers can comprise a universal primer and a custom primer. The custom primer can be designed to amplify one or more targets. The targets can comprise a subset of the total nucleic acids in one or more samples. The targets can comprise a subset of the total labeled targets in one or more samples. The one or more primers can comprise at least 96 or more custom primers. The one or more primers can comprise at least 960 or more custom primers. The one or more primers can comprise at least 9600 or more custom primers. The one or more custom primers can anneal to two or more different labeled nucleic acids. The two or more different labeled nucleic acids can correspond to one or more genes.

Any amplification scheme can be used in the methods of the present disclosure. For example, in one scheme, the first round PCR can amplify molecules attached to the particle (e.g., a bead) using a gene specific primer and a primer against the universal Illumina sequencing primer 1 sequence. The second round of PCR can amplify the first PCR products using a nested gene specific primer flanked by Illumina sequencing primer 2 sequence, and a primer against the universal Illumina sequencing primer 1 sequence. The third round of PCR adds P5 and P7 and sample index to turn PCR products into an Illumina sequencing library. Sequencing using 150 bp×2 sequencing can reveal the cell label and barcode sequence (e.g., molecular label) on read 1, the gene on read 2, and the sample index on index 1 read.

In some embodiments, nucleic acids can be removed from the substrate using chemical cleavage. For example, a chemical group or a modified base present in a nucleic acid can be used to facilitate its removal from a solid support. For example, an enzyme can be used to remove a nucleic acid from a substrate. For example, a nucleic acid can be removed from a substrate through a restriction endonuclease digestion. For example, treatment of a nucleic acid containing a dUTP or ddUTP with uracil-d-glycosylase (UDG) can be used to remove a nucleic acid from a substrate. For example, a nucleic acid can be removed from a substrate using an enzyme that performs nucleotide excision, such as a base excision repair enzyme, such as an apurinic/apyrimidinic (AP) endonuclease. In some embodiments, a nucleic acid can be removed from a substrate using a photocleavable group and light. In some embodiments, a cleavable linker can be used to remove a nucleic acid from the substrate. For example, the cleavable linker can comprise at least one of biotin/avidin, biotin/streptavidin, biotin/neutravidin, Ig-protein A, a photo-labile linker, acid or base labile linker group, or an aptamer.

When the probes are gene-specific, the molecules can hybridize to the probes and be reverse transcribed and/or amplified. In some embodiments, after the nucleic acid has been synthesized (e.g., reverse transcribed), it can be amplified. Amplification can be performed in a multiplex manner, wherein multiple target nucleic acid sequences are amplified simultaneously. Amplification can add sequencing adaptors to the nucleic acid.

In some embodiments, amplification can be performed on the substrate, for example, with bridge amplification. cDNAs can be homopolymer tailed in order to generate a compatible end for bridge amplification using oligo(dT) probes on the substrate. In bridge amplification, the primer that is complementary to the 3' end of the template nucleic acid can be the first primer of each pair that is covalently attached to the solid particle. When a sample containing the template nucleic acid is contacted with the particle and a single thermal cycle is performed, the template molecule can be annealed to the first primer and the first primer is elongated in the forward direction by addition of nucleotides to form a duplex molecule consisting of the template molecule and a newly formed DNA strand that is complementary to the template. In the heating step of the next cycle, the duplex molecule can be denatured, releasing the template molecule from the particle and leaving the complementary DNA strand attached to the particle through the first primer. In the annealing stage of the annealing and elongation step that follows, the complementary strand can hybridize to the second primer, which is complementary to a segment of the complementary strand at a location removed from the first primer. This hybridization can cause the complementary strand to form a bridge between the first and second primers secured to the first primer by a covalent bond and to the second primer by hybridization. In the elongation stage, the second primer can be elongated in the reverse direction by the addition of nucleotides in the same reaction mixture, thereby converting the bridge to a double-stranded bridge. The next cycle then begins, and the double-stranded bridge can be denatured to yield two single-stranded nucleic acid molecules, each having one end attached to the particle surface via the first and second primers, respectively, with the other end of each unattached. In the annealing and elongation step of this second cycle, each strand can hybridize to a further complementary primer, previously unused, on the same particle, to form new single-strand bridges. The two previously unused primers that are now hybridized elongate to convert the two new bridges to double-strand bridges.

The amplification reactions can comprise amplifying at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the plurality of nucleic acids.

Amplification of the labeled nucleic acids can comprise PCR-based methods or non-PCR based methods. Amplification of the labeled nucleic acids can comprise exponential amplification of the labeled nucleic acids. Amplification of the labeled nucleic acids can comprise linear amplification of the labeled nucleic acids. Amplification can be performed by polymerase chain reaction (PCR). PCR can refer to a reaction for the in vitro amplification of specific DNA sequences by the simultaneous primer extension of complementary strands of DNA. PCR can encompass derivative forms of the reaction, including but not limited to, RT-PCR, real-time PCR, nested PCR, quantitative PCR, multiplexed PCR, digital PCR, suppression PCR, semi-suppressive PCR and assembly PCR.

In some embodiments, amplification of the labeled nucleic acids comprises non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), a Qβ replicase (Qβ), use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and/or ramification extension amplification (RAM).

In some embodiments, the methods disclosed herein further comprise conducting a nested polymerase chain reaction on the amplified amplicon (e.g., target). The amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample tag or molecular identifier label. Alternatively, the amplicon can be a single-stranded molecule. The single-stranded molecule can comprise DNA, RNA, or a combination thereof. The nucleic acids of the present invention can comprise synthetic or altered nucleic acids.

In some embodiments, the method comprises repeatedly amplifying the labeled nucleic acid to produce multiple amplicons. The methods disclosed herein can comprise conducting at least about 1, 2, 3, 4, 5, 6, 7, 8, 9, 10, 11, 12, 13, 14, 15, 16, 17, 18, 19, or 20 amplification reactions. Alternatively, the method comprises conducting at least about 25, 30, 35, 40, 45, 50, 55, 60, 65, 70, 75, 80, 85, 90, 95, or 100 amplification reactions.

Amplification can further comprise adding one or more control nucleic acids to one or more samples comprising a plurality of nucleic acids. Amplification can further comprise adding one or more control nucleic acids to a plurality of nucleic acids. The control nucleic acids can comprise a control label.

Amplification can comprise use of one or more non-natural nucleotides. Non-natural nucleotides can comprise photolabile and/or triggerable nucleotides. Examples of non-natural nucleotides include, but are not limited to, peptide nucleic acid (PNA), morpholino and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise one or more oligonucleotides. The one or more oligonucleotides can comprise at least about 7-9 nucleotides. The one or more oligonucleotides can comprise less than 12-15 nucleotides. The one or more primers can anneal to at least a portion of the plurality of labeled nucleic acids. The one or more primers can anneal to the 3' end and/or 5' end of the plurality of labeled nucleic acids. The one or more primers can anneal to an internal region of the plurality of labeled nucleic acids. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900, or 1000 nucleotides from the 3' ends the plurality of labeled nucleic acids. The one or more primers can comprise a fixed panel of primers. The one or more primers can comprise at least one or more custom primers. The one or more primers can comprise at least one or more control primers. The one or more primers can comprise at least one or more housekeeping gene primers. The one or more primers can comprise a universal primer. The universal primer can anneal to a universal primer binding site. The one or more custom primers can anneal to the first sample tag, the second sample tag, the molecular identifier label, the nucleic acid or a product thereof. The one or more primers can comprise a universal primer and a custom primer. The custom primer can be designed to amplify one or more target nucleic acids. The target nucleic acids can comprise a subset of the total nucleic acids in one or more samples. In some embodiments, the primers are the probes attached to the array of the disclosure.

In some embodiments, barcoding (e.g., stochastically barcoding) the plurality of targets in the sample further comprises generating an indexed library of the barcoded fragments. The barcodes sequences of different barcodes (e.g., the molecular labels of different stochastic barcodes) can be different from one another. Generating an indexed library of the barcoded targets (e.g., stochastically barcoded targets) includes generating a plurality of indexed polynucleotides from the plurality of targets in the sample. For example, for an indexed library of the barcoded targets comprising a first indexed target and a second indexed target, the label region of the first indexed polynucleotide can differ from the label region of the second indexed polynucleotide by, by about, by at least, or by at most, 1, 2, 3, 4, 5, 6, 7, 8, 9, 10, 20, 30, 40, 50, or a number or a range between any two of these values, nucleotides. In some embodiments, generating an indexed library of the barcoded targets includes contacting a plurality of targets, for example mRNA molecules, with a plurality of oligonucleotides including a poly(T) region and a label region; and conducting a first strand synthesis using a reverse transcriptase to produce single-strand labeled cDNA molecules each comprising a cDNA region and a label region, wherein the plurality of targets includes at least two mRNA molecules of different sequences and the plurality of oligonucleotides includes at least two oligonucleotides of different sequences. Generating an indexed library of the barcoded targets can further comprise amplifying the single-strand labeled cDNA molecules to produce double-strand labeled cDNA molecules; and conducting nested PCR on the double-strand labeled cDNA molecules to produce labeled amplicons. In some embodiments, the method can include generating an adaptor-labeled amplicon.

Stochastic barcoding can use nucleic acid barcodes or tags to label individual nucleic acid (e.g., DNA or RNA) molecules. In some embodiments, it involves adding DNA barcodes or tags to cDNA molecules as they are generated from mRNA. Nested PCR can be performed to minimize PCR amplification bias. Adaptors can be added for sequencing using, for example, next generation sequencing (NGS). The sequencing results can be used to determine cell labels, barcode sequences (e.g., molecular labels), and sequences of nucleotide fragments of the one or more copies of the targets, for example at block 232 of FIG. 2.

Figure 3:
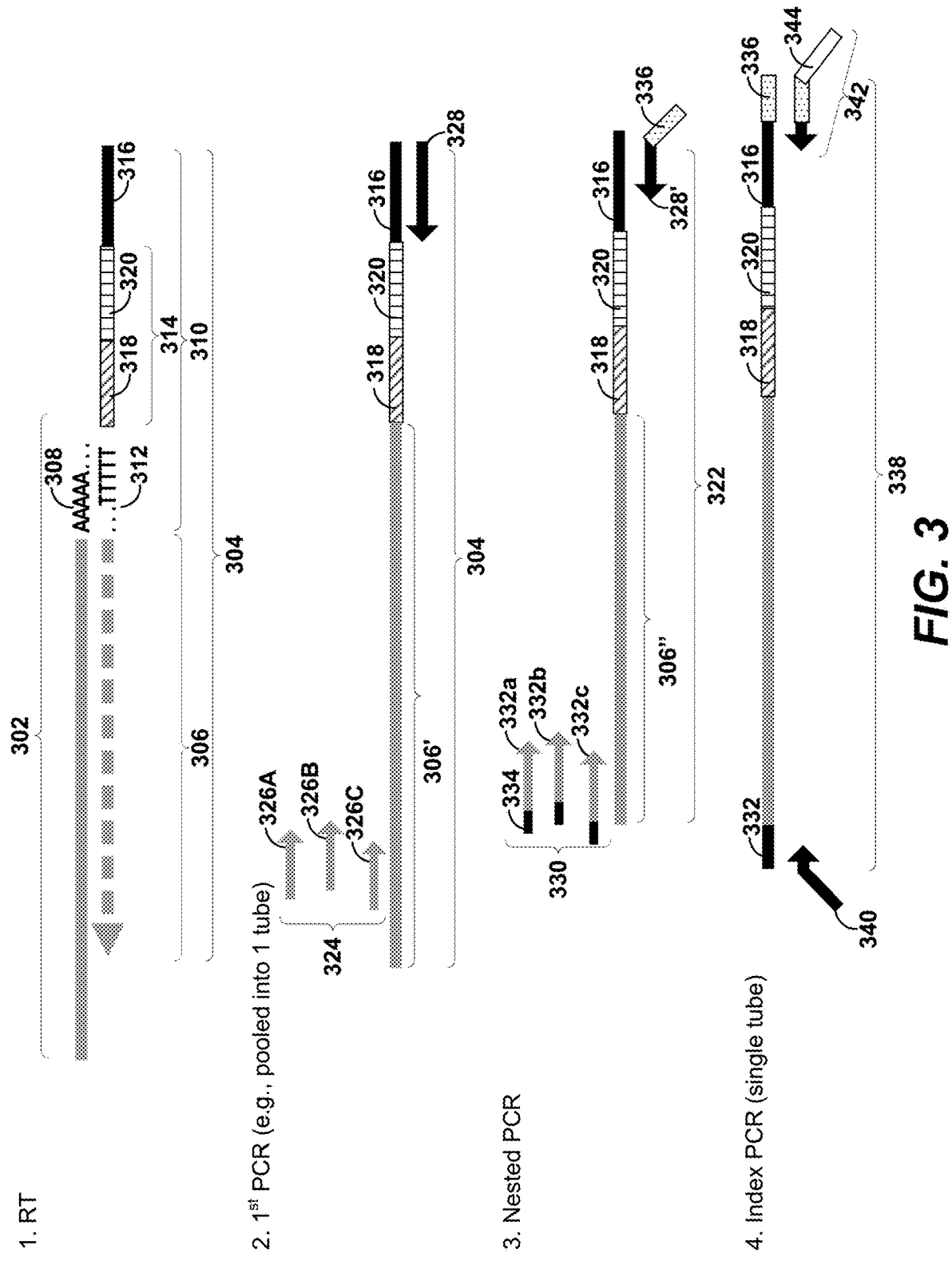
FIG. 3 is a schematic illustration showing a non-limiting exemplary process for generating an indexed library of the barcoded targets (e.g., stochastically barcoded targets) from a plurality of targets.

FIG. 3 is a schematic illustration showing a non-limiting exemplary process of generating an indexed library of the barcoded targets (e.g., stochastically barcoded targets), for example mRNAs. As shown in step 1, the reverse transcription process can encode each mRNA molecule with a unique barcode sequence (e.g., molecular label), a cell label, and a universal PCR site. For example, RNA molecules 302 can be reverse transcribed to produce labeled cDNA molecules 304, including a cDNA region 306, by the hybridization (e.g., stochastic hybridization) of a set of barcodes (e.g., stochastic barcodes) 310) to the poly(A) tail region 308 of the RNA molecules 302. Each of the barcodes 310 can comprise a target-binding region, for example a poly(dT) region 312, a barcode sequence or a molecular label 314, and a universal PCR region 316.

In some embodiments, the cell label can include 3 to 20 nucleotides. In some embodiments, the barcode sequence (e.g., molecular label) can include 3 to 20 nucleotides. In some embodiments, each of the plurality of stochastic barcodes further comprises one or more of a universal label and a cell label, wherein universal labels are the same for the plurality of stochastic barcodes on the solid support and cell labels are the same for the plurality of stochastic barcodes on the solid support. In some embodiments, the universal label can include 3 to 20 nucleotides. In some embodiments, the cell label comprises 3 to 20 nucleotides.

In some embodiments, the label region 314 can include a barcode sequence or a molecular label 318 and a cell label 320. In some embodiments, the label region 314 can include one or more of a universal label, a dimension label, and a cell label. The barcode sequence or molecular label 318 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The cell label 320 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The universal label can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. Universal labels can be the same for the plurality of stochastic barcodes on the solid support and cell labels are the same for the plurality of stochastic barcodes on the solid support. The dimension label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length.

In some embodiments, the label region 314 can comprise, comprise about, comprise at least, or comprise at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different labels, such as a barcode sequence or a molecular label 318 and a cell label 320. Each label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length. A set of barcodes or stochastic barcodes 310 can contain, contain about, contain at least, or can be at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, barcodes or stochastic barcodes 310. And the set of barcodes or stochastic barcodes 310 can, for example, each contain a unique label region 314. The labeled cDNA molecules 304 can be purified to remove excess barcodes or stochastic barcodes 310. Purification can comprise Ampure bead purification.

As shown in step 2, products from the reverse transcription process in step 1 can be pooled into 1 tube and PCR amplified with a $1^{st}$ PCR primer pool and a $1^{st}$ universal PCR primer. Pooling is possible because of the unique label region 314. In particular, the labeled cDNA molecules 304 can be amplified to produce nested PCR labeled amplicons 322. Amplification can comprise multiplex PCR amplification. Amplification can comprise a multiplex PCR amplification with 96 multiplex primers in a single reaction volume. In some embodiments, multiplex PCR amplification can utilize, utilize about, utilize at least, or utilize at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, multiplex primers in a single reaction volume. Amplification can comprise $1^{st}$ PCR primer pool 324 of custom primers 326A-C targeting specific genes and a universal primer 328. The custom primers 326 can hybridize to a region within the cDNA portion 306' of the labeled cDNA molecule 304. The universal primer 328 can hybridize to the universal PCR region 316 of the labeled cDNA molecule 304.

As shown in step 3 of FIG. 3, products from PCR amplification in step 2 can be amplified with a nested PCR primers pool and a $2^{nd}$ universal PCR primer. Nested PCR can minimize PCR amplification bias. For example, the nested PCR labeled amplicons 322 can be further amplified by nested PCR. The nested PCR can comprise multiplex PCR with nested PCR primers pool 330 of nested PCR primers 332a-c and a $2^{nd}$ universal PCR primer 328' in a single reaction volume. The nested PCR primer pool 328 can contain, contain about, contain at least, or contain at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different nested PCR primers 330. The nested PCR primers 332 can contain an adaptor 334 and hybridize to a region within the cDNA portion 306'' of the labeled amplicon 322. The universal primer 328' can contain an adaptor 336 and hybridize to the universal PCR region 316 of the labeled amplicon 322. Thus, step 3 produces adaptor-labeled amplicon 338. In some embodiments, nested PCR primers 332 and the $2^{nd}$ universal PCR primer 328' may not contain the adaptors 334 and 336. The adaptors 334 and 336 can instead be ligated to the products of nested PCR to produce adaptor-labeled amplicon 338.

As shown in step 4, PCR products from step 3 can be PCR amplified for sequencing using library amplification primers. In particular, the adaptors 334 and 336 can be used to conduct one or more additional assays on the adaptor-labeled amplicon 338. The adaptors 334 and 336 can be hybridized to primers 340 and 342. The one or more primers 340 and 342 can be PCR amplification primers. The one or more primers 340 and 342 can be sequencing primers. The one or more adaptors 334 and 336 can be used for further amplification of the adaptor-labeled amplicons 338. The one or more adaptors 334 and 336 can be used for sequencing the adaptor-labeled amplicon 338. The primer 342 can contain a plate index 344 so that amplicons generated using the same set of barcodes or stochastic barcodes 310 can be sequenced in one sequencing reaction using next generation sequencing (NGS).

Synthetic Particles with Spacer Oligonucleotides

Disclosed herein include particles (e.g., synthetic particles), where the particle comprises: a plurality of oligonucleotide barcodes (e.g., capture oligonucleotide barcodes), wherein each of the plurality of oligonucleotide barcodes comprises an identical cellular label, a molecular label, and a target-binding region, and wherein at least 10 of the plurality of oligonucleotide barcodes comprise different molecular label sequences, and a first plurality of spacer oligonucleotides (or oligonucleotides with target-specific target-binding regions), wherein each of the first plurality of spacer oligonucleotides does not comprise the target-binding region (i.e., the nucleic acid sequence of the target-binding region) present in the oligonucleotide barcodes (e.g., capture oligonucleotide barcodes). For example, the spacer oligonucleotide does not comprise a nucleic acid sequence having more than 95%, 90%, 85%, 80%, 75%, 70%, 65%, 60%, 55%, 50%, 45%, 40%, 35%, 30%, or 25% sequence identity to the target-binding region present in the oligonucleotide barcodes (e.g., capture oligonucleotide barcodes). In some embodiments, the spacer oligonucleotide comprises a nucleic acid sequence having no more than 95%, 90%, 85%, 80%, 75%, 70%, 65%, 60%, 55%, 50%, 45%, 40%, 35%, 30%, or 25% sequence identity to the target-binding region present in the oligonucleotide barcodes (e.g., capture oligonucleotide barcodes). In some embodiments, the spacer oligonucleotide does not comprise a region longer than, for example, 10-30 nucleotides long that has more than 95%, 90%, 85%, 80%, 75%, 70%, 65%, 60%, 55%, 50%, 45%, 40%, 35%, 30%, or 25% sequence identity to the target-binding region present in the oligonucleotide barcodes (e.g., capture oligonucleotide barcodes). In some embodiments, the spacer oligonucleotide does not hybridize to the sequence to which the target-binding region specifically hybridizes to under a desired nucleic acid hybridization condition. In some embodiments, the spacer oligonucleotide does not specifically bind to the sequence to which the target-binding region specifically hybridizes to under a desired nucleic acid hybridization condition.

Density of Oligonucleotide Barcodes

Figure 4A:
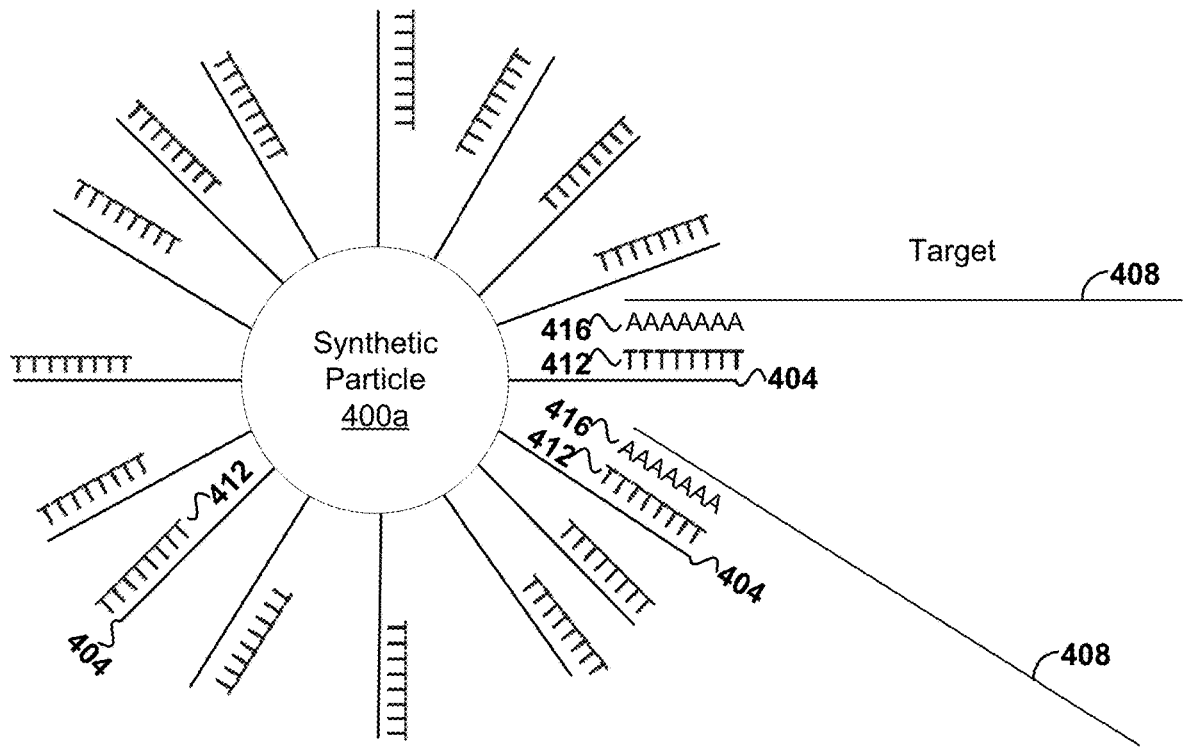
FIG. 4A is a non-limiting exemplary synthetic particle associated with a plurality of oligonucleotide barcodes.

As described herein, the density of oligonucleotide barcodes (e.g., stochastic barcodes) on a particle (e.g., a synthetic particle) for barcoding (e.g., stochastic barcoding) can affect the efficiency of target capturing targets (e.g., the efficiency of capturing mRNA targets). FIG. 4A is a non-limiting exemplary synthetic particle associated with a plurality of oligonucleotide barcodes. For example, a synthetic particle 400a can be associated with (e.g., coupled to or conjugated with) oligonucleotide barcodes 404 (16 oligonucleotide barcodes 404 are illustrated). Oligonucleotide barcodes 404 are also referred to herein as capture oligonucleotides. If the density of oligonucleotide barcodes 404 on a synthetic particle 400a is high, the efficiency of target 408 capturing can be lower than if the density of oligonucleotide barcodes on the synthetic particle is lower (See FIGS. 4B and 4C for examples). Without being bound by any particular theory, if the density of oligonucleotide barcodes 404 on a synthetic particle 400a is too high, there may be too much steric hindrance amongst the oligonucleotide barcodes 404 such that the synthetic particles 400a captures fewer target molecules 408 than if the density was lower. For example, if the density of the target-binding regions 412 (poly(dT) tails illustrated) of the oligonucleotide barcodes 404 is too high, there may be steric hindrance amongst the oligonucleotide barcodes 404 (or steric hindrance amongst the target-binding regions such that the some target molecules 408 (poly(A) tails 416 of the target molecules 408 illustrated) do not hybridize to the oligonucleotide barcodes 404. Therefore, it can be advantageous in some embodiments to reduce the density of capture oligonucleotide barcodes in the particle, for example, by associating spacer oligonucleotides with the particle. As described herein, the form, type, length, density, and location of the spacer oligonucleotides can vary. The number of the spacer oligonucleotides associated with the particle can be greater than, smaller than, equal to, or substantially equal to, the number of the capture oligonucleotide associate with the same particle. Although the synthetic particle 400a is illustrated to be associated with 16 oligonucleotide barcodes 404, the number of oligonucleotide barcodes 404 is for illustration only and is not intended to be limiting.

Figure 4B:
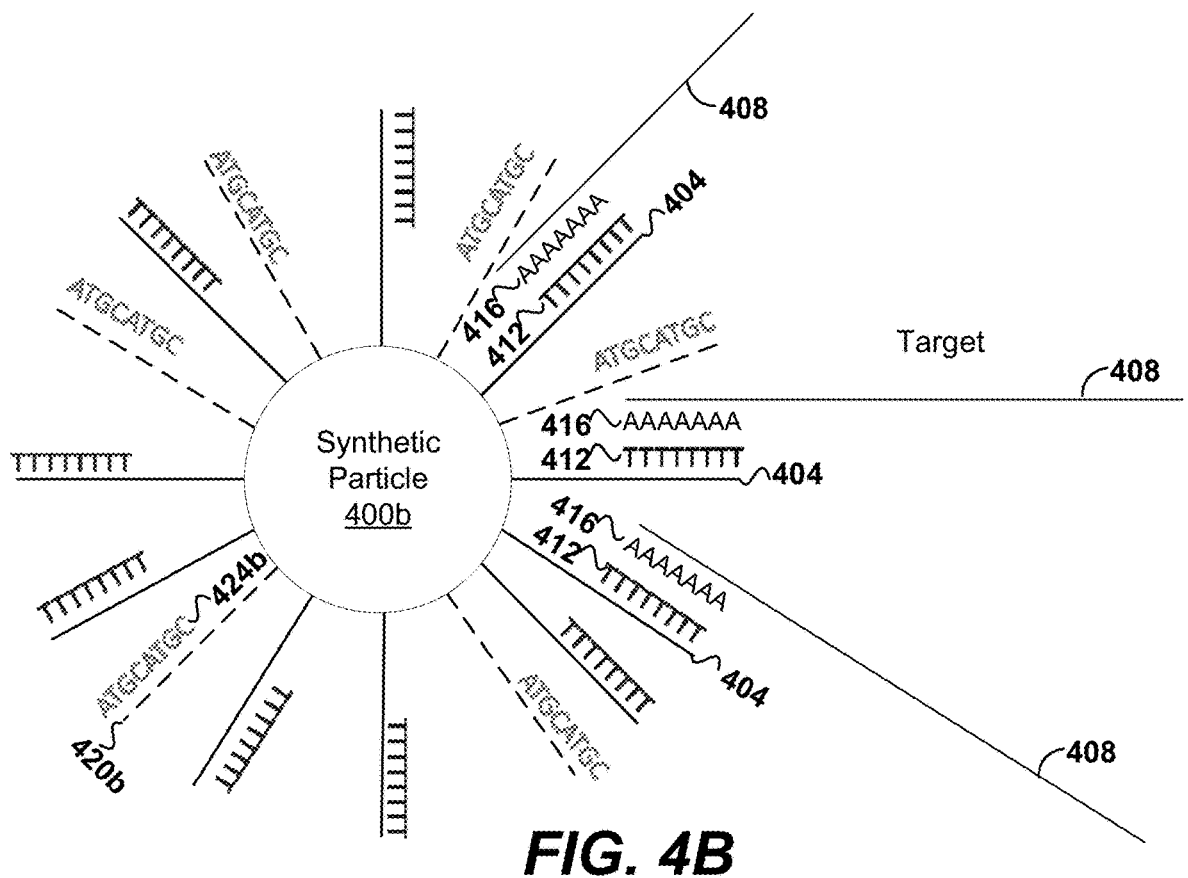
FIG. 4B is a non-limiting exemplary synthetic particle associated with a plurality of oligonucleotide barcodes and a plurality of spacer oligonucleotides.

FIG. 4B is a non-limiting exemplary synthetic particle associated with a plurality of oligonucleotide barcodes and a plurality of spacer oligonucleotides. As illustrated, a synthetic particle 400b can include spacer oligonucleotides 420b (six spacer oligonucleotides 420b illustrated) and oligonucleotide barcodes 404. The oligonucleotide barcodes 404 can include target-binding regions 412 capable of capturing (e.g., hybridizing) targets molecules 408. The spacer oligonucleotides 420b can include spacer regions 424b, corresponding to the target-binding regions 412, not capable of capturing (e.g., hybridizing to) target molecules 408. Including spacer oligonucleotides 420b on a synthetic particle 400b can improve target 408 capture (e.g., mRNA capture) and subsequent quantification of target molecules 408 captured. For example, a synthetic particle 400b can be coupled with both oligonucleotide barcodes 404 (e.g., barcodes each with a poly(dT) region that can bind to a copy or an occurrence of a mRNA molecule or species via the poly(dA) tail 416) and spacer oligonucleotides 420b, which can improve mRNA capture and gene expression quantification. Although the synthetic particle 400b is illustrated to be associated with 10 oligonucleotide barcodes 404 and six spacer oligonucleotides 420b, the numbers of oligonucleotide barcodes 404 and spacer oligonucleotides are for illustration only and are not intended to be limiting.

The spacer oligonucleotides associated with a synthetic particle can be shorter or longer than the oligonucleotide barcodes. For example, all spacer oligonucleotides associated with a synthetic particle can be shorter than the oligonucleotide barcodes (See FIG. 4C1 for an example). As another example, all spacer oligonucleotides associated with a synthetic particle can be longer than the oligonucleotide barcodes (See FIG. 4C2 for an example). For example, some spacer oligonucleotides associated with a synthetic particle can be longer than the oligonucleotide barcodes, and some spacer oligonucleotides associated with a synthetic particle can be shorter than the oligonucleotide barcodes.

FIG. 4C1 is a non-limiting exemplary synthetic particle associated with a plurality of oligonucleotide barcodes and a plurality of spacer oligonucleotides each being shorter than the oligonucleotide barcode. The spacer oligonucleotides 420c1 on a synthetic particle 400c1 can be shorter than the oligonucleotide barcodes 404. A synthetic particle 400c1 associated with oligonucleotide barcodes 404 with the same sequence (or target-binding regions 412 with the same sequence) can be first generated. An enzyme, such as an exonuclease (5' or 3') or an endonuclease, can be used to remove the target-binding regions 412 of some of the oligonucleotide barcodes 404. The resulting shorter oligonucleotide barcodes on the synthetic particle are referred to herein as spacer oligonucleotides 420c.

In some embodiments, the density of the oligonucleotide barcodes 404 can be lowered by associating (e.g., coupling) both oligonucleotide barcodes 404 and spacer oligonucleotides 420c1 illustrated in FIG. 4C1 to a synthetic particle 400c1, and then subsequently lowered using an exonuclease or an endonuclease.

FIG. 4C2 is a non-limiting exemplary synthetic particle associated with a plurality of oligonucleotide barcodes and a plurality of spacer oligonucleotides each being longer than the oligonucleotide barcode. The spacer oligonucleotides 420c2 on a synthetic particle 400c2 can be longer than the oligonucleotide barcodes 404. For example, a synthetic particle 400c2 associated with oligonucleotide barcodes 404 with the same sequence (or target-binding regions 412 with the same sequence) can be first generated. An enzyme, such as a polymerase or a ligase, can be used to add one or more sequences, by extension or ligation, to some of the oligonucleotide barcodes 404 to generate spacer oligonucleotides 420c2 longer than the oligonucleotide barcodes 404. The same sequence or different sequences can be added to generate the spacer oligonucleotides 420c2 of a synthetic particle 400c2. In some embodiments, the number of different sequences added to generate the spacer oligonucleotides 420c2 can be, or be about, 1, 2, 3, 4, 5, 6, 7, 9, 10, 20, 30, 40, 50, 60, 70, 80, 90, 100, 200, 300, 400, 500, 600, 700, 800, 900, 1000, or a number or a range between any two of these values. In some embodiments, the number of different sequences added to generate the spacer oligonucleotides 420c2 can be at least, or at most, 1, 2, 3, 4, 5, 6, 7, 9, 10, 20, 30, 40, 50, 60, 70, 80, 90, 100, 200, 300, 400, 500, 600, 700, 800, 900, or 1000. The spacer oligonucleotides 420c2 of a synthetic particle 400c2 can have the same sequence or different sequences. In some embodiments, the spacer oligonucleotides 420c2 can have, or have about, 1, 2, 3, 4, 5, 6, 7, 9, 10, 20, 30, 40, 50, 60, 70, 80, 90, 100, 200, 300, 400, 500, 600, 700, 800, 900, 1000, or a number or a range between any two of these values, sequences. In some embodiments, the spacer oligonucleotides 420c2 can have at least, or have at most, 1, 2, 3, 4, 5, 6, 7, 9, 10, 20, 30, 40, 50, 60, 70, 80, 90, 100, 200, 300, 400, 500, 600, 700, 800, 900, or 1000 different sequences. The spacer oligonucleotides 420c2 of a synthetic particle 400c2 can have the same length or different lengths. In some embodiments, the spacer oligonucleotides 420c2 can have, or have about, 1, 2, 3, 4, 5, 6, 7, 9, 10, 20, 30, 40, 50, 60, 70, 80, 90, 100, 200, 300, 400, 500, 600, 700, 800, 900, 1000, or a number or a range between any two of these values, different lengths. In some embodiments, the spacer oligonucleotides 420c2 can have at least, or have at most, 1, 2, 3, 4, 5, 6, 7, 9, 10, 20, 30, 40, 50, 60, 70, 80, 90, 100, 200, 300, 400, 500, 600, 700, 800, 900, or 1000 different lengths. The resulting longer oligonucleotide barcodes on the synthetic particle are referred to herein as spacer oligonucleotides 420c1.

In some embodiments, the density of the oligonucleotide barcodes 404 can be lowered by associating (e.g., coupling) both oligonucleotide barcodes 404 and spacer oligonucleotides 420c2 illustrated in FIG. 4C2 to a synthetic particle 400c2.

The density of the oligonucleotide barcodes can be changed by adjusting the association conditions for associating oligonucleotide barcodes to the synthetic particle (e.g., decreasing the amount of cross-linker, decreasing the amount of oligonucleotide barcodes during coupling). Accurately controlling the degree of association (e.g., coupling) by changing association conditions can require extensive testing. In some embodiments, the density of the oligonucleotide barcodes on a synthetic particle can be initially lowered by adjusting the association condition, and further lowered using an exonuclease or an endonuclease. In some embodiments, the density of the oligonucleotide barcodes can be lowered by associating the oligonucleotide barcodes and spacer oligonucleotides with a synthetic particle under the conditions adjusted to generate a synthetic particle with lower density of oligonucleotide barcodes, and further lowered using an exonuclease or endonuclease.

In some embodiments, the spacer oligonucleotides (e.g., the spacer oligonucleotides associated on a synthetic particle) can have the same length or different lengths. In some embodiments, one or more spacer oligonucleotides can be shorter than one or more oligonucleotide barcodes. For example, a spacer oligonucleotide and an oligonucleotide barcode can be identical except that the oligonucleotide barcode comprises a target-binding region and the spacer oligonucleotide does not. In some embodiments, one or more spacer oligonucleotides can have the same length as one or more oligonucleotide barcodes. For example, a spacer oligonucleotide and an oligonucleotide barcode can be identical in some embodiments except that the oligonucleotide barcode comprises a target-binding region and the spacer oligonucleotide comprises a region with the same length as the target-binding region but with a different nucleotide sequence.

Oligonucleotide Barcodes with Target-Specific Target-Binding Regions

Disclosed herein include embodiments of a synthetic particle. In some embodiments, the synthetic particles comprises: a first plurality of oligonucleotide barcodes; and a second plurality of oligonucleotide barcodes, wherein each of the first plurality of oligonucleotide barcodes and the second plurality of oligonucleotide barcodes comprises an identical cellular label sequence, and a molecular label sequence, wherein at least 10 of the first plurality of oligonucleotide barcodes and the second plurality of oligonucleotide barcodes comprise different molecular label sequences, wherein each of the first plurality of oligonucleotide barcodes comprises a target-binding region, and wherein each of the second plurality of oligonucleotide barcodes comprises a target-specific target-binding region. In some embodiments, the target-binding region of an oligonucleotide barcode of the first plurality of oligonucleotide barcodes comprises a target-specific target-binding region. In some embodiments, the target-binding region of an oligonucleotide barcode of the first plurality of oligonucleotide barcodes comprises a poly(dT) region. An oligonucleotide barcode of the second plurality of oligonucleotide barcodes can comprise a poly(dT) region.

Disclosed herein include embodiments of a method for determining the numbers of targets in a sample. In some embodiments, the method comprises: barcoding copies of a first plurality of targets using a first plurality of oligonucleotide barcodes associated with a synthetic particle to generate copies of a first plurality of barcoded targets; barcoding copies of a second plurality of targets in a sample using a second plurality of oligonucleotide barcodes associated with the synthetic particle to generate copies of a second plurality of barcoded targets, wherein each of the first plurality of oligonucleotide barcodes and the second plurality of oligonucleotide barcodes comprises an identical cellular label sequence and a molecular label sequence, wherein at least 10 of the first plurality of oligonucleotide barcodes and the second plurality of oligonucleotide barcodes comprise different molecular label sequences, wherein each of the first plurality of oligonucleotide barcodes comprises a target-binding region, and wherein each of the second plurality of oligonucleotide barcodes comprises a target-specific target-binding region; and estimating the number of each of the first plurality of targets and/or the second plurality of targets using the molecular label sequences of the first plurality of oligonucleotide barcodes and the second plurality of oligonucleotide barcodes. In some embodiments, the target-binding region of an oligonucleotide barcode of the first plurality of oligonucleotide barcodes comprises a target-specific target-binding region. The target-binding region of an oligonucleotide barcode of the first plurality of oligonucleotide barcodes can comprise a poly(dT) region. An oligonucleotide barcode of the second plurality of oligonucleotide barcodes can comprise a poly(dT) region. In some embodiments, first plurality of targets comprises mRNA molecules of a cell, and wherein the second plurality of targets comprises DNA molecules of the cell. The first plurality of targets can comprise mRNA molecules of a cell, and the second plurality of targets can comprise RNA molecules of a virus, a bacterium, and/or a fungus infecting the cell.

FIGS. 4D1-4D2 are non-limiting exemplary synthetic particles associated with a plurality of oligonucleotide barcodes with target-specific target-binding regions. The target-binding regions of the oligonucleotide barcodes on a synthetic particle can include, or can be, target-specific target-binding regions and/or non-target specific target-binding regions (e.g., poly(dT) regions and random multimers). The target-binding regions of the oligonucleotide barcodes on a synthetic particle (e.g., a synthetic particle associated with spacer oligonucleotides) can include, or be, poly(dT) regions 404, random multimers, and/or target-specific sequences 412*d* (e.g., sequences capable of hybridizing to one or more targets of interests). For example, the oligonucleotide barcodes 404*d*1 associated with a synthetic particle 400*d*1 can include target-binding regions 412*d*1 capable of specifically binding a number of targets of interest (for example, four targets of interests, such as CD4, IL2, CD8, and CR7) and oligonucleotide barcodes 404 with poly(dT) regions 412 (FIG. 4D1).

In some embodiments, the targets of interests can include an oligonucleotide conjugated to a cellular component-binding reagent (e.g., a protein binding reagent, such as an antibody or a protein-binding aptamer), wherein the oligonucleotide comprises a unique identifier for the cellular component-binding reagent that it is conjugated with. Cellular component-binding reagents associated with oligonucleotides (such as barcoded antibodies) and their uses (such as sample indexing, identification, or tracking of cells and samples, and protein expression profiling) have been described in U.S. Patent Application Publication No. US2018/0088112 and U.S. Patent Application Publication No. US2018/0346970; the content of each of these is incorporated herein by reference in its entirety.

Sample Indexing, Identification, or Tracking.

In some embodiments, performing sample indexing, identification, or tracking can comprise: contacting one or more cells from each of a plurality of samples with a sample indexing composition of a plurality of sample indexing compositions, wherein each of the one or more cells comprises one or more cellular component targets (e.g., protein targets), wherein at least one sample indexing composition of the plurality of sample indexing compositions comprises two or more cellular component binding reagents (e.g., antigen binding reagents or antibodies), wherein each of the two or more cellular component binding reagents is associated with a sample indexing oligonucleotide, wherein at least one of the two or more cellular component binding reagents is capable of specifically binding to at least one of the one or more cellular component targets, wherein the sample indexing oligonucleotide comprises a sample indexing sequence, and wherein sample indexing sequences of at least two sample indexing compositions of the plurality of sample indexing compositions comprise different sequences; barcoding the sample indexing oligonucleotides using a plurality of barcodes (e.g., oligonucleotide barcodes associated with a synthetic particle) to create a plurality of barcoded sample indexing oligonucleotides; obtaining sequencing data of the plurality of barcoded sample indexing oligonucleotides; and identifying sample origin of at least one cell of the one or more cells based on the sample indexing sequence of at least one barcoded sample indexing oligonucleotide of the plurality of barcoded sample indexing oligonucleotides. In some embodiments, the sample indexing sequence is 25-60 nucleotides in length (e.g., 45 nucleotides in length), about 128 nucleotides in length, or at least 128 nucleotides in length. Sample indexing sequences of at least 10 sample indexing compositions of the plurality of sample indexing compositions can comprise different sequences. Sample indexing sequences of at least 10 sample indexing compositions of the plurality of sample indexing compositions can comprise different sequences. Sample indexing sequences of at least 10 sample indexing compositions of the plurality of sample indexing compositions comprise different sequences. In some embodiments, the sample indexing oligonucleotide is not homologous to genomic sequences of the cells of the plurality of samples. The sample indexing oligonucleotide can comprise a molecular label sequence, a binding sequence that the target-binding region of a barcode can bind (e.g., hybridize) to (e.g., a poly(A) region, or a non-poly(A) region), or a combination thereof. The sample indexing oligonucleotide can comprise a sequence complementary to a capture sequence (e.g., a target binding region) of at least one barcode of the plurality of barcodes. A target binding region of the barcode can comprise the capture sequence. The target binding region can comprise, for example, a poly(dT) region. The sequence of the sample indexing oligonucleotide complementary to the capture sequence of the barcode can comprise a poly(dA) tail, for example. The sample indexing oligonucleotide can comprise a molecular label in some embodiments.

Expression Profiling.

In some embodiments, performing protein expression profiling (or profiling of cellular component targets) can comprise: providing a sample comprising a plurality of protein targets (or other cellular component targets, such as carbohydrates, lipids, etc.); providing a plurality of compositions each comprising a protein binding reagent (or a cellular component binding reagent) conjugated with an oligonucleotide, wherein the oligonucleotide comprises a unique identifier for the protein binding reagent that it is conjugated therewith, and the protein binding reagent (or cellular component binding reagent) is capable of specifically binding to at least one of the plurality of protein targets (or cellular component targets); contacting the plurality of compositions with the sample for specific binding with the plurality of protein targets (or cellular component targets); removing unbound compositions; providing a plurality of oligonucleotide probes (e.g., oligonucleotide barcodes associated with a synthetic particle), wherein each of the plurality of oligonucleotide probes comprises a target binding region and a barcode sequence (e.g., a molecular label sequence), wherein the barcode sequence is from a diverse set of unique barcode sequences; contacting the plurality of oligonucleotide probes with the oligonucleotides of the plurality of compositions; extending the oligonucleotide probes hybridized to the oligonucleotides to produce a plurality of labeled nucleic acids, wherein each of the labeled nucleic acid comprises a unique identifier and a barcode sequence; and determining the number of unique barcode sequences for each unique identifier, whereby the quantity of each protein target in the sample is determined. In some embodiments, the unique identifier comprises a nucleotide sequence of 25-45 nucleotides in length. In some embodiments, the unique identifier is selected from a diverse set of unique identifiers. In some embodiments, the diverse set of unique identifiers comprises at least 100 different unique identifiers. In some embodiments, the diverse set of unique identifiers comprises at least 1,000 different unique identifiers. In some embodiments, the diverse set of unique identifiers comprises at least 10,000 different unique identifiers. In some embodiments, the plurality of compositions comprises a plurality of antibodies, a plurality of aptamers, or a combination thereof. In some embodiments, the oligonucleotide is conjugated to the protein binding reagent through a linker. In some embodiments, the linker comprises a chemical group. In some embodiments, the oligonucleotide comprises the linker. In some embodiments, the chemical group is reversibly attached to the protein binding reagent. In some embodiments, the chemical group is selected from the group consisting of a UV photocleavable group, a streptavidin, a biotin, an amine, and any combination thereof. In some embodiments, the sample comprises a single cell. In some embodiments, the plurality of protein targets is expressed on the surface of the single cell. In some embodiments, the removing unbound compositions comprises washing the single cell with a washing buffer. In some embodiments, the methods comprise lysing the single cell. In some embodiments, the methods comprise detaching the oligonucleotides from the protein binding reagents. In some embodiments, the oligonucleotides are detached from the protein binding reagent by UV photocleaving, chemical treatment (dithiothreitol), heating, enzyme treatment, or any combination thereof. In some embodiments, each of the oligonucleotide probes comprises a cell label, a binding site for a universal primer, or any combination thereof. In some embodiments, the target binding region comprises poly(dT). In some embodiments, the plurality of oligonucleotide probes is immobilized on a solid support. In some embodiments, the solid support is a bead. In some embodiments, the methods further comprise amplifying the plurality of labeled nucleic acids to produce a plurality of amplicons. In some embodiments, the amplifying comprises PCR amplification of at least a portion of the barcode sequence, and at least a portion of the unique identifier. In some embodiments, the diverse set of unique barcode sequences comprises at least 100 unique barcode sequences. In some embodiments, the diverse set of unique barcode sequences comprises at least 1,000 unique barcode sequences. In some embodiments, the diverse set of unique barcode sequences comprises at least 10,000 unique barcode sequences. The plurality of compositions can further comprise a second protein binding reagent not conjugated with the oligonucleotide. The protein binding reagent and the second protein binding reagent can be the same. In some embodiments, the methods further comprise sequencing the plurality of amplicons. In some embodiments, the sequencing comprises sequencing at least a portion of the barcode sequence, and at least a portion of the unique identifier. The method can be used for simultaneous quantitative analysis of a plurality of protein targets and a plurality of nucleic acid target molecules in a sample.

In some embodiments, the oligonucleotide conjugated to a cellular component-binding reagent can have a poly(dA) region 416 that can hybridize to the poly(dT) region 412 of an oligonucleotide barcode 404. In some embodiments, an oligonucleotide barcode 404d1 can have a target-specific target-binding region 412d that can specifically hybridize to and capture an oligonucleotide associated with a cellular component-binding reagent. The region of the oligonucleotide associated with a cellular component-binding reagent that the target-specific target-binding region 412 binds or hybridizes to can be at the 3' end of the oligonucleotide that corresponds to the poly(dA) region of an mRNA, at the 5' end of the oligonucleotide, or internal to the oligonucleotide. In some embodiments, the oligonucleotide is dissociated from the cellular component-binding reagent prior to being captured by the oligonucleotide barcode 404d1 with a target-specific target-binding region 412d.

As illustrated in FIG. 4D1, the poly(dT) regions of oligonucleotide barcodes 404 can capture (e.g., hybridize to) targets, such as mRNA molecules, with poly(A) tails 416. The poly(dT) regions 412 of oligonucleotide barcodes 404 can capture targets with poly(A) regions or tails 416. The target-specific target-binding regions 412d of oligonucleotide barcodes 404d1 can capture (e.g., hybridize to) targets of interests. For example, a target-specific target-binding region 412d can include, or can be, a partial CD4 sequence that can hybridize to the non-poly(A) region 416d (or a region 416d of the CD4 mRNA with a non-A base) of a CD4 mRNA molecule and capture the CD4 mRNA molecule. As another example, a target-specific target-binding region 412d can include, or can be, a sequence for capturing targets, such as viral mRNAs, without poly(A) tails. In some embodiments, the synthetic particle 400d1 can be used to simultaneously determine phenotypes and/or phenotypes of cells infected with viruses and genotypes and/or phenotypes of the viruses. For example, the synthetic particle 400d1 can include oligonucleotide barcodes 404 with poly(dT) regions 412 for capturing mRNAs of infected cells and oligonucleotide barcodes 404d1 with target-specific target-binding regions 412d for capturing viral RNAs (e.g., viral mRNAs). In some embodiments, the bead 400d1 can be generated by associating (e.g., coupling) oligonucleotide barcodes 404 with poly(dT) regions 412 and oligonucleotide barcodes 404d1 with target-specific target-binding regions 412d to a synthetic particle 400d1.

Referring to FIG. 4D2, the oligonucleotide barcodes 404d2 associated with a synthetic particle 400d2 can include target-binding regions 412d1, capable of specifically binding a number of targets of interests, and a poly(dT) region 404 (FIG. 4D2). As illustrated in FIG. 4D2, the synthetic particle 400d2 can also include oligonucleotide barcodes 404 with non-target-specific target-binding regions (e.g., a poly(dT) region 400). As illustrated in FIG. 4D2, the poly(dT) regions 412 of oligonucleotide barcodes 404 can capture (e.g., hybridize to) targets, such as mRNA molecules, with poly(A) tails 416. The poly(dT) regions 412 of oligonucleotide barcodes 404 can capture targets with poly(A) regions or tails 416. The target-specific target-binding regions 412d of oligonucleotide barcodes 404d2 can capture (e.g., hybridize to) targets of interests. As illustrated in FIG. 4D2, the oligonucleotide barcodes 404d2 with target-specific target-binding regions 412d can include poly(dT) regions 412 in some embodiments. In some embodiments, the synthetic particle 400d2 can be used to simultaneously determine phenotypes and/or phenotypes of cells infected with viruses and genotypes and/or phenotypes of the viruses. For example, the synthetic particle 400d2 can include oligonucleotide barcodes 404 with poly(dT) regions 412 for capturing mRNAs of infected cells and oligonucleotide barcodes 404d2 with target-specific target-binding regions 412d for capturing viral RNAs (e.g., viral mRNAs).

In some embodiments, the bead 400d2 can be generated by associating (e.g., coupling) oligonucleotide barcodes 404 with poly(dT) regions 412 and oligonucleotide barcodes 404d2 with target-specific target-binding regions 412d and poly(dT) regions 412 to a synthetic particle 400d. In some embodiments, a synthetic particle 400d2 associated with oligonucleotide barcodes 404 with the same sequence (or poly(dT) regions 412) can be first generated. An enzyme, such as a polymerase or a ligase, can be used to add target-specific target-binding regions 412d, by extension or ligation, to some of the oligonucleotide barcodes 404 to generate oligonucleotide barcodes 404d2 with target-specific target-binding regions 412d and poly(dT) regions 412. For example, a single-stranded DNA template with a poly (dA) sequence (e.g., on the 3' end of the template) and a partial sequence of the target of interest (e.g., on the 5' end of the template) can hybridize to the poly(dT) region 412 of an oligonucleotide barcode 404, which can be extended by a polymerase to generate an oligonucleotide barcode 404d2 with the target-specific target-binding region 412d and the poly(dT) region 412. As another example, an oligonucleotide barcode 404d2 with a target-specific target-binding region 412 and a poly(dT) region 412 can be generated using a partial duplex DNA template. One strand of the partial duplex DNA template can include a poly(dA) sequence (e.g., on the 5' end of the strand) and a partial sequence of the target of interest (e.g., on the 3' end of the strand). The other strand of the partial duplex DNA template can include a target-specific target-binding region. The partial duplex DNA template can be formed by the hybridization of the partial sequence of the target of interest on one strand and the target-specific target-binding region on the other strand. The partial duplex DNA template can hybridize to an oligonucleotide barcode 404 via hybridization of the poly (dT) region 412 of the oligonucleotide barcode 404 and the poly(dA) sequence of the partial duplex DNA template. After hybridization, the partial duplex DNA template can be ligated to the oligonucleotide barcode 404 with the poly(dT) region 412 using a ligase. The strand of the template with the poly(dA) sequence can be removed by denaturing the partial duplex DNA template ligated to the oligonucleotide barcode 404 to generate the oligonucleotide barcode 404 with a target-specific target-binding region 412d and a poly(dT) region 412. The synthetic particle 400d1, 400d2 can include spacer oligonucleotides (not shown).

FIGS. 5A-5C show a non-limiting exemplary comparison of an oligonucleotide barcode 404 with a poly(dT) region 412 capable of hybridizing to a poly(A) tail of an mRNA molecule (FIG. 5A), an oligonucleotide barcode 404d1 with a target-specific target-binding region 412 capable of binding to one or more genes of interests, and an oligonucleotide barcode 404d2 with poly(dT) region 412 and a target-specific target-binding region 412d. The oligonucleotide barcodes 404, 404d1, 404d2 can be associated with a single synthetic particle.

In some embodiments, instead of coupling (e.g., covalently coupling) poly(dT) oligonucleotides (for capturing mRNA via poly(A) tails) to particles, such as synthetic particles or beads, oligonucleotide barcodes with a variety of target-specific sequences 412 (e.g., gene specific) can be coupled to particles. These oligonucleotides can have a similar structure as the oligonucleotides with poly(dT) regions 404. The oligonucleotide barcodes 404d1, 404d2 can have different sequences for capturing RNA (including RNA molecules without poly(A) tails). For example, the particles can allow capturing of a specific subset of RNAs, depending on the targets of the coupled oligonucleotides 404d1, 404d2. Since a single cell has about 300,000 mRNA molecules, the number of oligonucleotide barcodes with poly(dT) regions that need to be coupled onto each particle to capture all the mRNA molecules is large (e.g., larger than 300,000), even if only a subset of these molecules will eventually be amplified with a targeted gene panel. With target-specific oligonucleotide barcodes 404d1, 404d2, a more selective set of cDNA molecules can be generated because only mRNA molecules for subsequent amplification and sequencing are captured. Furthermore, the number of molecules (e.g., for each gene or for all genes of interests) for subsequent amplification and sequencing is likely much lower than 300,000 copies, so fewer oligonucleotide barcodes 404d1, 404d2 targeting that gene or all genes of interests needs to be coupled to the particle. The particles can be coupled with oligonucleotide barcodes 404d1, 404d2 capable of specifically capturing mRNA molecules of genes that are expected to be expressed by one or more cell type (e.g., CD4+ helper T cells). Thus, only mRNA molecules of these genes can be captured and further analyzed (e.g., expression quantification).

First Plurality of Oligonucleotides (e.g., Spacer Oligonucleotides, and Target-Specific Oligonucleotide Barcodes)

Disclosed herein are embodiments of a synthetic particle. In some embodiments, the synthetic particle (e.g., the synthetic particles 400b, 400c1, 400c2 described with reference to FIGS. 4B and 4C1-4C2) comprises: a plurality of oligonucleotide barcodes (e.g., the oligonucleotide barcodes 404 in FIGS. 4B and 4C1-4C2 and the oligonucleotide barcodes 404d1, 404d2 in FIGS. 4D1-4D2). Each of the plurality of oligonucleotide barcodes 404, 404d1, 404d, can comprise an identical cellular label, a molecular label, and a target-binding region (e.g., the target-binding regions 412, 412d1, 412d2 in FIGS. 4B, 4C1-4C2, and 4D1-4D2). At least, or at most, 10, 100, 1000, 10000, 100000, or more of the plurality of oligonucleotide barcodes can comprise different molecular label sequences. The synthetic particle can include a first plurality of spacer oligonucleotides (e.g., the spacer oligonucleotides 420b, 420c1, 420c2, described with reference to FIGS. 4B and 4C1-4C2).

In some embodiments, the number of first plurality of spacer oligonucleotides (or oligonucleotide barcodes with target-specific target-binding regions, referred to herein as target-specific oligonucleotide barcodes) can be, or can be about, 0, 1, 2 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$, $10^7$, $10^8$, $10^9$, or a number or a range between any two of these values. In some embodiments, the number of first plurality of spacer oligonucleotides (or oligonucleotide barcodes with target-specific target-binding regions) can be at least, or at most, 0, 1, 2 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$, $10^7$, $10^8$, or $10^9$.

The ratio of the plurality of oligonucleotide barcodes and the first plurality of spacer oligonucleotides (or oligonucleotide barcodes with target-specific target-binding regions) can be different in different implementations, ranging from $1:10^9$ to $10^9:1$. As used herein, the ratio of two pluralities of oligonucleotides refers to the ratio between the number of oligonucleotides in the first plurality of oligonucleotides and the number of oligonucleotides in the second plurality of oligonucleotides. In some embodiments, the ratio of the plurality of oligonucleotide barcodes and the first plurality of spacer oligonucleotides (or oligonucleotide barcodes with target-specific target-binding regions) can be, or can be about, 1:1, 1:2, 1:3, 1:4, 1:5, 1:6, 1:7, 1:8, 1:9, 1:10, 1:20, 1:30, 1:40, 1:50, 1:60, 1:70, 1:80, 1:90, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, $1:10^4$, $1:10^5$, $1:10^6$, $1:10^7$, $1:10^8$, $1:10^9$, or a number or a range between any two of these values. In some embodiments, the ratio of the plurality of oligonucleotide barcodes and the first plurality of spacer oligonucleotides can be at least, or at most, 1:1, 1:2, 1:3, 1:4, 1:5, 1:6, 1:7, 1:8, 1:9, 1:10, 1:20, 1:30, 1:40, 1:50, 1:60, 1:70, 1:80, 1:90, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, $1:10^4$, $1:10^5$, $1:10^6$, $1:10^7$, $1:10^8$, or $1:10^9$. In some embodiments, the ratio of the plurality of oligonucleotide barcodes and the first plurality of spacer oligonucleotides (or oligonucleotide barcodes with target-specific target-binding regions) can be, or can be about, 1:1, 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, $10^4:1$, $10^5:1$, $10^6:1$, $10^7:1$, $10^8:1$, $10^9:1$, or a number or a range between any two of these values. In some embodiments, the ratio of the plurality of oligonucleotide barcodes and the first plurality of spacer oligonucleotides (or oligonucleotide barcodes with target-specific target-binding regions) can be at least, or at most, 1:1, 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, $10^4:1$, $10^5:1$, $10^6:1$, $10^7:1$, $10^8:1$, or $10^9:1$.

A spacer oligonucleotide (or an oligonucleotide barcode with a target-specific target-binding region) can be shorter, have the same length, or longer than an oligonucleotide barcode. The number of spacer oligonucleotides (or oligonucleotide barcodes with target-specific target-binding regions) that is shorter, have the same length, or that is longer than every oligonucleotide barcode (or at least one oligonucleotide barcode) can be different in different implementations. In some embodiments, the number of spacer oligonucleotides (or oligonucleotide barcodes with target-specific target-binding regions) that is shorter, have the same length, or that is longer than every oligonucleotide barcode (or at least one oligonucleotide barcode) can be, or can be about, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$, $10^7$, $10^8$, $10^9$, or a number or a range between any two of these values. In some embodiments, the number of spacer oligonucleotides (or oligonucleotide barcodes with target-specific target-binding regions) that is shorter, have the same length, or that is longer than every oligonucleotide barcode (or at least one oligonucleotide barcode) can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$, $10^7$, $10^8$, or $10^9$. For example, at least one of the first plurality of spacer oligonucleotides can be shorter than at least one of the plurality of oligonucleotide barcodes.

In some embodiments, the number of oligonucleotide barcodes that is shorter, have the same length, or that is longer than every (or at least one) spacer oligonucleotide (or oligonucleotides with target-specific target-binding regions) can be, or can be about, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$, $10^7$, $10^8$, $10^9$, or a number or a range between any two of these values. In some embodiments, the number of oligonucleotide barcodes that is shorter, have the same length, or that is longer than every (or at least one)

spacer oligonucleotide (or oligonucleotide barcodes with target-specific target-binding regions) can be at least, or at most, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$, $10^7$, $10^8$, or $10^9$.

Each of the first plurality of spacer oligonucleotides may not comprise the target-binding region. For example, a spacer oligonucleotide 420b illustrated in FIG. 4B can include a spacer region 424b, corresponding to the target-binding region, not capable for hybridizing to targets of interests. As another example, a spacer oligonucleotide 420c1 illustrated in FIG. 4C1 be shorter than an oligonucleotide barcode 404, lacking the target-binding region 412. As another example, a spacer oligonucleotide 420c1 illustrated in FIG. 4C2 be longer than an oligonucleotide barcode 404. Each of the first plurality of spacer oligonucleotides (or oligonucleotide barcodes with target-specific target-binding regions) can comprise a cellular label or a molecular label. Each of the first plurality of spacer oligonucleotides can comprise a region that corresponds to the target-binding region (referred to herein as a spacer region, such as the spacer region 424b in FIG. 4B).

The region 424b that corresponds to the target-binding region and the target-binding region (or two target-binding regions) can have different sequences. A spacer region 424b and a target-binding region (or two target-binding regions) can different. The sequence identity between a spacer region 424b and a target-binding region (or between two target-binding regions, such as a poly(dT) region 412 and a target-specific target-binding region 412d) can be different in different implementations, ranging from 1% to 99%. In some embodiments, the sequence identity between a spacer region 424b and a target-binding region 412, 412d (or two target-binding regions) can be, or can be about, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or a number or a range between any two of these values. In some embodiments, the sequence identity between a spacer region 424b and a target-binding region 412, 412d (or between two target-binding regions) can be at least, or at most, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. For example, the region 424b that corresponds to the target-binding region and the target-binding region 412, 412d (or two target-binding regions) can have at most 50% sequence identity. In some embodiments, a spacer region 424b and a target-binding region 412, 412d (or two target-binding regions) can differ from each other by, or by about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or a number or a range between any two of these values. In some embodiments, a spacer region 424b and a target-binding region 412, 412d (or two target-binding regions) can differ from each other by at least, or at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

The number of the first plurality of spacer oligonucleotides (or oligonucleotide barcodes with target-specific target-binding regions) that have different lengths (e.g., the spacer oligonucleotides 420c1, 420c2 in FIGS. 4C1-4C2) can be different in different implementations. In some embodiments, the number of the first plurality of spacer oligonucleotides (or oligonucleotide barcodes with target-specific target-binding regions) that have different lengths can be, or can be about, 0, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$, $10^7$, $10^8$, $10^9$, or a number or a range between any two of these values. In some embodiments, the number of the first plurality of spacer oligonucleotides (or oligonucleotide barcodes with target-specific target-binding regions) that have different lengths can be at least, or at most, 0, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$, $10^7$, $10^8$, or $10^9$. For example, at least two of the first plurality of spacer oligonucleotides (or oligonucleotide barcodes with target-specific target-binding regions) can have different lengths. In some embodiments, the percentage of the first plurality of spacer oligonucleotides (or oligonucleotide barcodes with target-specific target-binding regions) that have different lengths can be, or can be about, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the percentage of the first plurality of spacer oligonucleotides (or oligonucleotide barcodes with target-specific target-binding regions) that have different lengths can be at least, or at most, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

The number of the first plurality of spacer oligonucleotides (or oligonucleotide barcodes with target-specific target-binding regions) with an identical sequence can be different in different implementations. In some embodiments, the number of the first plurality of spacer oligonucleotides (or oligonucleotide barcodes with target-specific target-binding regions) with an identical sequence can be, or can be about, 0, 1, 2 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$, $10^7$, $10^8$, $10^9$, or a number or a range between any two of these values. In some embodiments, the number of the first plurality of spacer oligonucleotides (or oligonucleotide barcodes with target-specific target-binding regions) with an identical sequence can be at least, at most, 0, 1, 2 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$, $10^7$, $10^8$, or $10^9$. For example, sequences of at least two of the first plurality of spacer oligonucleotides (or oligonucleotide barcodes with target-specific target-binding regions) can be identical. The number of the first plurality of spacer oligonucleotides (or oligonucleotide barcodes with target-specific target-binding regions) with an identical subsequence can be different in different implementations. In some embodiments, the number of the first plurality of spacer oligonucleotides (or oligonucleotide barcodes with target-specific target-binding regions) with an identical subsequence can be, or can be about, 0, 1, 2 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$, $10^7$, $10^8$, $10^9$, or a number or a range between any two of these values. In some embodiments, the number of the first plurality of spacer oligonucleotides (or oligonucleotide barcodes with target-specific target-binding regions) with an identical subsequence can be at least, at most, 0, 1, 2 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$, $10^7$, $10^8$, or $10^9$. For example, at least two of the first plurality of spacer oligonucleotides (or oligonucleotide barcodes with target-specific target-binding regions) can comprise an identical sequence.

Second Plurality of Oligonucleotides (e.g., Spacer Oligonucleotides, and Target-Specific Oligonucleotide Barcodes)

In some embodiments, the synthetic particle comprises a second plurality of spacer oligonucleotides (or oligonucleotide barcodes with target-specific target-binding regions). Each of the second plurality of spacer oligonucleotides may not comprise the target-binding region. One or more of the first plurality of spacer oligonucleotides and one or more of the second plurality of spacer oligonucleotides can have the same length and different nucleotide sequences. One or more of the first plurality of spacer oligonucleotides and one or more of the second plurality of spacer oligonucleotides can have different lengths and similar or different nucleotide sequences. One or more of the first plurality of target-specific oligonucleotides and one or more of the second plurality of target-specific oligonucleotides can have the same length and different nucleotide sequences. One or more of the first plurality of target-specific oligonucleotides and one or more of the second plurality of target-specific oligonucleotides can have different lengths and similar or different nucleotide sequences.

In some embodiments, the number of second plurality of spacer oligonucleotides (or oligonucleotide barcodes with target-specific target-binding regions) can be, or can be about, 0, 1, 2 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$, $10^7$, $10^8$, $10^9$, or a number or a range between any two of these values. In some embodiments, the number of second plurality of spacer oligonucleotides (or oligonucleotide barcodes with target-specific target-binding regions) can be at least, or at most, 0, 1, 2 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$, $10^7$, $10^8$, or $10^9$.

Second spacer oligonucleotides of the second plurality of spacer oligonucleotides (or second target-specific oligonucleotide barcodes of the second plurality target specific oligonucleotide barcodes) can have different lengths. The number of the second plurality of spacer oligonucleotides (or target-specific oligonucleotide barcodes) can be shorter, can have the same length, or can be longer than at least one, or each, of the first plurality of spacer oligonucleotides (or target-specific oligonucleotide barcodes). In some embodiments, the number of the second plurality of spacer oligonucleotides (or target-specific oligonucleotide barcodes) that is shorter, have the same length, or is longer than at least one, or each, of the first plurality of spacer oligonucleotides (or target-specific oligonucleotide barcodes) can be, or can be about, 0, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$, $10^7$, $10^8$, $10^9$, or a number or a range between any two of these values. In some embodiments, the number of the second plurality of spacer oligonucleotides (or target-specific oligonucleotide barcodes) that is shorter, have the same length, or is longer than at least one, or each, of the first plurality of spacer oligonucleotides (or target-specific oligonucleotide barcodes) can be at least, or at most, 0, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$, $10^7$, $10^8$, or $10^9$. For example, at least one of the second plurality of spacer oligonucleotides (or target-specific oligonucleotide barcodes) can be shorter than at least one of the first plurality of spacer oligonucleotides (or target-specific oligonucleotide barcodes). In some embodiments, the percentage of the second plurality of spacer oligonucleotides (or target-specific oligonucleotide barcodes) that is shorter, have the same length, or is longer than at least one, or each, of the first plurality of spacer oligonucleotides (or target-specific oligonucleotide barcodes) can be, or can be about, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the percentage of the second plurality of spacer oligonucleotides (or target-specific oligonucleotide barcodes) that is shorter, have the same length, or is longer than at least one, or each, of the first plurality of spacer oligonucleotides (or target-specific oligonucleotide barcodes) can be, or can be about, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

In some embodiments, the number of the second plurality of spacer oligonucleotides (or target-specific oligonucleotide barcodes) that is shorter, have the same length, or is longer than at least one, or each, of the second plurality of spacer oligonucleotides (or target-specific oligonucleotide barcodes) can be, or can be about, 0, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$, $10^7$, $10^8$, $10^9$, or a number or a range between any two of these values. In some embodiments, the number of the first plurality of spacer oligonucleotides (or target-specific oligonucleotide barcodes) that is shorter, have the same length, or is longer than at least one, or each, of the second plurality of spacer oligonucleotides (or target-specific oligonucleotide barcodes) can be at least, or at most, 0, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$, $10^7$, $10^8$, or $10^9$. For example, at least one of the second plurality of spacer oligonucleotides (or target-specific oligonucleotide barcodes) can be shorter than at least one of the plurality of spacer oligonucleotides (or target-specific oligonucleotide barcodes). In some embodiments, the percentage of the first plurality of spacer oligonucleotides (or target-specific oligonucleotide barcodes) that is shorter, have the same length, or is longer than at least one, or each, of the second plurality of spacer oligonucleotides (or target-specific oligonucleotide barcodes) can be, or can be about, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the percentage of the first plurality of spacer oligonucleotides (or target-specific oligonucleotide barcodes) that is shorter, have the same length, or is longer than at least one, or each, of the second plurality of spacer oligonucleotides (or target-specific oligonucleotide barcodes) can be, or can be about, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

The number of the second plurality of spacer oligonucleotides (or target-specific oligonucleotide barcodes) that have different can be different in different implementations. In some embodiments, the number of the second plurality of spacer oligonucleotides (or target-specific oligonucleotide barcodes) that have different lengths can be, or can be about, 0, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$, $10^7$, $10^8$, $10^9$, or a number or a range between any two of these values. In some embodiments, the number of the second plurality of spacer oligonucleotides (or target-specific oligonucleotide barcodes) that have different lengths can be at least, or at most, 0, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$, $10^7$, $10^8$, or $10^9$. For example, at least two of the second plurality of spacer oligonucleotides can have different lengths. In some embodiments, the percentage of the second plurality of spacer oligonucleotides (or target-specific oligonucleotide barcodes) that have different lengths can be, or can be about, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the percentage of the second plurality of spacer oligonucleotides (or target-specific oligonucleotide barcodes) that have different lengths can be at least, or at most, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

The number of the second plurality of spacer oligonucleotides (or target-specific oligonucleotide barcodes) with an identical sequence can be different in different implementations. In some embodiments, the number of the second plurality of spacer oligonucleotides (or target-specific oligonucleotide barcodes) with an identical sequence can be, or can be about, 0, 1, 2 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$, $10^7$, $10^8$, $10^9$, or a number or a range between any two of these values. In some embodiments, the number of the second plurality of spacer oligonucleotides (or target-specific oligonucleotide barcodes) with an identical sequence can be at least, at most, 0, 1, 2 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$, $10^7$, $10^8$, or $10^9$. For example, sequences of at least two of the second plurality of spacer oligonucleotides (or target-specific oligonucleotide barcodes) can be identical. The number of the second plurality of spacer oligonucleotides (or target-specific oligonucleotide barcodes) with an identical subsequence can be different in different implementations. In some embodiments, the number of the second plurality of spacer oligonucleotides (or target-specific oligonucleotide barcodes) with an identical subsequence can be, or can be about, 0, 1, 2 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$, $10^7$, $10^8$, $10^9$, or a number or a range between any two of these values. In some embodiments, the number of the second plurality of spacer oligonucleotides (or target-specific oligonucleotide barcodes) with an identical subsequence can be at least, at most, 0, 1, 2 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$, $10^7$, $10^8$, or $10^9$. For example, at least two of the second plurality of spacer oligonucleotides (or target-specific oligonucleotide barcodes) can comprise an identical sequence.

Target-Binding Region

As illustrated in FIGS. 4B and 4C1-4C2, a synthetic particle 400b, 400c1, 400c2, can include spacer oligonucleotides 420b, 420c1, 420c2 and oligonucleotide barcodes 404. The oligonucleotide barcodes 404 can include target-binding regions 412 capable of capturing (e.g., hybridizing) targets molecules 408. The spacer oligonucleotides 420b can include spacer regions 424b, corresponding to the target-binding regions 412, not capable of capturing (e.g., hybridizing to) target molecules 408 (or a subset of the target molecules). The spacer oligonucleotides 420c1, 420c2 can include or lack regions that correspond to the target-binding regions 412. Including spacer oligonucleotides 420b, 420c1, 420c2 on a synthetic particle 400b, 400c1, 400c2 can improve target 408 capture (e.g., mRNA capture) and subsequent quantification of target molecules 408 captured. For example, a synthetic particle 400b, 400c1, 400c2 can be coupled with both oligonucleotide barcodes 404 (e.g., barcodes each with a poly(dT) region that can bind to a copy or an occurrence of a mRNA molecule or species) and spacer oligonucleotides 420b, 420c1, 420c2, which can improve mRNA capture and gene expression quantification. In some embodiments, a target-binding region can hybridize with a target of interest. In some embodiments, a target-binding region can comprise a nucleic acid sequence that hybridizes specifically to a target (e.g. target nucleic acid, such as a cellular nucleic acid to be analyzed). For example, a target-binding region can hybridize to a target nucleic acid at a specific gene sequence. In some embodiments, a target-binding region can comprise a nucleic acid sequence that can attach (e.g., hybridize) to a specific location of a specific target nucleic acid. In some embodiments, the target-binding region can comprise a nucleic acid sequence that is capable of specific hybridization to a restriction enzyme site overhang (e.g. an EcoRI sticky-end overhang). The barcode can then ligate to any nucleic acid molecule comprising a sequence complementary to the restriction site overhang.

In some embodiments, a target-binding region can comprise a non-specific target nucleic acid sequence (also referred to herein as non-target specific target-binding region). A non-specific target nucleic acid sequence can refer to a sequence that can bind to multiple target nucleic acids, independent of the specific sequence of the target nucleic acid. For example, target-binding region can comprise a random multimer sequence, or an oligo(dT) sequence that hybridizes to the poly(A) tail on mRNA molecules. A random multimer sequence can be, for example, a random dimer, trimer, quatramer, pentamer, hexamer, septamer, octamer, nonamer, decamer, or higher multimer sequence of any length. In some embodiments, the target-binding region is the same for all barcodes attached to a given synthetic particle (e.g., a bead). In some embodiments, the target-binding regions for the plurality of barcodes attached to a given synthetic particle can comprise two or more different target binding sequences. A target-binding region can be, or be about, 5, 10, 15, 20, 25, 30, 35, 40, 45, 50, or a number or a range between any two of these values, nucleotides in length. A target-binding region can be at most about 5, 10, 15, 20, 25, 30, 35, 40, 45, 50, or more nucleotides in length.

In some embodiments, a target-binding region can comprise an oligo(dT) which can hybridize with mRNAs comprising polyadenylated (poly(A)) ends. A target-binding region can be target-specific (e.g., gene-specific). For example, a target-binding region can be configured to hybridize to a specific region of a target. A target-binding region can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these values, nucleotides in length. A target-binding region can be at least, or at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30, nucleotides in length. A target-binding region can be about 5-30 nucleotides in length. When a barcode comprises a gene-specific target-binding region, the barcode can be referred to herein as a gene-specific barcode.

The target-binding region can comprise a gene-specific sequence, an oligo(dT) sequence, a random multimer, or any combination thereof. The number of target-binding regions of oligonucleotide barcodes of the plurality of oligonucleotide barcodes with different gene-specific sequences can be different in different implementations. In some embodiments, the number of target-binding regions of oligonucleotide barcodes of the plurality of oligonucleotide barcodes with different gene-specific sequences can be, or can be about, 0, 1, 2 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$, $10^7$, $10^8$, $10^9$, or a number or a range between any two of these values. In some embodiments, the number of target-binding regions of oligonucleotide barcodes of the plurality of oligonucleotide barcodes with different gene-specific sequences can be at least, or at most, 0, 1, 2 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$, $10^7$, $10^8$, or $10^9$. In some embodiments, the percentage of target-binding regions of oligonucleotide barcodes of the plurality of oligonucleotide barcodes with different gene-specific sequences can be, or can be about, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the percentage of target-binding regions of oligonucleotide barcodes of the plurality of oligonucleotide barcodes with different gene-specific sequences can be at least, or at most, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%. For example, two target-binding regions of two oligonucleotide barcodes of the plurality of oligonucleotide barcodes can comprise different gene-specific sequences.

In some embodiments, at least, or at most, 100, 1000, 10000, 100000, or more, of the plurality of oligonucleotide barcodes comprise different molecular label sequences. Each cellular label of the plurality of oligonucleotide barcodes can comprise at least, or at most, 1, 2, 3, 4, 5, 6, 7, 8, 9, 10, or more nucleotides. Each molecular label of the plurality of oligonucleotide barcodes can comprise at least, or at most 1, 2, 3, 4, 5, 6, 7, 8, 9, 10, or more nucleotides. Each of the plurality of oligonucleotide barcodes can comprise a spatial label, and wherein spatial labels of the plurality of oligonucleotide barcodes differ from one another by at least one nucleotide. Each of the plurality of oligonucleotide barcodes can comprise a universal label, wherein universal labels of the plurality of oligonucleotide barcodes are the same.

In some embodiments, at least one of the plurality of oligonucleotide barcodes is immobilized, partially immobilized, enclosed, partially enclosed, or any combination thereof, on the synthetic particle. The synthetic particle can be disruptable. The synthetic particle can comprise a particle. The particle can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The synthetic particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. The synthetic particle can comprise a disruptable hydrogel particle. Each of the plurality of oligonucleotide barcodes can comprise a linker functional group, the synthetic particle can comprise a solid support functional group, and/or the support functional group and the linker functional group can be associated with each other. The linker functional group and the support functional group can be individually selected from the group consisting of C6, biotin, streptavidin, primary amine(s), aldehyde(s), ketone(s), and any combination thereof. In some embodiments, the plurality of synthetic particles comprises at least 94 synthetic particles. The kit can comprise a microwell array, wherein each microwell of the microwell array comprises a synthetic particle of the plurality synthetic particles. The kit can comprise a buffer, a cartridge, one or more reagents for a reverse transcription reaction, one or more reagents for an amplification reaction, or an combination thereof.

Disclosed herein include embodiments of a kit or a composition. In some embodiments, the kit or composition comprises: a plurality of synthetic particles, wherein each synthetic particle comprises: a first plurality of oligonucleotide barcodes; and a second plurality of oligonucleotide barcodes, wherein each of the first plurality of oligonucleotide barcodes and the second plurality of oligonucleotide barcodes comprises an identical cellular label sequence and a molecular label sequence, wherein at least 10 of the first plurality of oligonucleotide barcodes and the second plurality of oligonucleotide barcodes comprise different molecular label sequences, wherein each of the first plurality of oligonucleotide barcodes comprises a target-binding region, and wherein each of the second plurality of oligonucleotide barcodes comprises a target-specific target-binding region; and optionally instructions for using the plurality of synthetic particles. In some embodiments, the kit comprises a buffer, one or more reagents for a reverse transcription reaction, one or more reagents for an amplification reaction, or a combination thereof. In some embodiments, the plurality of synthetic particles comprises at least 94 synthetic particles. The kit can comprise a plurality of partitions each comprising a synthetic particle of the plurality synthetic particles. The plurality of partitions can comprise microwells of a microwell array. The plurality of partitions ca comprise a plurality of droplets. In some embodiments, the target-binding region of an oligonucleotide barcode of the first plurality of oligonucleotide barcodes comprises a target-specific target-binding region. The target-binding region of an oligonucleotide barcode of the first plurality of oligonucleotide barcodes can comprise a poly(dT) region. An oligonucleotide barcode of the second plurality of oligonucleotide barcodes can comprise a poly(dT) region.

Provided herein include embodiments of a kit including one or more synthetic particle of the disclosure. In some embodiments, the kit comprises: a plurality of synthetic particles, wherein each synthetic particle comprises: a plurality of oligonucleotide barcodes, wherein each of the plurality of oligonucleotide barcodes comprises an identical cellular label, a molecular label, and a target-binding region, and wherein at least 10 of the plurality of oligonucleotide barcodes comprise different molecular label sequences, and a first plurality of spacer oligonucleotides (or target-specific oligonucleotide barcode), wherein each of the first plurality of spacer oligonucleotides does not comprise the target-binding region. The kit can comprise: instructions for using the plurality of oligonucleotide barcodes.

Barcoding Using Synthetic Particles with Spacer Oligonucleotides

Embodiments disclosed herein include methods for determining the numbers of targets in a sample (described with reference to FIGS. 2 and 3). In some embodiments, the method comprises: barcoding copies of a plurality of targets in a sample using a plurality of oligonucleotide barcodes associated with a synthetic particle to generate copies of a plurality of barcoded targets, wherein each of the plurality of oligonucleotide barcodes comprises an identical cellular label, a molecular label, and a target-binding region, and wherein at least 10, 100, 1000, 10000, or more of the plurality of oligonucleotide barcodes comprise different molecular label sequences, wherein the synthetic particle comprises a first plurality of spacer oligonucleotides, and wherein each of the first plurality of spacer oligonucleotides does not comprise the target-binding region; and estimating the number of each of the plurality of targets in the sample using the molecular labels of the plurality of oligonucleotide barcodes. In some embodiments, barcoding the copies of the plurality of targets in the sample using the plurality of oligonucleotide barcodes associated with the synthetic particle can comprise: hybridizing the plurality of targets to the plurality of oligonucleotide barcodes on the synthetic particle. Barcoding the copies of the plurality of targets can comprise: reverse transcribing the plurality of targets to generate barcoded cDNAs of the plurality of targets. The method can comprise: amplifying the barcoded cDNAs using second strand synthesis to generate barcoded targets, wherein the barcoded targets are double-stranded. The method can comprise: amplifying the barcoded targets to generate labelled target amplicons.

Disclosed herein are embodiments of a method for capturing targets in a sample. In some embodiments, the method comprises: hybridizing copies of a plurality of targets in a sample using a plurality of oligonucleotide barcodes associated with a synthetic particle to generate copies of a plurality of barcoded targets, wherein each of the plurality of oligonucleotide barcodes comprises an identical cellular label, a molecular label, and a target-binding region, and wherein at least 10, 100, 1000, 10000, or more, of the plurality of oligonucleotide barcodes comprise different molecular label sequences, wherein the synthetic particle comprises a first plurality of spacer oligonucleotides, and wherein each of the first plurality of spacer oligonucleotides does not comprise the target-binding region. The method can comprise: reverse transcribing the plurality of targets to generate barcoded cDNAs of the plurality of targets. The method can comprise: amplifying the barcoded cDNAs using second strand synthesis to generate barcoded targets, wherein the barcoded targets are double-stranded. The method can comprise: comprising amplifying the barcoded targets to generate labelled target amplicons.

Copies of the plurality of barcoded targets can comprise a percentage of copies of a target, a number of targets (e.g., 2, 3, 4, 5, 6, 7, 8, 9, 10, or more targets), or each target in the sample, of the plurality of targets in the sample. Such a percentage is a measure or indication of capture efficiency. In some embodiments, the percentage of the copies of a target, two targets, three targets, or each target, of the plurality of targets in the sample hybridized to oligonucleotide barcodes to generate copies of the plurality of barcoded target can be, or can be about, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the percentage of the copies of a target, two targets, three targets, or each target, of the plurality of targets in the sample hybridized to oligonucleotide barcodes to generate copies of the plurality of barcoded target can be at least, or at most, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

In some embodiments, the sample comprises a single cell, the method comprising associating the synthetic particle with the single cell in the sample. The single cell can comprise a rare cell, a tumor cell, a cell from a human, a cell from a tissue, a cell from a tumor, a cell infected with viral polynucleotides, and any combination thereof. The method can comprise: lysing the single cell after associating the synthetic particle with the single cell. The method can comprise: lysing the single cell comprises heating the sample, contacting the sample with a detergent, changing the pH of the sample, or any combination thereof. The synthetic particle and the single cell can be in the same well. The synthetic particle and the single cell can be in the same droplet. The plurality of targets can comprise ribonucleic acids (RNAs), messenger RNAs (mRNAs), microRNAs, small interfering RNAs (siRNAs), RNA degradation products, RNAs each comprising a poly(A) tail, and any combination thereof.

Targets

Targets can be, or include, a DNA target, a RNA target, or a combination thereof. In some embodiments, the targets are mRNA targets with poly(A) tails. For example, the targets can be mRNAs coding for heavy immunoglobulins (e.g., IgA, IgD, IgE1, IgE2, IgG, and IgM) and light immunoglobulins (e.g., IgK, and IgL). For example, a bead with oligonucleotide barcodes with target-binding regions specific to heavy and light immunoglobulins can be used to determine pairings of heavy and light immunoglobulins in immune cells (e.g., such as T-cells, B-cells). Such beads can be used to determine pairings of heavy and light immunoglobulins of antibodies, thus antibody repertoire. In some embodiments, the targets are RNA targets without poly(A) tails (also referred to herein as non-polyadenylated targets), such as non-coding RNAs, histone mRNAs, and viral RNAs (e.g., reovirus mRNAs). For example, targets can be from two or more organisms, such as RNAs of a cell and RNAs of a bacterium, a fungus, or a virus. The cell can be infected by a bacterium, a fungus, and/or a virus. For example, a bead with oligonucleotide barcodes with poly(dT) regions for target binding and oligonucleotide barcodes with target-binding regions specific to viral mRNAs can be used to determine cellular phenotypes and viral genotypes during infection. In some embodiments, the targets are DNA targets (e.g., genomic DNA fragments without poly(A) tails).

In some embodiments, targets (e.g., mRNA transcripts of genes) include CD4, FOX01, CD45RO, MYC, IL1R2, PRF1, GZMK, LGALS1, IL17F, IL23R, LYNX1, PRDM1, SELL, SMAD4, ICOS, IKZF5, RORC, AHRR, CTLA4, ITGB7, ENTPD1, CCR8, TSHR, TGFB2, IL12A, IL7R, HLA-DMA, CCR5, TIAF1, BCL6, BHLHE40, CXCR4, and CD307c. Targets can include CD3D, GSTP1, TCF7, CD3E, RNB6, RB1, MYB, CD3G, KRT8, CDH1, ERBB3, ERBB2, TCTN1, ESR1, CDKN1A, and TFF3. Targets can include ABCB1, ABCG2, ADAM23, AKT1, APC, AR, ATM, BAD, BCL2, BIRCS, BRCA1, BRCA2, C4A, CA12, CCNA1, CCND1, CCND2, CCNE1, CDH1, CDH13, CDK2, CD326, CDKN1A, CDKN1C, CDKN2A, CSF1, CST6, CTNNB1, CTSD, EGF, EGFR, EMAP-2, ERBB2, ERBB3, ESR1, ESR2, FOXA1, GATA3, GLI1, GPI, GRB7, GSTP1, HIC1, HPRT1, ID1, IGF1, IGF1R, IGFBP3, IL6, JUN, KRT18, KRT19, KRTS, KRT8, LAMP1, MAPK1, MAPK3, MAPK8, MGMT, MKI67, MLH1, MMP2, MMP9, MUC1, MYB, MYC, NME1, NOTCH1, NR3C1, PGR, PLAU, PRDM2, PSMB2, PSMB4, PTEN, PTGS2, PYCARD, RAB7A, RARA, RARB, RASSF1, RB1, REEPS, RNB6, SERPINE1, SFN, SFRP1, SLC39A6, SLIT2, SNAI2, SRC, TBC1D9. TCTN1, TFF3, TGFB1, THBS1, TP73, TWIST1, VEGFA, XBP1, CD3E, CD3G, CD3G, TCF7, ALCAM, CD25, ITGA6, THY1, PROM1, and CXCR4. Targets can include BRCA1, BRCA2, TP53, PTEN, MSH2, MLH1, MSH6, PMS2, EPCAM, APC, RB1, MEN1, RET, and VHL.

The targets can be related to blood and lymph diseases; cancers; the digestive system; ear, nose, and throat; diseases of the eye; female-specific diseases; male-specific diseases; glands and hormones; heart and blood vessels; diseases of the immune system; male-specific diseases; muscle and bone; neonatal diseases; the nervous system; nutritional and metabolic diseases; respiratory diseases; and/or skin and connective tissue.

Samples and Cells of Interest

In some embodiments, the sample can be, or comprise, a clinical sample, a biological sample, an environmental sample, or a combination thereof. For example, the sample can include one or more of a biological fluid, tissues and cells from a subject. In some embodiments, the sample can include blood, urine, cerebrospinal fluid, pleural fluid, amniotic fluid, semen, saliva, bone marrow, a biopsy sample, or a combination thereof. In some embodiments, the cells of interest can include stem cells, cancer cells, blood cells, peripheral blood mononuclear cells, circulating tumor cells (CTCs), breast cancer cells, cells at a cell cycle phase of desire, or a combination thereof.

As used herein, the term "cells of interest" refer to cells being studied. Non-limiting examples of cells of interest in samples include cells expressing a malignant phenotype; tumor cells, such as tumor cells which have been shed from tumor into blood or other bodily fluids or bone marrow; benign tumor cells; cancer cells; cancer cells in peripheral blood; thyroid cancer cells; breast cancer cells; circulating tumor cells ("CTCs"); leukemia cells; cancer stem cells; single cells from different cell cycle phases (G0/G1, S, G2); sperms bearing X and Y chromosomes; stem cells; fetal or adult stem cells; multipotent stem cells; nucleated red blood cells ("NRBC") in Thalassemia patients; fetal cells, such as fetal cells in maternal peripheral blood; fetal nucleated red blood cells ("FNRBC") in the maternal circulation; and cells characterized by CD71, CD8, CD34, or CD133. Samples can comprise cells from a mixed cancer cell sample.

Other examples of cells of interest include, but are not limited to, the following cells: circulating endothelial cells; cells infected with a virus, such as cells infected by HIV, cells transfected with a gene of interest; and aberrant subtypes of T-cells or B-cells present in the peripheral blood of subjects afflicted with autoimmune or autoreactive disorders; activated lymphocytes; antigen presenting cells such as monocytes and dendritic cells; cells infected with pathogenic or parasitic organisms (e.g., *mycoplasma*), cells containing intracellular parasites; and cells or microorganisms in dilute fluids like urine.

Non-limiting examples of cell lines include: Jurkat cells, a T-leukemia cell line; SKBR3, an adenocarcinoma derived breast cancer cell line known for overexpression of Her2/neu; T47D, a ductal carcinoma derived breast cancer cell line that demonstrates low to intermediate Her2/neu expression; and HeLa.

In some embodiments, the plurality of targets can be comprised in one or more samples. A sample can comprise one or more cells, or nucleic acids from one or more cells. A sample can be a single cell or nucleic acids from a single cell. The one or more cells can be of one or more cell types. At least one of the one or more cell types can be brain cell, heart cell, cancer cell, circulating tumor cell, organ cell, epithelial cell, metastatic cell, benign cell, primary cell, circulatory cell, or any combination thereof.

A sample for use in the method of the disclosure can comprise one or more cells. A sample can refer to one or more cells. In some embodiments, the plurality of cells can include one or more cell types. At least one of the one or more cell types can be brain cell, heart cell, cancer cell, circulating tumor cell, organ cell, epithelial cell, metastatic cell, benign cell, primary cell, circulatory cell, or any combination thereof. In some embodiments, the cells are cancer cells excised from a cancerous tissue, for example, breast cancer, lung cancer, colon cancer, prostate cancer, ovarian cancer, pancreatic cancer, brain cancer, melanoma and non-melanoma skin cancers, and the like. In some embodiments, the cells are derived from a cancer but collected from a bodily fluid (e.g. circulating tumor cells). Non-limiting examples of cancers can include, adenoma, adenocarcinoma, squamous cell carcinoma, basal cell carcinoma, small cell carcinoma, large cell undifferentiated carcinoma, chondrosarcoma, and fibrosarcoma. The sample can include a tissue, a cell monolayer, fixed cells, a tissue section, or any combination thereof. The sample can include a biological sample, a clinical sample, an environmental sample, a biological fluid, a tissue, or a cell from a subject. The sample can be obtained from a human, a mammal, a dog, a rat, a mouse, a fish, a fly, a worm, a plant, a fungus, a bacterium, a virus, a vertebrate, or an invertebrate.

In some embodiments, the cells are cells that have been infected with virus and contain viral oligonucleotides. In some embodiments, the viral infection can be caused by a virus such as single-stranded (+ strand or "sense") DNA viruses (e.g. parvoviruses), or double-stranded RNA viruses (e.g. reoviruses). The beads disclosed herein can be used to determine the cellular phenotypes of infected cells and genotypes of viruses infecting the cells. For example, a bead with oligonucleotide barcodes with poly(dT) regions for target binding and oligonucleotide barcodes with target-binding regions specific to viral mRNAs can be used to simultaneously determine cellular phenotypes and/or genotypes and viral genotypes and/or phenotypes during infection. In some embodiments, the cells are cells that have been infected with bacteria (or fungi) and contain bacterial oligonucleotides (or fungal oligonucleotides). The beads disclosed herein can be used to simultaneously determine phenotypes and/or phenotypes of infected cells and genotypes and/or phenotypes of infecting organisms. In some embodiments, the cells are bacteria. These can include either gram-positive or gram-negative bacteria. In some embodiments, the cells are fungi. In some embodiments, the cells are protozoans or other parasites. In some embodiments, the cells are host cells of parasites. The beads disclosed herein can be used to simultaneously determine phenotypes and/or genotypes of host cells and genotypes and/or phenotypes of parasites.

As used herein, the term "cell" can refer to one or more cells. In some embodiments, the cells are normal cells, for example, human cells in different stages of development, or human cells from different organs or tissue types. In some embodiments, the cells are non-human cells, for example, other types of mammalian cells (e.g. mouse, rat, pig, dog, cow, or horse). In some embodiments, the cells are other types of animal or plant cells. In other embodiments, the cells can be any prokaryotic or eukaryotic cells.

In some embodiments the cells are sorted prior to associating a cell with a bead. For example the cells can be sorted by fluorescence-activated cell sorting or magnetic-activated cell sorting, or more generally by flow cytometry. The cells can be filtered by size. In some embodiments a retentate contains the cells to be associated with the bead. In some embodiments the flow through contains the cells to be associated with the bead.

A sample can refer to a plurality of cells. The sample can refer to a monolayer of cells. The sample can refer to a thin section (e.g., tissue thin section). The sample can refer to a solid or semi-solid collection of cells that can be place in one dimension on an array.

Sequencing

In some embodiments, estimating the number of different barcoded targets (e.g., stochastically barcoded targets) can comprise determining the sequences of the labeled targets, the spatial label, the molecular label, the sample label, the cell label, or any product thereof (e.g. labeled-amplicons, or labeled-cDNA molecules). An amplified target can be subjected to sequencing. Determining the sequence of a barcoded target (e.g., a stochastically barcoded target) or any product thereof can comprise conducting a sequencing reaction to determine the sequence of at least a portion of a sample label, a spatial label, a cell label, a molecular label, at least a portion of the labeled target (e.g., stochastically labeled target), a complement thereof, a reverse complement thereof, or any combination thereof.

Determination of the sequence of a barcoded target or a stochastically barcoded target (e.g. amplified nucleic acid, labeled nucleic acid, cDNA copy of a labeled nucleic acid, etc.) can be performed using variety of sequencing methods including, but not limited to, sequencing by hybridization (SBH), sequencing by ligation (SBL), quantitative incremental fluorescent nucleotide addition sequencing (QIFNAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads, wobble sequencing, multiplex sequencing, polymerized colony (POLONY) sequencing; nanogrid rolling circle sequencing (ROLONY), allele-specific oligo ligation assays (e.g., oligo ligation assay (OLA), single template molecule OLA using a ligated linear probe and a rolling circle amplification (RCA) readout, ligated padlock probes, or single template molecule OLA using a ligated circular padlock probe and a rolling circle amplification (RCA) readout), and the like.

In some embodiments, determining the sequence of the barcoded target (e.g., stochastically barcoded target) or any product thereof comprises paired-end sequencing, nanopore sequencing, high-throughput sequencing, shotgun sequencing, dye-terminator sequencing, multiple-primer DNA sequencing, primer walking, Sanger dideoxy sequencing, Maxim-Gilbert sequencing, pyrosequencing, true single molecule sequencing, or any combination thereof. Alternatively, the sequence of the barcoded target or any product thereof can be determined by electron microscopy or a chemical-sensitive field effect transistor (chemFET) array.

High-throughput sequencing methods, such as cyclic array sequencing using platforms such as Roche 454, Illumina Solexa, ABI-SOLiD, ION Torrent, Complete Genomics, Pacific Bioscience, Helicos, or the Polonator platform, can be utilized. In some embodiment, sequencing can comprise MiSeq sequencing. In some embodiment, sequencing can comprise HiSeq sequencing.

The labeled targets (e.g., stochastically labeled targets) can comprise nucleic acids representing from about 0.01% of the genes of an organism's genome to about 100% of the genes of an organism's genome. For example, about 0.01% of the genes of an organism's genome to about 100% of the genes of an organism's genome can be sequenced using a target complimentary region comprising a plurality of multimers by capturing the genes containing a complimentary sequence from the sample. In some embodiments, the barcoded targets comprise nucleic acids representing from about 0.01% of the transcripts of an organism's transcriptome to about 100% of the transcripts of an organism's transcriptome. For example, about 0.501% of the transcripts of an organism's transcriptome to about 100% of the transcripts of an organism's transcriptome can be sequenced using a target complimentary region comprising a poly(T) tail by capturing the mRNAs from the sample.

Determining the sequences of the spatial labels and the molecular labels of the plurality of the barcodes (e.g., stochastic barcodes) can include sequencing 0.00001%, 0.0001%, 0.001%, 0.01%, 0.1%, 1%, 2%, 3%, 4%, 5%, 6%, 7%, 8%, 9%, 10%, 20%, 30%, 40%, 50%, 60%, 70%, 80%, 90%, 99%, 100%, or a number or a range between any two of these values, of the plurality of barcodes. Determining the sequences of the labels of the plurality of barcodes, for example the sample labels, the spatial labels, and the molecular labels, can include sequencing 1, 10, 20, 30, 40, 50, 60, 70, 80, 90, 100, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$, or a number or a range between any two of these values, of the plurality of barcodes. Sequencing some or all of the plurality of barcodes can include generating sequences with read lengths of, of about, of at least, or of at most, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, or a number or a range between any two of these values, of nucleotides or bases.

Sequencing can comprise sequencing at least, or at least about, 10, 20, 30, 40, 50, 60, 70, 80, 90, 100, or more nucleotides or base pairs of the barcoded targets. For example, sequencing can comprise generating sequencing data with sequences with read lengths of 50, 75, or 100, or more nucleotides by performing polymerase chain reaction (PCR) amplification on the plurality of barcoded targets. Sequencing can comprise sequencing at least, or at least about, 200, 300, 400, 500, 600, 700, 800, 900, 1,000, or more nucleotides or base pairs of the barcoded targets. Sequencing can comprise sequencing at least, or at least about, 1500, 2000, 3000, 4000, 5000, 6000, 7000, 8000, 9000, or 10000, or more nucleotides or base pairs of the barcoded targets.

Sequencing can comprise at least about 200, 300, 400, 500, 600, 700, 800, 900, 1,000, or more sequencing reads per run. In some embodiments, sequencing comprises sequencing at least, or at least about, 1500, 2000, 3000, 4000, 5000, 6000, 7000, 8000, 9000, or 10000, or more sequencing reads per run. Sequencing can comprise less than or equal to about 1,600,000,000 sequencing reads per run. Sequencing can comprise less than or equal to about 200,000,000 reads per run.

EXAMPLES

Some aspects of the embodiments discussed above are disclosed in further detail in the following examples, which are not in any way intended to limit the scope of the present disclosure.

Example 1

Improved RNA Capture Using Beads with Spacer Oligonucleotides

This example shows beads with spacer oligonucleotides can capture RNA molecules with a higher efficiency compared to beads without spacer oligonucleotides.

Figure 6:
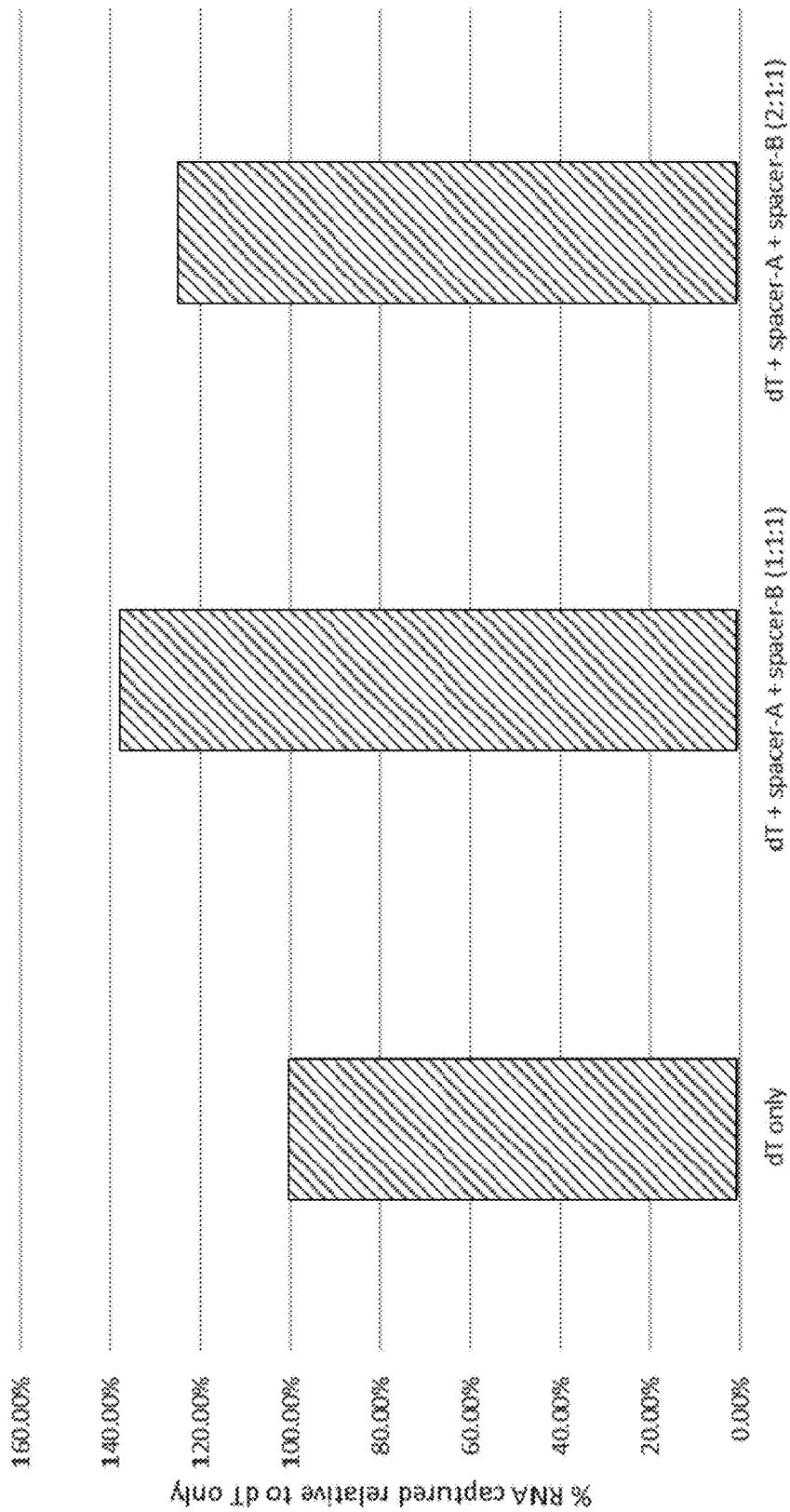
FIG. 6 is a bar chart showing non-limiting exemplary improvement in RNA capture using beads each comprising a plurality of oligonucleotide barcodes with oligo(dT) tails capable of capturing RNA molecules and a plurality of spacer oligonucleotides.

For beads with spacer oligonucleotides, quantitative polymerase chain reaction (qPCR) experiments with bulk RNA shows increased capture efficiency over beads without spacer oligonucleotides (FIG. 6). FIG. 6 is a bar chart showing non-limiting exemplary improvement in RNA capture using beads each comprising a plurality of oligonucleotide barcodes with oligo(dT) tails capable of capturing RNA molecules and a plurality of spacer oligonucleotides. The same amount of RNA was hybridized to 10000 beads (either with or without spacer oligonucleotides). After generating cDNA from the captured RNA molecules, qPCR was performed with primers amplifying GAPDH. Beads with spacer oligonucleotides were about 0.3-0.5 Cqs (quantification cycles, the cycle at which fluorescence from amplification exceeds the background fluorescence) lower than beads without spacer oligonucleotides. This means that the amount of GAPDH captured by spacer beads was about 125-138% relative to GAPDH captured by dT only beads.

Altogether, these data demonstrate RNA capture efficiency can be increased by decreasing the density of the oligonucleotide barcodes using spacer oligonucleotides.

Example 2

Target-Specific RNA Capture

This example shows beads with target-specific oligonucleotides can capture RNA molecules of interest with a higher efficiency compared to beads with oligonucleotides having poly(dT) regions for RNA capture.

Figure 7:
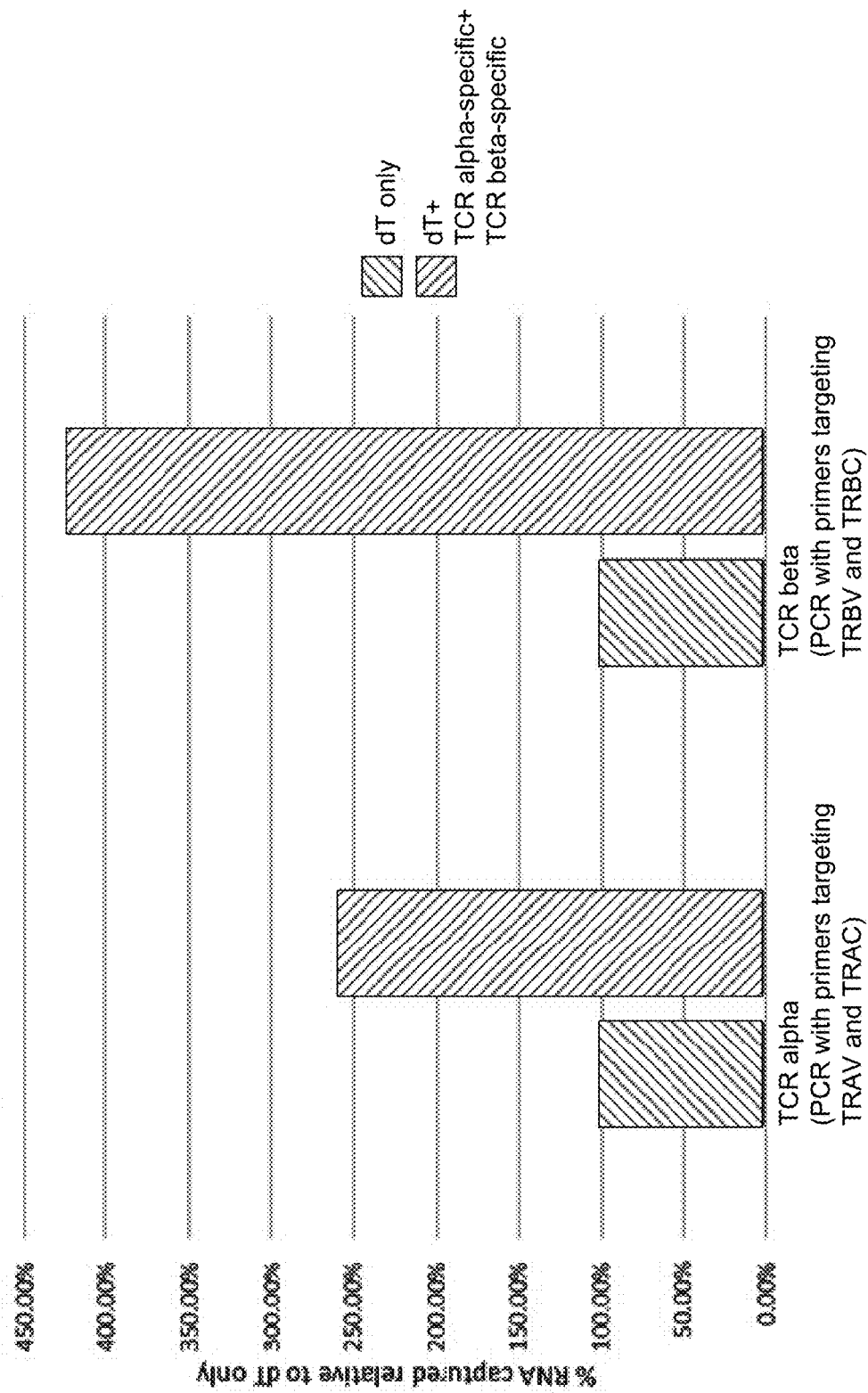
FIG. 7 is a bar chart showing a non-limiting exemplary comparison of T-Cell Receptor (TCR) capture efficiency using beads with TCR-specific oligonucleotide barcodes.

Target-specific oligonucleotides include target-binding regions with sequences 5'-ACAAGTCTGTCTG-3' (SEQ ID NO: 4) and 5'-CACACCCAAAAGGCCACACTGGT-3' (SEQ ID NO: 5) specific to the constant regions of TCR alpha and TCR beta. For beads with target-specific oligonucleotides (specific to the constant regions of TCR alpha and TCR beta), quantitative polymerase chain reaction (qPCR) experiments with bulk RNA shows increased capture efficiency over beads with oligonucleotides having poly(dT) sequences (FIG. 7). FIG. 7 is a bar chart showing a non-limiting exemplary comparison of T-Cell Receptor (TCR) capture efficiency using beads with TCR-specific oligonucleotide barcodes. The same amount of RNA was hybridized to 10000 beads (either with beads with oligonucleotides with poly(dT) target-binding regions or beads with oligonucleotides with poly(dT) target-binding regions and target-binding regions specific to the constant regions of TCR alpha and TCR beta). After generating cDNA from the captured RNA molecules, qPCR was performed using primers targeting the TCR alpha variable region and constant region and TCR beta variable region and constant region to amplify TCR alpha and TCR beta. The amount of TCR alpha molecules captured by beads with target-specific oligonucleotide barcodes was about 260% relative to TCR alpha captured by beads with oligonucleotide barcodes with oligo (dT) regions for non-specific target binding. The amount of TCR beta molecules captured by beads with target-specific oligonucleotide barcodes was about 425% relative to TCR beta captured by beads with oligonucleotide barcodes with oligo(dT) regions for non-specific target binding.

Altogether, these data demonstrate specific RNA capture efficiency can be increased using oligonucleotide barcodes with target-specific target-binding regions.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A synthetic particle, comprising:
   a first plurality of oligonucleotide barcodes; and
   a second plurality of oligonucleotide barcodes,
   wherein each of the first plurality of oligonucleotide barcodes and the second plurality of oligonucleotide barcodes comprises:
   an identical cellular label sequence; and
   a molecular label sequence,
   wherein at least 10 of the first plurality of oligonucleotide barcodes and the second plurality of oligonucleotide barcodes comprise different molecular label sequences,
   wherein each of the first plurality of oligonucleotide barcodes comprises a target-binding region, and
   wherein each of the second plurality of oligonucleotide barcodes comprises a target-specific target-binding region comprising a target-specific sequence for hybridizing to a target,
   wherein the target-binding region and the target-specific target-binding region are different.

2. The synthetic particle of claim 1, wherein the target-binding region of an oligonucleotide barcode of the first plurality of oligonucleotide barcodes comprises a poly(dT) region.

3. The synthetic particle of claim 2, wherein an oligonucleotide barcode of the second plurality of oligonucleotide barcodes comprises a poly(dT) region.

4. The synthetic particle of claim 1, wherein the ratio of the first plurality of oligonucleotide barcodes and the second plurality of oligonucleotide barcodes ranges from 1:10 to 10:1.

5. The synthetic particle of claim 1, comprising a first plurality of spacer oligonucleotides, wherein each of the first plurality of spacer oligonucleotides does not comprise the target-binding region and the target-specific target-binding region.

6. The synthetic particle of claim 1, wherein at least one of the first plurality of oligonucleotide barcodes is shorter than at least one of the second plurality of oligonucleotide barcodes.

7. The synthetic particle of claim 1, wherein two target-specific target-binding regions of two oligonucleotide barcodes of the second plurality of oligonucleotide barcodes comprise different target-specific sequences.

8. A kit comprising:
   a plurality of the synthetic particles of claim 1; and
   instructions for using the plurality of synthetic particles.

9. The kit of claim 8, wherein the plurality of synthetic particles comprises at least 94 synthetic particles.

10. The kit of claim 8, comprising a plurality of partitions each comprising a synthetic particle of the plurality synthetic particles.

11. The kit of any claim 10, wherein the plurality of partitions comprises microwells of a microwell array.

12. A synthetic particle, comprising:
   a plurality of oligonucleotide barcodes, wherein each of the plurality of oligonucleotide barcodes comprises:
   an identical cellular label sequence;
   a molecular label sequence; and
   a target-binding region,
   and wherein at least 10 of the plurality of oligonucleotide barcodes comprise different molecular label sequences; and
   a first plurality of spacer oligonucleotides, wherein each of the first plurality of spacer oligonucleotides does not comprise the target-binding region.

13. The synthetic particle of claim 12, wherein the ratio of the plurality of oligonucleotide barcodes and the first plurality of spacer oligonucleotides ranges from 1:10 to 10:1.

14. The synthetic particle of claim 12, wherein each of the first plurality of spacer oligonucleotides comprises a cellular label sequence or a molecular label sequence.

15. The synthetic particle of claim 12, wherein at least one of the first plurality of spacer oligonucleotides is shorter than at least one of the plurality of oligonucleotide barcodes.

16. The synthetic particle of claim 12, wherein each of the first plurality of spacer oligonucleotides comprises a region that corresponds to the target-binding region, and wherein the region that corresponds to the target-binding region and the target-binding region have different sequences.

17. The synthetic particle of claim 16, wherein the region that corresponds to the target-binding region and the target-binding region have at most 50% sequence identity.

18. The synthetic particle of claim 12, wherein the synthetic particle comprises a second plurality of spacer oligonucleotides, wherein each of the second plurality of spacer oligonucleotides does not comprise the target-binding region.

19. The synthetic particle of claim 18, wherein at least one of the second plurality of spacer oligonucleotides is shorter than at least one of the first plurality of spacer oligonucleotides.

20. The synthetic particle of claim 18, wherein at least one of the second plurality of spacer oligonucleotides is shorter than at least one of the plurality of oligonucleotide barcodes.

21. The synthetic particle of claim 12, wherein the target-binding region comprises a gene-specific sequence, an oligo (dT) sequence, a random multimer, or any combination thereof.

22. A kit comprising:
a plurality of the synthetic particles of claim 12; and
instructions for using the plurality of oligonucleotide barcodes.

23. The kit of claim 22, wherein the plurality of synthetic particles comprises at least 94 synthetic particles.

24. The kit of claim 22, comprising a microwell array, wherein each microwell of the microwell array comprises a synthetic particle of the plurality synthetic particles.

* * * * *

SEQUENCE LISTING

```
<160> NUMBER OF SEQ ID NOS: 5

<210> SEQ ID NO 1
<211> LENGTH: 103
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: n
<222> LOCATION: (78)..(85)
<223> OTHER INFORMATION: n = a, t, c, or g
<220> FEATURE:
<221> NAME/KEY: misc_feature
<222> LOCATION: (78)..(85)
<223> OTHER INFORMATION: n is a, c, g, or t

<400> SEQUENCE: 1
tctctctcta cacgacgctc ttccgatctg atggatgact ggcctgcgac tacacgaggt      60
agcggtgact tccaaggnnn nnnnntttt tttttttttt ttt                        103

<210> SEQ ID NO 2
<211> LENGTH: 103
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: n
<222> LOCATION: (78)..(103)
<223> OTHER INFORMATION: n = a, t, c, or g
<220> FEATURE:
<221> NAME/KEY: misc_feature
<222> LOCATION: (78)..(103)
<223> OTHER INFORMATION: n is a, c, g, or t

<400> SEQUENCE: 2
tctctctcta cacgacgctc ttccgatctg atggatgact ggcctgcgac tacacgaggt      60
agcggtgact tccaaggnnn nnnnnnnnn nnnnnnnnnn nnn                        103

<210> SEQ ID NO 3
<211> LENGTH: 121
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: n
<222> LOCATION: (75)..(85)
<223> OTHER INFORMATION: n = a, t, c, or g
<220> FEATURE:
<221> NAME/KEY: misc_feature
<222> LOCATION: (78)..(85)
<223> OTHER INFORMATION: n is a, c, g, or t
<220> FEATURE:
<221> NAME/KEY: n
<222> LOCATION: (104)..(121)
<223> OTHER INFORMATION: n = a, t, c, or g
```

```
<220> FEATURE:
<221> NAME/KEY: misc_feature
<222> LOCATION: (104)..(121)
<223> OTHER INFORMATION: n is a, c, g, or t

<400> SEQUENCE: 3
tctctctcta cacgacgctc ttccgatctg atggatgact ggcctgcgac tacacgaggt      60
agcggtgact tccaaggnnn nnnnntttt tttttttttt tttnnnnnnn nnnnnnnnnn     120 n                                                                     121

<210> SEQ ID NO 4
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 4
acaagtctgt ctg                                                         13

<210> SEQ ID NO 5
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 5
cacacccaaa aggccacact ggt                                              23
```